(12) United States Patent
Wang et al.

(10) Patent No.: US 7,910,350 B2
(45) Date of Patent: *Mar. 22, 2011

(54) ADAPTOR-DIRECTED HELPER SYSTEMS

(75) Inventors: Caili Wang, San Francisco, CA (US); Pingyu Zhong, Mountain View, CA (US); Xinwei Wang, San Jose, CA (US)

(73) Assignee: Abmaxis, Inc., Rahway, NJ (US)

( * ) Notice: Subject to any disclaimer, the term of this patent is extended or adjusted under 35 U.S.C. 154(b) by 884 days.

This patent is subject to a terminal disclaimer.

(21) Appl. No.: 11/313,270

(22) Filed: Dec. 19, 2005

(65) Prior Publication Data

US 2006/0281181 A1 Dec. 14, 2006

Related U.S. Application Data

(63) Continuation of application No. 10/033,399, filed on Nov. 2, 2001, now Pat. No. 7,175,983.

(51) Int. Cl.
*C12N 7/01* (2006.01)
(52) U.S. Cl. .............. 435/235.1; 435/320.1; 435/6
(58) Field of Classification Search .............. None
See application file for complete search history.

(56) References Cited

U.S. PATENT DOCUMENTS

| | | | |
|---|---|---|---|
| 3,817,837 A | 6/1974 | Rubenstein et al. | 195/103.5 R |
| 3,850,752 A | 11/1974 | Schuurs et al. | 195/103.5 R |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 5,091,513 A | 2/1992 | Huston et al. | 530/387 |
| 5,233,409 A | 8/1993 | Schwab | 356/402 |
| 5,270,202 A | 12/1993 | Raychaudhuri | 435/240.27 |
| 5,348,867 A | 9/1994 | Georgiou et al. | 435/69.7 |
| 5,403,484 A | 4/1995 | Ladner et al. | 435/235.1 |
| 5,405,783 A | 4/1995 | Pirrung et al. | 436/581 |
| 5,412,087 A | 5/1995 | McGall et al. | 536/24.3 |
| 5,427,908 A | 6/1995 | Dower et al. | 435/5 |
| 5,445,934 A | 8/1995 | Fodor et al. | 435/6 |
| 5,514,548 A | 5/1996 | Krebber et al. | 435/6 |
| 5,571,698 A | 11/1996 | Ladner et al. | 435/69.7 |
| 5,695,937 A | 12/1997 | Kinzler et al. | 435/6 |
| 5,731,168 A | 3/1998 | Carter et al. | 435/69.1 |
| 5,738,996 A | 4/1998 | Hodges et al. | 435/7.1 |
| 5,770,442 A | 6/1998 | Wickham et al. | |
| 5,807,706 A | 9/1998 | Carter et al. | 435/69.1 |
| 5,821,333 A | 10/1998 | Carter et al. | 530/350 |
| 5,824,483 A | 10/1998 | Houston, Jr. et al. | 435/7.1 |
| 5,830,721 A | 11/1998 | Stemmer et al. | 435/172.1 |
| 5,837,500 A | 11/1998 | Ladner et al. | 435/69.7 |
| 5,849,500 A | 12/1998 | Breitling et al. | 435/7.1 |
| 5,858,657 A | 1/1999 | Winter et al. | 435/6 |
| 5,869,337 A | 2/1999 | Crabtree et al. | 435/372.3 |
| 5,885,793 A | 3/1999 | Griffiths et al. | 435/69.1 |
| 5,910,573 A | 6/1999 | Plükthun et al. | 530/387.3 |
| 5,932,448 A | 8/1999 | Tso et al. | 435/69.6 |
| 5,955,341 A | 9/1999 | Kang et al. | 435/235.1 |
| 5,965,368 A | 10/1999 | Vidal et al. | 435/6 |
| 5,969,108 A | 10/1999 | McCafferty et al. | 530/387.3 |
| 6,010,884 A | 1/2000 | Griffiths et al. | 435/69.7 |
| 6,027,930 A | 2/2000 | Borrebaeck | 435/235 |
| 6,083,693 A | 7/2000 | Nandabalan et al. | 435/6 |
| 6,127,132 A | 10/2000 | Breitling et al. | 435/7.1 |
| 6,129,914 A | 10/2000 | Weiner et al. | 424/133.1 |
| 6,130,037 A | 10/2000 | Lennox et al. | 435/6 |
| 6,132,963 A | 10/2000 | Brent et al. | 435/6 |
| 6,140,471 A | 10/2000 | Johnson et al. | 530/387.3 |
| 6,159,705 A | 12/2000 | Trueheart et al. | 435/29 |
| 6,165,793 A | 12/2000 | Stemmer | 435/440 |
| 6,171,792 B1 | 1/2001 | Brent et al. | 435/6 |
| 6,174,708 B1 | 1/2001 | Sodoyer et al. | 435/91.1 |
| 6,180,406 B1 | 1/2001 | Stemmer | 435/440 |
| 6,248,516 B1 | 6/2001 | Winter et al. | 435/6 |
| 6,593,081 B1 | 7/2003 | Griffiths et al. | |
| 2003/0104604 A1 | 6/2003 | Yang et al. | 435/235.1 |

FOREIGN PATENT DOCUMENTS

| | | |
|---|---|---|
| EP | 0 368684 B1 | 9/1994 |
| EP | 0 699755 A2 | 6/1996 |
| EP | 0 699755 A3 | 6/1996 |
| WO | WO 88/06630 | 9/1988 |
| WO | WO 90/02809 | 2/1990 |
| WO | WO 90/05144 | 5/1990 |
| WO | WO 91/17271 | 11/1991 |
| WO | WO 92/01047 | 1/1992 |
| WO | WO 92/15679 | 9/1992 |
| WO | WO 93/10247 | 5/1993 |
| WO | WO 93/11236 | 6/1993 |
| WO | WO 95/26400 | 10/1995 |

(Continued)

OTHER PUBLICATIONS

Abel and Maniatis, (1989) "Gene Regulation. Action of Leucine Zippers," *Nature*, 341(6237):24-5. Adey, et al., (1996) "Construction of Random Peptide Libraries in Bacteriophage M13," Chapter 5, *Phage Display of Peptides and Proteins: A Laboratory Manual*, Academic Press, Inc.

Armstrong, et al., (1996) "Vectors for Phage Display," Chapter 3, *Phage Display of Peptides and Proteins: A Laboratory Manual*, Academic Press, Inc.

Ausubel, et al., eds., (1987) "Current Protocols in Molecular Biology" [Table of Contents provided].

Ausubel, et al., eds., (1995) "Short Protocols in Molecular Biology" Third Edition [Table of Contents provided].

Baker, et al., (1987) "Genetics and Biochemistry of the Assembly of Proteins Into the Outer Membrane of *E. Coli*," *Prog Biophys Mol Biol*, 49(2-3):89-115.

(Continued)

*Primary Examiner* — James S Ketter
(74) *Attorney, Agent, or Firm* — Patricia L. Chisholm; Immac J. Thampoe

(57) ABSTRACT

The present invention provides adapter-directed display systems for expressing exogenous polypeptide within a host cell and/or displaying the exogenous polypeptide on the outer surface of a genetic package. This subject systems are particularly useful for displaying a genetically diverse repertoire of monomeric and multimeric polypeptides. The invention also provides both expression and helper vectors and kits containing components of the subject display systems. Also provided are genetic packages displaying the exogenous polypeptides of particular interest. Further provided by the invention are methods of using the subject display systems.

11 Claims, 36 Drawing Sheets

FOREIGN PATENT DOCUMENTS

| | | | |
|---|---|---|---|
| WO | WO 97/08320 | | 3/1997 |
| WO | WO 98/28624 | * | 7/1998 |
| WO | WO 99/14319 | | 3/1999 |
| WO | WO 99/42597 | | 8/1999 |
| WO | WO 00/14222 | | 3/2000 |
| WO | WO 01/05950 A2 | | 1/2001 |

OTHER PUBLICATIONS

Banerji, et al., (1983) "A Lymphocyte-Specific Cellular Enhancer is Located Downstream of the Joining Region in Immunoglobulin Heavy Chain Genes" *Cell*, 33(3):729-740.

Barbas, et al., (2001) *Phage Display: A Laboratory Manual*, Cold Spring Harbor Laboratory Press [Table of Contents provided].

Barbas, et al., (1991) "Assembly of Combinatorial Antibody Libraries on Phage Surfaces: the Gene III Site," *Proc Natl Acad Sci USA*, 88(18):7978-7982.

Barbas, et al., (1992) "Semisynthetic Combinatorial Antibody Libraries: A Chemical Solution to the Diversity Problem," *Proc Natl Acad Sci U S A*, 89(10):4457-4461.

Barnes, et al., (1980) "Methods for Growth of Cultured Cells in Serum-Free Medium," *Anal. Biochem.*, 102(2):255-270.

Belshaw, et al., (1996) "Controlling Protein Association and Subcellular Localization With a Synthetic Ligand That Induces Heterodimerization of Proteins" *Proc. Natl. Acad. Sci. U.S.A.*, 93(10):4604-4607.

Benson, et al. (1987) "In Vivo Selection and Characterization of Internal Deletions in the LamB::IacZ Gene Fusion" *Gene*, 52(2-3):165-73.

Benson, et al., (1984) "Intragenic Regions Required for LamB Export" *Proc. Natl. Acad. Sci U.S.A.*, 81(12):3830-34.

Bird, et al., (1988) "Single-Chain Antigen-Binding Proteins" *Science*, 242(4877):423-426.

Blankenstein, et al., (1988) "A Retroviral Expression Vector Containing Murine Immunoglobulin Heavy Chain Promoter/Enhancer" *Nucleic Acid Res.*, 16(22):10939.

Brinkmann, et al., (1993) "A Recombinant Immunotoxin Containing a Disulfide-Stabilized Fv Fragment" *Proc. Natl. Acad. Sci. U.S.A.*, 90(16):7538-7542.

Burkhard, et al., (2001) "Coiled Coils: A Highly Versatile Protein Folding Motif," *Trends in Cell Biology*, 11(2):82-88.

Cantley, et al. (1991) "Oncogenes and Signal Transduction," *Cell*, 64(2):281-302.

Chatal, et al., (1985) "Clinical Prospective Study With Radioiodinated Monoclonal Antibodies Directed Against Colorectal Cancer," *Monoclonal Antibodies for Cancer Detection and Therapy*, Academic Press, Chapter 8, pp. 159-180.

Cohen, et al., (1989) "The Prochict of a Fos-Related Gene, Fra-1, Binds Cooperatively to the AP-1 Site With Jun: Transcription Factor AP-1 is Comprised of Multiple Protein Complexes," *Genes Dev.*, 3(2):173-84.

Cook and Tomlinson, (1995) "The Human Immunoglobulin VH Repertoire," *Immunol Today*, 16(5):237-242.

Cornelis, (2000) "Expressing Genes in Different *Escherichia coli* Compartments," *Curr Opin Biotechnol.*, 11(5):450-454.

Crameri and Suter, (1993) "Display of Biologically Active Proteins on the Surface of Filamentous Phages: a cDNA Cloning System for Selection of Functional Gene Products Linked to the Genetic Information Responsible for Their Production," *Gene*, 137(1):69-75.

Daugherty, et al. (1999) "Development of an Optimized Expression System for the Screening of Antibody Libraries Displayed on the *Escherichia coli* Surface," *Protein Eng.*, 12(7):613-621.

de Geus, et al., (1984) "The Pro- and Mature Forms of the *E. coli* K-12 Outer Membrane Phospholipase a are Identical" *EMBO J.*, 3(8):1799-1802.

De Haard, et al., (1999) "A Large Non-Immunized Human Fab Fragment Phage Library That Permits Rapid Isolation and Kinetic Analysis of High Affinity Antibodies," *J Biol Chem.*, 274(26):18218-18230.

De Kruif and Logtenberg, (1986) "Leucine Zipper Dimerized Bivalent and Bispecific scFv Antibodies From a Semi-synthetic Antibody Phage Display Library," *J. Biol. Chem.*, 271(13):7630-7634.

Donovan, et al., (1987) "Genes Encoding Spore Coat Polypeptides From *Bacillus subtilis*," *J Mol Biol.*, 196(1):1-10.

Frank, et al., (2000) "A Distinct Seven-Residue Trigger Sequence is Indispensable for Proper Coiled-Coil Formation of the Human Macrophage Scavenger Receptor Oligomerization Domain" *J. Biol. Chem.*, 275(16):11672-11677.

Freshney, (1987) "Animal Cell Culture" [Table of Contents provided].

Gillies, et al., (1983) "A Tissue-Specific Transcription Enhancer Element Is Located in the Major Intron of a Rearranged Immunoglobulin Heavy Chain Gene" *Cell*, 33(3):717-728.

Glaser, et al., (1992) "Dissection of the Combining Site in a Humanized Anti-Tac Antibody" *J. Immunol.*, 149(8):2607-2614.

Glockshuber, et al., (1990) "A Comparison of Strategies to Stabilize Immunoglobulin Fv-Fragments" *Biochemistry*, 29(6):1362-1367.

Goeddel, ed., "Gene Expression Technology," Academic Press, Inc. [Table of Contents provided].

Gentz, et al., (1989) "Parallel Association of Fos and Jun Leucine Zippers Juxtaposes DNA Binding Domains," *Science*, 243(4899):1695-9.

Geoffroy, et al. (1994) A New Phage Display System to Construct Multicombinatorial Libraries of Very Large Antibody Repertoires. *Gene*, 151(1-2):109-13.

Gomes, et al., (2000) "Heterodimerization of Mu and Delta Opiod Receptors: A Role in Opiate Synergy," *J. Neurosci.*, 20(22):RC110.

Gram, et al., (1992) "In Vitro Selection and Affinity Maturation of Antibodies From a Naive Combinatorial Immunoglobulin Library," *Proc Natl Acad Sci U S A*, 89(8):3576-3580.

Griffiths, et al., (1994) "Isolation of High Affinity Human Antibodies Directly From Large Synthetic Repertoires," *EMBO J.*, 13(14):3245-3260.

Gudmundsdottir, et al., (1989) "Point Mutations in a Conserved Region (TonB Box) of *Escherichia coli* Outer Membrane Protein BtuB Affect Vitamin B12 Transport," *J Bacteriol.*, 171(12):6526-33.

Hantzopoulos, et al., (1989) "Improved Gene Expression Upon Transfer of the Adenosine Deaminase Minigene Outside the Transcriptional Unit of a Retroviral Vector" *Proc. Natl. Acad. Sci. U.S.A.*, 86(10):3519-3523.

Harlow and Lane (1988) "Antibodies: A Laboratory Manual," Cold Spring Harbor Laboratory, New York [Table of Contents provided].

Hawkins, et al., (1992) "Selection of Phage Antibodies by Binding Affinity. Mimicking Affinity Maturation," *J Mol Biol.*, 226(3):889-896.

Holliger, et al., (1993) "'Diabodies': Small Bivalent and Bispecific Antibody Fragments," *Proc. Natl. Acad. Sci. U.S.A.*, 90(14):6444-6448.

Hoogenboom and Chames, (2000) "Natural and Designer Binding Sites Made by Phage Display Technology," *Immunology Today*, 21(8):371-378.

Huston, et al., (1988) "Protein Engineering of Antibody Binding Sites: Recovery of Specific Activity in an Anti-Digoxin Single-Chain Fv Analogue Produced in *Escherichia coli*," *Proc. Natl. Acad. Sci. U.S.A.*, 85(16):5879-5883.

Jabet, et al., (1999) "NMR Studies of the Pbx1 TALE Homeodomain Protein Free in Solution and Bound to DNA: Proposal for A Mechanism of HoxB1-Pbx1-DNA Complex Assembly," *J Mol Biol.* 291(3):521-530.

Jansen, et al., (1985) "Efficiency and Tolerance of the Treatment With Immuno-A-Chain-Toxins in Human Bone Marrow Transplantations," *Monoclonal Antibodies for Cancer Detection and Therapy*, Academic Press, Chapter 11, pp. 223-248.

Jordan, et al., (1999) "G-Protein-Coupled Receptor Heterodimerization Modulates Receptor Function," *Nature*, 399(6737):697-700.

Junius, et al., (1996) "High Resolution NMR Solution Structure of the Leucine Zipper Domain of the c-Jun Homodimer," *J. Biol. Chem.*, 271(23):13663-13667.

Kammerer, et al., (1998) "An Autonomous Folding Unit Mediates The Assembly of Two-Stranded Coiled Coils," *Biochemistry*, 95(23):13419-13424.

Kammerer, et al., (1999) "Heterodimerization of a Functional $GABA_B$ Receptor is Mediated by Parallel Coiled-Coil a-Helices," *Biochemistry*, 38(40):13263-13269.

Kang, et al., (1991) "Linkage of Recognition and Replication Functions by Assembling Combinatorial Antibody Fab Libraries Along Phage Surfaces," *Proc Natl Acad Sci U S A*, 88(10):4363-4366.

Kay, et al., (1996) *Phage Display of Peptides and Proteins: A Laboratory Manual*, Academic Press, Inc. [Table of Contents provided].

Kay and Hoess, (1996) "Principles and Applications of Phage Display," Chapter 2, *Phage Display of Peptides and Proteins: A Laboratory Manual*, Academic Press, Inc.

Kim, et al., (1999) "Cell Surface Display of Hepatitis B Virus Surface Antigen by Using *Pseudomonas* Syringae Ice Nucleation Protein," *Lett Appl Microbiol.*, 29(5):292-7.

Kuner, et al., (1999) "Role of Heteromer Formation in $GABA_B$ Receptor Function," *Science*, 283(5398):74-77.

Lang, (2000) "Outer Membrane Proteins as Surface Display Systems," *Int J Med Microbiol.*, 290(7):579-585.

Larrick, et al., (1989) "Rapid Cloning of Rearranged Immunoglobulin Genes From Human Hybridoma Cells Using Mixed Primers and the Polymerase Chain Reaction," *Biochem. Biophys. Res. Commun.*, 160(3):1250-1255.

Levitt, et al., (1983) "Molecular Dynamics of Native Protein. I. Computer Simulation of Trajectories," *J. Mol. Biol.*, 168:595-617.

Light, et al., (1996) "Expression Cloning of cDNA by Phage Display Selection," *Nucleic Acids Research*, 24(21):4367-4368.

Liscovitch, et al., (1994) "Lipid Second Messengers," *Cell*, 77(3):329-34.

Little, et al., (2000) "Of Mice and Men: Hybridoma and Recombinant Antibodies," *Immunology Today*, 21(8):364-370.

Losick, et al., (1986) "Genetics of Endospore Formation in *Bacillus subtilis*," *Annu Rev Genet.*, 20:625-69.

Luiten, et al., (1985) "Nucleotide Sequence of the Genome of Pf3, an IncP-1 Plasmid-Specific Filamentous Bacteriophage of *Pseudomonas Aeruginosa*," *J Virol.*, 56(1):268-76.

Luiten, et al., (1991) "In Vitro Deletion Mapping of the Viral Strand Replication Origin of *Pseudomonas* Bacteriophage Pf3," *J Bacteriol.*, 173(13):4007-12.

Marks, et al., (1991) "By-Passing Immunization. Human Antibodies From V-Gene Libraries Displayed on Phage," *J Mol Biol.*, 222(3):581-597.

Mason, et al., (1985) "Transcription Cell Type Specificity is Conferred by an Immunoglobulin VH Gene Promoter That Includes a Functional Consensus Sequence," *Cell*, 41(2):479-487.

Matthews, (1991) "Plant Virology," 3$^{rd}$ edition.

McCafferty, et al., (1990) "Phage Antibodies: Filamentous Phage Displaying Antibody Variable Domains," *Nature*, 348(6301):552-4.

McIvor, et al., (1987), "Human Purine Nucleoside Phosphorylase and Adenosine Deaminase: Gene Transfer Into Cultured Cells and Murine Hematopoietic Stem Cells by Using Recombinant Amphotropic Retroviruses," *Mol. Cell. Biol.*, 7(2):838-846.

McPherson, et al., eds. (1995) "PCR 2: A Practical Approach" [Table of Contents provided].

Miltenyi, et al., (1990) "High Gradient Magnetic Cell Separation With MACS," *Cytometry*, 11(2):231-238.

Misra, et al., (1988) "Isolation and Characterization of OmpC Porin Mutants With Altered Pore Properties," *J Bacteriol.*, 170(2):528-33.

Myers (1985) "The Use of Immunotoxins to Eliminate Tumor Cells From Human Leukaemic Marrow Autografts," *Monoclonal Antibodies for Cancer Detection and Therapy*, Academic Press, Chapter 12, pp. 249-267.

Nakabeppu, et al., (1988) "DNA Binding Activities of Three Murine Jun Proteins: Stimulation by Fos.," *Cell*, 55(5):907-15.

O'Shea, et al., (1992) "Mechanism of Specificity in the Fos-Jun Oncoprotein Heterodimer," *Cell*, 68(4):699-708.

Olsnes and Pihl, (1981) "Chimeric Toxins," *Pharmac. Ther.*, 15(3):355-381.

Orlandi, et al. (1989) "Cloning Immunoglobulin Variable Domains for Expression by the Polymerase Chain Reaction," *Proc. Natl. Acad. Sci. U.S.A.*, 86(10):3833-3837.

Pages, et al., (1990) "Immunological Approach of Assembly and Topology of OmpF, an Outer Membrane Protein of *Escherichia coli*," *Biochemimie*, 72(2-3):169-76.

Parmley, et al., (1988) "Antibody-Selectable Filamentous fd Phage Vectors: Affmity Purification of Target Genes," *Gene*, 73(2):305-18.

Peng, et al., (1988) "Retroviral-Mediated Gene Transfer and Expression of Human Phenylalanine Hydroxylase in Primary Mouse Hepatocytes," *Proc. Natl. Acad. Sci. U.S.A.*, 85(21):8146-8150.

Pini, et al. (1998) "Design and Use of a Phage Display Library. Human Antibodies With Subnanomolar Affinity Against a Marker of Angiogenesis Eluted From a Two-Dimensional Gel," *J Biol Chem.*, 273(34):21769-21776.

Piper, et al., (1999) "Structure of a HoxB1-Pbx1 Heterodimer Bound to DNA: Role of the Hexapeptide and a Fourth Homeodomain Helix in Complex Formation," *Cell*, 96(4):587-597.

Rider, et al., (1996) "Microbiological Methods," Chapter 4, *Phage Display of Peptides and Proteins: A Laboratory Manual*, Academic Press, Inc.

Rondot, et al., (2001) "A Helper Phage to Improve Single-Chain Antibody Presentation in Phage Display," *Nature Biotechnology*, 19(1):75-78.

Sambrook, et al., (1989) "Molecular Cloning: A Laboratory Manual," 2$^{nd}$ edition [Table of Contents provided].

Sanford, et al., (1993) "Optimizing the Biolistic Process for Different Biological Applications," *Methods in Enzymology*, 217:483-509.

Sastry, et al., (1989) "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. U.S.A.*, 86(15)15728-5732.

Sato, et al., (1982) "Growth of Cells in Hormonally Defined Media," Cold Spring Harbor Press, N.Y. [Table of Contents provided].

Sblattero, et al, (1997) "A Definitive Set of Oligonucleotide Primers for Amplifying Human V Regions," *Immunotechnology*, 3(4)171-278.

Scott and Barbas, (2001) "Phage-Display Vectors," Chapter 2, *Phage Display: A Laboratory Manual*, Cold Spring Harbor Laboratory Press.

Shalaby, et al., (1992) "Development of Humanized Bispecific Antibodies Reactive with Cytotoxic Lymphocytes and Tumor Cells Overexpressing the HER2 Protooncogene," *J. Exp. Med.*, 175(1):217-225.

Sheets, et al., (1998) "Efficient Construction of a Large Nonimmune Phage Antibody Library: the Production of High-Affinity Human Single-Chain Antibodies to Protein Antigens," *Proc Natl Acad Sci U S A*, 95(11):6157-6162.

Sidhu, (2000) "Phage Display in Pharmaceutical Biotechnology," *Curr Opin Biotechnol.*, 11(6):610-616.

Smith, et al., (1985) "Filamentous Fusion Phage: Novel Expression Vectors that Display Cloned Antigens on the Virion Surface," *Science*, 228(4705):1315-17.

So, et al., (1985) "Gonococcal Pilus: Genetics and Structure," *Curr Top in Microbial & Immunol*, 118:13-28.

Soderlind, et al. (2000) "Recombining Germline-Derived CDR Sequences for Creating Diverse Single-Framework Antibody Libraries," *Nat Biotechnol.*, 18(8):852-856.

Songyang, et al., (1993) "SH2 Domains Recognize Specific Phosphopeptide Sequences" *Cell*, 72(5):767-778.

Songyang, et al., (1995) "A Single Point Mutation Switches the Specificity of Group III Src Homology (SH) 2 Domains to That of Group I SH2 Domains" *J. Biol. Chem.*, 270(44):26029-26032.

Stemmer, et al., (1993) "Selection of an Active Single Chain Fv Antibody From a Protein Linker Library Prepared by Enzymatic Inverse PCR," *Biotechniques*, 14(2):256-265.

Tabin, et al., (1982) "Adaptation of a Retrovirus as a Eucaryotic Vector Transmitting the Herpes Simplex Virus Thymidine Kinase Gene," *Mol. Cell. Biol.*, 2(4):426-436.

Tempest, et al., (1991) "Reshaping a Human Monoclonal Antibody to Inhibit Human Respiratory Syncytial Virus Infection in Vivo," *Biotechnology*, 9(3):266-271.

Thorpe, et al., (1982) "Monoclonal Antibody-Toxin Conjugates: Aiming the Magic Bullet," *Monoclonal Antibodies in Clinical Medicine*, Academic Press, pp. 168-190.

van Assendelft, et al., (1989) "The Beta-Globin Dominant Control Region Activates Homologous and Heterologous Promoters in a Tissue-Specific Manner," *Cell*, 56(6):969-977.

van der Ley, et al., (1986) "Topology of Outer Membrane Pore Protein PhoE of *Escherichia coli*," *J. Biol. Chem.*, 261(26):12222-12225.

Vidal, et al., (1996) "Reverse Two-Hybrid and One-Hybrid Systems to Detect Dissociation of Protein-Protein and DNA Protein Interactions," *Proc. Natl. Acad. Sci.* U.S.A, 93(19):10315-10320.

Viega, et al., (1999) "Probing Secretion and Translocation of a Beta-Autotransporter Using a Reporter Single-Chain Fv as a Cognate Passenger Domain," *Mol Microbiol*., 33(6):1232-43.

Vitetta, et al. (1987) "Redesigning Nature's Poisons to Create Anti-Tumor Reagents," *Science*, 238(4830):1098-1304.

Ward, et al., (1989) "Binding Activities of a Repertoire of Single Immunoglobulin Variable Domains Secreted from *Escherichia coli*," *Nature*, 341(6242):544-546.

Waterhouse, et al., (1993) "Combinatorial Infection and In Vivo Recombination: a Strategy for Making Large Phage Antibody Repertoires," *Nucleic Acids Res*., 21(9):2265-6.

White, et al., (1998) "Heterodimerization is Required for the Formation of a Functional $BABA_B$ Receptor," *Nature*, 396(6712):679-682.

Winter and Milstein (1991) "Man-made Antibodies," *Nature*, 349(6307):293-299.

Winter, et al., (1994) "Making Antibodies by Phage Display Technology," *Ann. Rev. Immunol*., 12:433-455.

Wolf, et al., (1997) "MultiCoil: A Program for Predicting Two- and Three-Stranded Coiled Coils," *Protein Sci*., 6(6):1179-1189.

Zhou et al., (1983) "Introduction of Exogenous DNA into Cotton Embryos," *Methods in Enzymology*, 101:433-481.

Bergh, Michel L. E. et al. Expression of the *Sacchararnyces cerevisiae* Glycoprotein Invertase in Mouse Fibroblasts: Glycosylation, Secretion, and Enqymatic Activity. *Proc. Natl. Acad. Sci.* (1987) 84:(11) 3570-3574.

Bird, Phillip et al. "Translocation in Yeast and Mammalian Cells: Not All Signal Sequences are Functionally Equivalent" *The Journal of Cell Biology* (1987) 105:(6) 2905-2914.

Danner, Stefan et al. "T7 Phage Display: A Novel Genetic Selection System for Cloning RNA-Binding Proteins from cDNA Libraries" *PNAS* (2001) 98:(23) 12954-12959.

Desai, Prashant et al. "Incorporation of the Green Fluorescent Protein into the Herpes Simplex Virus Type 1 Capsid" *Journal of Virology*, (1998) 72:(9) 7563-7568.

Dmitriev, Igor P. et al. "Engineering of Adenovirus Vectors Containing Heterologous Peptide Sequences in the C Terminus of Capsid Protein IX" *Journal of Virology*, (2002) 76:(14) 6893-6899.

Erlwein, Otto et al. "The Proline-Rich Region of the Ecotropic Maoloney Murine Leukaemia Virus Envelope Protein Tolerates the Insertion of the Green Fluorescent Protein and Allows the Generation of Replication-Competent Virus" *Journal of General Virology*, (2003) 84:369-379.

Hitzman, Ronald et al. "Secretion of Human Interferons by Yeast" *Science* (1983) 219:(4585) 620-625.

Jabbar, Abdul et al. "Signal Processing, Glycosylation, and Secretion of Mutant Hemagglutinins of a Human Influenza Virus by *Saccharomyces cerevisiae*" *Mol. Cell Biol.* (1987) 7:(4) 1476-85.

Kaba, Stephen A. et al. "Baculovirus Surface Display of *Theileria parva* p67 Antigen Preserves the Conformation of Sporozoite Neutralizing Epitopes" *Protein Engineering*, (2003) 16:(1) 73-78.

Li, Lin et al. "Functional Display of Foreign Protein on Surface of *Escherichia coli* Using N-Terminal Domain of Ice Nucleation Protein" *Biotechnology and Bioengineering*, (2004) 85:(2) 214-221.

Ren, Z.J. et al. "Phage Display of Intact Domains at High Copy Number: A System Based on SOC, the Small Outer Capsid Protein of Bacteriophage T4" *Protein Science* (1996) 5:1833-1843.

Sternberg, Nat et al. "Display of Peptides and Proteins on the Surface of Bacteriophage λ" *Proc. Nat. Acad. Sci.* (1995) 92:1609-1613.

Talmadge, Karen et al. "Eukaryotic Signal Sequence Transports Insulin Antigen in *Escherichia coli*." *Proc. Natl. Acad. Sci.* (1980) 77(6):3369-3373.

Wiedmann, M. et al. "Xenopus Oocytes can Secrete Bacterial Beta-Lactamase" *Nature* (1984) 309(5969):637-639.

Zucconi, Adriana et al. "Selection of Ligands by Panning of Domain Libraries Displayed on Phage Lambda Reveals New Potential Partners of Synaptojanin 1" *Journal of Molecular Biology* (2001) 307:1329-1339.

Crameri, R. et al. Cloning aspergillus fumigatus allergens by the pJuFo filamentous phage display system. *International Archives of Allergy and Immunology*. 1996; 110: 41-45.

Palzkill, T. et al. Mapping protein-ligand interactions using whole genome phage display libraries. *Gene—An international Journal on Genes and Genomes*. 1998; 221: 79-83.

Shimazu, M. et al. Cell surface display of organophosphorus hydrolase using ice nucleation protein. *Biotechnology Progress*. 2001; 17(1): 76-80.

Zwick, M. B. et al. Homodimeric peptides displayed by the major coat protein of filamentous phage. *Journal of Molecular Biology*. 2000; 300(2): 307-320.

\* cited by examiner

Gene III leader sequence in KO7 helper phage

GTG AAA AAA TTA TTA TTC GCA ATT CCT TTA GTT GTT CCT TTC TAT TCT CAC TCC GCT
 V   K   K   L   L   F   A   I   P   L   V   V   P   F   Y   S   H   S   A

Gene III leader sequence in KO7kpn helper phage

KpnI
GTG AAA AAA TTA TTA TTC GCA ATT CCT TTA GTG GTA CCT TTC TAT TCT CAC TCC GCT
 V   K   K   L   L   F   A   I   P   L   V   V   P   F   Y   S   H   S   A

Fig. 3B

Map of phagemid vector pABMC6

Helper phage with engineered gene III fused to adaptor 2

GR2-Myc domain coding sequence in GM-UltraHelper phage genome

```
        KpnI      Gene III leader                                    GR2
---TTAGTGGTACCTTTCTATTCTCACTCCGCT ACATCCCGCCTGGAGGGCCTACAGTCAGAAAACCATCGCCTGCGA
-  L  V  V  P  F  Y  S  H  S  A   T  S  R  L  E  G  L  Q  S  E  N  H  R  L  R NotI
ATGAAGATCACAGAGCTGGATAAAGACTTGGAAGAGGTCACCATGCAGCTGCAGGACGTCGGAGGTTGC GCGGCCGCA
 M  K  I  T  E  L  D  K  D  L  E  E  V  T  M  Q  L  Q  D  V  G  G  C   A  A  A Myc-tag                      BglII                  Gene III
GAACAAAAACTCATCTCAGAAGAGGATCTG AGATCTGGAGGCGGT ACTGTTGAAAGTTGTTTAGCAAAA---
 E  Q  K  L  I  S  E  E  D  L   R  S  G  G  G   T  V  E  S  C  L  A  K  -
```

Fig. 5B

Trypsin cleavage sites at GR2-Myc domain on GM-UltraHelper phage

GR2 domain

T S R▲L E G L Q S E N H R▲L R M K▲I T E L D K▲D L E E V

Myc-tag

Complete vector sequence of pABMX14

GCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTCACGGTTCTTTAAGGAGGA
ATTAAAAATGAAATACCTATTGCCTACGGCAGCCGCTGGATTGTTATTACTCGCGGCCCAGCCCGCCTCGTATAATGTGTGGAATTGTGAGCGGATAACAATTTCACACAGGAAACAGCTATGACC
TTGAGAAGGAGAACCGTGAACTGCTGAAAAGATCATTGCTGAGAAAGAGAAGGAGCGTGTCTCTGAACTGCGCCATCCAGTCTGTAGGAGGTTGTAGATCTTATCATACGACTCACAGACTA
CGCAGGAGGTCATCACCATCACCATCACGGATCCTTGCGACCTGGCGTAATAGCGAAGAGGCCCGCACCGATCGCCCTTCCCAACAGTTGCGCAGCCTGAATGGCGAATGGCGCGCCCTGTAG
ACCCAACTTAATCGCCTTGCAGCACATCGCCCCTTTCGCCAGCTGGCGTAATAGCGAAGAGGCCCGCACCGATCGCCCTTCCCAACAGTTGCGCAGCCTGAATGGCGAATGGCGCCTTTCCC
CGGGCATTAAGCGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGGCACCTCGACCCCAAAAACTTGATTAGGGTGATGGTTCACGTAGTGGCCATCGCCCTAGTAGACGGTTTTT
CGCCCTTTGACGTTGGAGTCCACGTTCTTTAATAGTGGACTCTTGTTCCAAACTGGAACAACACTCAACCCTATCTCGGTCTATTCTTTGATTTATAAGGGATTTTGCCGATTTCGGCCTATTG
GTTAAAAAATGAGCTGATTTAACAAAAATTTAACGCGAATTTTAACAAAATATTAACGCTTACAATTTAGGTGCGCGGAACCCCTATTGTTTATTTTTCTAAAT
ACATTCAAATATGTATCCGCTCATGAGACAACAACCCTGAAAGTAAAAGATGCTGAAGATCAGTTGGGTGCACGAGTGGGTTACATCGAACTGGATCTCAACAGCGGTAAGATCTTCTGAGAGTTTTCGC
CCCGAAGAACGTTTTCCAATGATGAGCACTTTTAAAGTTCTGCTATGTGGCGCGGTATTATCCCGTATTGACGCCGGGCAAGAGCAACTCGGTCGCCGCATACACTATTCTCAGAATGACTTGGT
TGAGTACTCACCAGTCACAGAAAAGCATCTTACGGATGGCATGACAGTAAGAGAATTATGCAGTGCTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTTGGGAACCGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACAATTAATAGACTGGATGGAGGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTATCATTGCAGCACTGGGGCCAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGTAACTGTCAGACCAAGTTTACTCATATATACTTTAGATTGATTTAAAACTTCATTTTAATTTAAAAGG
ATCTAGGTGAAGATCCTTTTTGATAATCTCATGACCAAAATCCCTTAACGTGAGTTTTCGTTCCACTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTG
TCCTTCTAGTGTAGCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCGTGCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGGCGGAGCCTATGGAAAAACGCCAGCAACGCGGCCTTTTTACGGTTCCTGGCCTTTTGCTGG
ATGTTCTTTCCTGCGTTATCCCCTGATTCTGTGGATAACCGTATTACCGCCTTTGAGTGAGCTGATACCGCTCGCCGCAGCCGAACGACCGAGCGCAGCGAGTCAGTGAGCGAGGAAGCGAAGA
GCGCCCAATACGCAAACCGCCTCTCCCCGCGCGTTGGCCGATTCATTAATGCAGCTGGCACGACAGGTTTCCCGACTGGAAAGCGGGCAGTGA

Fig. 9B

Map of phagemid vector pABMC13

Engineered gene III sequence in CM phage

```
         KpnI   Gene III leader        Amber stop      NotI              Myc-tag                        BglII
---TTAGTGGTACCTTTCTATTCTCACTCCGCT TAGGCTTGCGGTGGTGCGGCCGCAGAACAAAAACTCATCTCAGAAGAGGATCTGAGATCT AGATCTGGA
 -  L  V  V  P  F  Y  S  H  S  A  *   A  C  G  G   A  A  E  Q  K  L  I  S  E  E  D  L  R  S    R  S  G Gene III
GGCGGT ACTGTTGAAAGTTGTTTAGCAAAACCTCATACAGAAAATTCATTTACTAACGTCTGGAAAGACGACAAAACTTTAGATCGTTACGCT------
 G  G   T  V  E  S  C  L  A  K  P  H  T  E  N  S  F  T  N  V  W  K  D  D  K  T  L  D  R  Y  A  -  -
```

Fig. 13B

Phagemid vector for protein-HA-cys expression

Complete vector sequence of pABMX15

GCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTACGGTTCTTTAACTTTAGTAAGGAGA
ATTAAAAAATGAAATACCTATTGCCTACGGCAGCCGCTGGATTGTTATTACTCGCGCCGCCATGGCGCCCTTCCAGGCCCTTACCCGTACGACGTTCCGGACTACGCAGGTGGCT
GCTGATAAGTCGACCTCGACCAATTCGCCTATAGTGAGTCGTATTACAATTCACTGGCCGTCGTTTTACAACGTCGTGACTGGGAAAACCCTGGCGTTACCCAACTTAATCGCCTTGCAGCACATCCCCCTTC
GCCAGCTGGCGTAATAGCGAAGAGGCCCGCACCGATCGCCCTTCCCAACAGTTGCGCAGCCTGAATGGCGAATGGCGCCTGATGCGGTATTTTCTCCTTACGCATCTGTGCGGTATTTCACACCGCATAT
GCTCACTTGCCAGCGCCCTAGCGCCCGCTCCTTTCGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC
CTCGACCCCAAAAAACTTGATTAGGGTGATGGTTCACGTAGTGGGCCATCGCCCTGATAGACGGTTTTTCGCCCTTTGACGTTGGAGTCACGTTCTTTAATAGTGGACTCTTGTTCCAAACTGGAACAACACTC
AACCCTATCTCGGTCTATTCTTTTGATTTATAAGGGATTTTGCCGATTTCGGCCTATTGGTTAAAAAATGAGCTGATTTAACAAAAATTTAACGCGAATTTTAACAAATATTAACGCTTACAATTTAGGTGGCA
CTTTTCGGGGAAATGTGCGCGGAACCCCTATTTGTTTATTTTTCTAAATACATTCAAATATGTATCCGCTCATGAGACAATAACCCTGATAAATGCTTCAATAATATTGAAAAAGGAAGAGTATGAGTATTCAAC
ATTTCCGTGTCGCCCTTATTCCCTTTTTGCGGCATTTTGCCTTCCTGTTTTGCCACCCAGAAACGCTGGTGAAAGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATGGCATGACAGTAAGAGAATTATGCAGTGCTGCCATAAGAACTGGATCGTTGGGAACCGGAGCTGAATGAAGCCATACCAAACGACGAGCGTGACACCACGATGCCTGTAGCAATGG
TCGGAGGACCGAAGGAGCTAACCGCTTTTTTGCACAACATGGGGGATCATGTAACTCGCCTTGATCGTTGGGAACCGGAGCTGAATGAAGCCATACCAAACGACGAGCGTGACACCACGATGCCTGTAGCAATGG
CAACAACGTTGCGCAAACTATTAACTGGCGAACTACTTACTCTAGCTTCCCGGCAACAATTAATAGACTGGATGGAGGCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGCCAGATGGTAAGCCCTCCCGTATCGTAGTTATCTACACGACGGGGAGTCAGCAACTATGGATGAACGAAATAGACAGA
TCGCTGAGATAGGTGCCTCACTGATTAAGCATTGGTAACTGTCAGACCAAGTTTACTCATATATACTTTAGATTGATTTAAAACTTCATTTTTAATTTAAAAGGATCTAGGTGAAGATCCTTTTTGATAATCTCA
TGACCAAAATCCCTTAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTCAGCAGAGCGCAGATACCAAATACTGTCCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGT
GCACACAGCCCAGCTTGGAGCGAACGACCTACAGCGTGAGCTATGAGAAAGCGCCACGCTTCCCGAAGGGAGAAAGGCGGACAGGTATCCGGTAAGCGGCAGGGTCGGAACAGGAG
AGCGCACGAGGGAGCTTCCAGGGGGAAACGCCTGGTATCTTTATAGTCCTGTCGGGTTTCGCCACCTCTGACTTGAGCGTCGATTTTTGTGATGCTCGTCAGGGGGGCGGAGCCTATGGAAAAACGCCAGCAACG
CGGCCTTTTTACGGTTCCTGGCCTTTTGCTGGCCTTTTGCTCACATGTTCTTTCCTGCGTTATCCCCTGATTCTGTGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTCCCCGCGCGTTGGCCGATTCATTAATGCAGCTGGCACGACAGGTTTCCCGACTGGAAAGCGGGCAGTGA

Fig. 15B

Fig. 17 Detection of scFv displayed by CM-UltraHelper phage

1: KO7 phage; 2: CM phage; 3: pABMx15-AM1/KO7; 4: pABMx15-AM1/CM

Engineered gene III Sequence in GMCT phage genome

```
        KpnI    Gene III Leader                              GR2 domain
---TTAGTGGTACCTTTCTATTCTCACTCCGCT ACATCCCGCCTGGAGGGCCTACAGTCAGAAAACCATCGCTGAATGAAGATCACAGAGCTGGATAAA
 - L V V P F Y S H S A   T S R L E G L Q S E N H R L R M K I T E L D K
                                                              Myc-tag
GACTTGGAAGAGGTCACCATGCAGCTGCAGGACGTGCGGAGGTTGC GCGGCCGCAGAACAAAAACTGATCTCAGAAGAGATCTGACGCGTGCT GGCGGC
 D L E E V T M Q L Q D V G G C   A A A E Q K L I S E E D L T R A   G G
         NotI                         CT domain of Gene III
GGCTCTGGTGGTTCTGGTGGTTCGGGCGGCTCTGAGGGTGGCGGTTCTGAGGGTGGCGGCTCTGAGGGTGGCGGTTCCGGTGGCGGCTCC
 G S G G S G G S G G S E G G G S E G G G S E G G G S G G G G S
GGTTCCGGTGATTTTGATTATGAAAAAATGGCAAACGCTAATAAGGGGGCTATGACCGAAAATGCCGATGAAAACGCGCTACAGTCTGACGCTAAAGGCAAA
 G S G D F D Y E K M A N A N K G A M T E N A D E N A L Q S D A K G K
CTTGATTCTGTCGCTACTGATTACGGTGCTGCTATCGATGGTTTCATTGGTGACGTTTCCGGCCTTGCTAATGGTAATGGTGCTACTGGTGATTTTGCTGGC
 L D S V A T D Y G A A I D G F I G D V S G L A N G N G A T G D F A G
TCTAATTCCCAAATGGCTCAAGTCGGTGACGGTGATAATTCACCTTTAATGAATAATTTCCGTCAATATTACCTTCCCTCCTCCTCAATCGGTTGAATGTCGC
 S N S Q M A Q V G D G D N S P L M N N F R Q Y L P S L P Q S V E C R
CCTTTTGTCTTTGGCGCTGGTAAACCATATGAATTTTCTATTGATTGTGACAAAATAAACTTATTCCGTGGTGTCTTTGCTTTCTTTTATATGTTGCCACC
 P F F G A G K P Y E F S I D C D K I N L F R G V F A F L Y V A T
TTTATGTATGTATTTCTACGTTTGCTAACATACTGCGTAATAAGGAGTCTTAATAA GGCGCGCCACAATTTCACAGTAAGGAGGTTTAATAA ATGAAA
 F M Y V F S T F A N I L R N K E S *   *                               AscI                        BglII     Gene III       M K
OmpA leader                                             s/D
AAGACAGCTATTGCCGATTGCAGTGGCACTGGCTGTTGCGCTACCGTAGCGCAGGCT AGATCTGGAGGCCGGT ACTGTTGAAAGTTGTTTAGCAAAA---
 K T A I A V A L A G F A T V A Q A   R S G G G   T V E S C L A K -
```

Fig. 19B

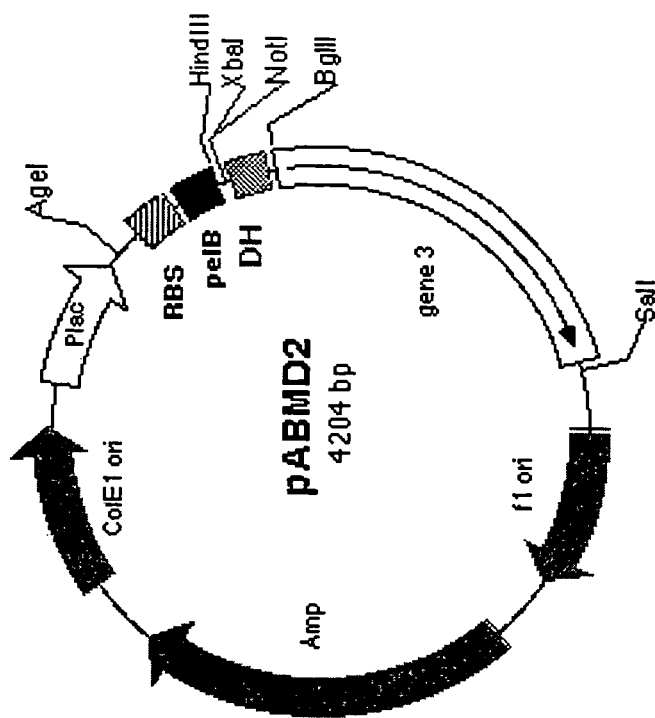
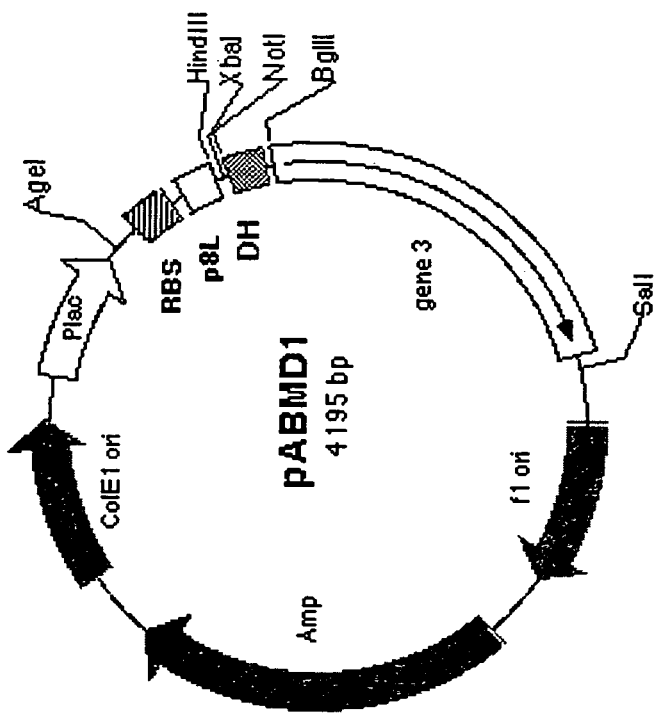
Fig. 22A

PABMD1 vector: sequence from AgeI to SalI

```
           lac promoter/lacO1                         AgeI          EP        S/D
AATTGTGAGCGGATAACAATTT ACCGGT TCTT TTAACTTTAG TAAGGAGG AATTAAAAA
                                                              HindIII      XbaI
ATGAAAAAGTCTTTAGTCCTCAAAGCCTCCGTTGCTACCCTCGTTCCGATGCTAAGCTTCGCT TCTAGA
 M  K  K  S  L  V  L  K  A  S  V  A  V  A  T  L  V  P  M  L  S  F  A     S  R
        P8 Leader                                           HA-tag     Amber stop  BglII
GCGGCCGCT TATCCATACGACGTACCAGACTACGCA GGAGGT CATCACCATCATCACCAT TAG AGATCT
    NotI
 A  A  A  Y  P  Y  D  V  P  D  Y  A    G  G   H  H  H  H  H  H   *    R  S
                                                       His-tag                      SalI
GGAGGCGGT ACTGTTGAAAGTTGTTTAGCAAAA ---- GCTAACATACTGCGTAATAAGGAGTCTTAA GTCGAC
 G  G  G  T  V  E  S  C  L  A  K  ----  A  N  I  L  R  N  K  E  S   *
                Gene 3
```

PABMD2 vector: sequence from AgeI to SalI

```
           lac promoter/lacO1                         AgeI          EP        S/D
AATTGTGAGCGGATAACAATTT ACCGGT TCTT TTAACTTTAG TAAGGAGG AATTAAAAA
                                                                NcoI            PstI        XbaI
ATGAAATATCTATTGCCTACGGCCTGCTGATTGTTATTACTCGCGGCCCAGCCGGCCATGGCGGCCCTGCAGGCCTCTAGA
 M  K  Y  L  L  P  T  A  A  A  G  L  L  L  L  A  A  Q  P  A  M  A  A  L  Q  A  S  R
        pelB Leader                                            HA-tag       Amber stop  BglII
GCGGCCGCT TATCCATACGACGTACCAGACTACGCA GGAGGT CATCACCATCATCACCAT TAG AGATCT
    NotI
 A  A  A  Y  P  Y  D  V  P  D  Y  A    G  G   H  H  H  H  H  H   *    R  S
                                                       His-tag                      SalI
GGAGGCGGT ACTGTTGAAAGTTGTTTAGCAAAA ---- GCTAACATACTGCGTAATAAGGAGTCTTAA GTCGAC
 G  G  G  T  V  E  S  C  L  A  K  ----  A  N  I  L  R  N  K  E  S   *
                Gene 3
```

Fig. 22B

GR1 Sequence Range: 1 to 146

```
         XbaI      10          20          30          40          50
         TCTAGAGGTGGAGGAGGTGAGGAGGAGAAGTCCCGGCTGTTGGAGAAGGAGAA
          S  R  G  G  G  G  E  E  K  S  R  L  L  E  K  E  N
                      60          70          80          90         100
         CCGTGAACTGGAAAAGATCATTGCTGAGAAAGAGAGCGTGTCTCTGAAC
          R  E  L  E  K  I  I  A  E  K  E  R  V  S  E
                     110         120         130        140  AscI
         TGCGCCATCAACTCCAGTCTGTAGGAGGTTGTTAATAGGGCGCGCC
          L  R  H  Q  L  Q  S  V  G  G  C  *  *
```

GR2 Sequence Range: 1 to 140

```
         XhoI      10          20          30          40          50
         TCTCGAGGAGGTGGTGGAACATCCCGCCTGGAGGGCCTACAGTCAGAAAA
          S  R  G  G  G  G  T  S  R  L  E  G  L  Q  S  E  N
                      60          70          80          90         100
         CCATCGCCTGCGAATGAAGATCACAGAGCTGGATAAAGACTTGGAAGAGG
          H  R  L  R  M  K  I  T  E  L  D  K  D  L  E  E
                     110         120         130  NotI  140
         TCACCATGCAGCTGCAGGACGTCGGAGGTTGCGCGGCCGC
          V  T  M  Q  L  Q  D  V  G  G  C  A  A  A
```

Fig. 23

Complete vector sequence of pABMX22

GCGCAACGCAATTAATGTGAGTTAGCTCACTCATTAGGCACCCCAGGCTTTACACTTTATGCTTCCGGCTCGTATGTTGTGTGGAATTGTGAGCGGATAACAATTTCACGGTTCTTTAAGAGGAATT
AAAAATGAAAAAGTCTTAGTCCTCAAAGCCTCCGTAGCCGTTGCTACCCTCGTTCCGATGCTAAGCTTCCGATGTTGGTGAAAGTCCCGTCTGCTGGTGAAAGAGAACCGTGAACTGGAAAAGATC
ATTGCTGAGAAAGAGGAGCGTGTTTCTGAACTGCCATCAACTGCGTTCTAGAGCGGTTCACGCGTTCACGCGTTCTAGAGCGGTTCACCCGGTACGGACTACGTCCGATAAGTCGACCTCGA
CCAATTCGCCCTATAGTGAGTCGTATTACAATTCACTGGCCGTCGTTTTACAACGTCGTGACTGGGAAAACCCTGGCGTTACCCAACTTAATCGCCTTGCAGCACATCCCCCTTTCGCCAGCTGGCGT
AATAGCGAAGAGGCCCGCACCGATCGCCCTTCCCAACAGTTGCGCAGCCTGAATGGCGAGCGGCTTTCCCGGCTTTCGCCCAAGCTCTAAATCGGGGGCATCCCTTTAGGGTTCCGATTTAGTGCTTTACGGC
ACCTCGACCCCAAAAAACTTGATTAGGGTGATGGTTCACGTAGTGGGCCATCGCCCTGATAGACGGTTTTCGCCCTTTCGGTCTTAATAGCTGATTTAACAAAATTAACGCGAATTTAACAAAATATTAACGCT
ACAACACTCAACCCTATCTCGGTCTATTCTTTTGATTTATAAGGGATTTTGCCGATTTCGGCCTATTGGTTAAAAAATGAGCTGATTTAACAAAAATTTACGCGAATTTAACAAAATATTAACGCT
TACAATTTAGGTGGCACTTTTCGGGGAAATGTGCGCGGAACCCCTATTTGTTATTTTTCTAAATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTTGCCTTCCTGTTTTTGCTCACCCAGAAACGCTGGTGAAAGTAAAAGATGCTGAAGATCAGTTGGGTG
CACGAGTGGGTTACATCGAACTGGATCTCAACAGCGGTAAGATCCTTGAGAGTTTTCGCCCCGAAGAACGTTTTCCAATGATGAGCACTTTTAAAGTTCTGCTATGGCGGTATTATCCGTATT
GACGCCGGGCAAGAGCAACTCGGTCGCCGCATACACTATTCTCAGAATGACTTGGTTGAGTACTCACCAGTCACAGAAAAGCATCTTACGGATGGCATGACAGTAAGAGAATTATGCAGTGCTGCCAT
AACCATGAGTGATAACACTGCGGCCAACTTACTTCTGACAACGATCGGAGGACCGAAGGAGCTAACCGCTTTTTTGCACAACATGGGGGATCATGTAACTCGCCTTGATCGTTGGGAACCGGAGCTGA
ATGAAGCCATACCAAACGACGAGCGTGACACCACGATGCCTGTAGCAATGGCAACAACGTTGCGCAAACTATTAACTGGCGAACTACTTACTCTAGCTTCCCGGCGTCAAATAATGGAGCCGGTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAGTTTACTCATATA
TACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCAGACCCCGTAGAA
AAGATCAAAGGATCTCTTGAGATCCTTTTTTTCTGCGCGTAATCTGCTGCTTGCAAACAAAAAAACCACCGCTACCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCGTAGTTAGGCCACCACTTCAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGATAAGGCGCAGCGGTCGGGCTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAGGGAGAAAGGCGGACAGGTATCCGGTAAGCGGCAGGGTCGGAACAGGAGAGCGCACGAGGGAGCTTCCAGGGGAAA
CGCCTGGTATCTTTATAGTCCTGTCGGGTTTCGCCACCTCTGACTTGAGCGTCGATTTTTGTGATGCTCGTCAGGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCGCGCGTTGGCCGATTCATTAATGCAGCTGGCACGACAGGTTTCCCGACTGGAAAGCGGGCAGTGA

Fig. 25B

Helper vector for adapter-directed bacterial display

Complete vector sequence of pABMXbd-1

```
GCGAACGCAATTAATGTGAGTTAGCTCACTCATTAGGCACCCCAGGCTTTACACTTTATGCTTCCGGCTCGTATGTTGTGTGGAATTGTGAGCGGATAACAATTTCACACAGGAAACAGCTATGACCA
TGATTACGCCAAGCGCGTTTAACTTTAGTAAGGAGAATTAAAAATGAAATACCTGCTGCCGACCGCTGCTGCTGCTGTTACTGGCGGCCCAGCCGGCTATGCGCGGGTATGAAGCTACTAAACTG
GTACTGGGCAACCCGTATGTTGGCTTTGAAATGGGTACGACTGGTTAGGTCGTATGCCGTACAAAGGCAGGTTGAAAACGTGCATACAAACCACGACACCGGGCGTTTCTCCGGTCTTCGCGTGTTGAG
CCAATCACTGACGACCTGGACATCGTACACCCGTCTGGGTGGCATGGTGGGCTCTGGGTGGCAGATACCAGTGGACGACAACATCGGCACTCGTCCCGACGGAGGTACATCCGCCTGGAGGGCTACAGTCAGAAAC
TACGCGATCACTCTGCGAATGAAGATCACAGAGTCTGGATAAAGACTTGGAAGAAGTACCATGGAAGAGCGTTGGCGGTTGCACTGTCTAATGACGTCCCAACAGTTGCGCAGCCTGCGAATGGGACGCG
AACCCTGGCGTTACCCAACTTAATCGCCTTAATCGCCTTCGCAGCACATCCCCGTTTCGCCAGTGGCGTAATAGCGAAGAGGCCCGCACCGATCGCCCTTCCCAACAGTTGCGCAGCCTGAATGGCGAATGGCGC
CCCTGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCGCCGGCTTT
CCCCGTCAAGCTCTAAATCGGGGGCTCCCTTTAGGGTTCCGATTTAGTGCTTTACGGCACCTCGACCCCAAAAAACTTGATTAGGGTGATGGTTCACGTAGTGGGCCATCGCCCTGATAGACGGTTTT
CGCCCTTTGACGTTGGAGTCCACGTTCTTTAATAGTGGACTCTTGTTCCAAACTGGAACAACACTCAACCCTATCTCGGTCTATTCTTTTGATTTATAAGGGATTTTGCCGATTTCGGCCTATTGGTTA
AAAAATGAGCTGATTTAACAAAAATTTAACGCGAATTTAACAAATATTAACGCTTACAAAATATTAACGTTTACAATTTTATGGCACTTTTCGGGGAAATGTGCGCGGAACCCCTATTTGTTTATTTTTCTAAATACATTCAA
ATATGTATCCGCTCATGAGACAATAACCCTGATAAATGCTTCAATAATATTGAAAAAGGAAGAGTATTGGGTGCACAGCTGGGTTACATCGAACTGGATCTCAACAGCGGTAAGATCCTTGAGAGTTTTCGCCCCGAAGAACGTTTTC
CAATGATGAGCACTTTTAAAGTTCTGCTATGTGGCGCGGTATTATCCCGTATTGACGCCGGGCAAGAGCAACTCGGTCGCCGCATACACTATTCTCAGAATGACTTGGTTGAGTACTCACCAGTCACAGAAAAGCATCTTACGGATGGCATGACAGTAAGAGAATTATGCAGTGCTGCCATAACCATGAGTGATAACACTGCGGCCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGCCATACCAAACGACGAGCGTGACACCACGATGCCTGTAGCAATGGCAACAACGTTGCGCAAACTATTAACTGGCGAACTACTTACTCTAGCTTCCCGGCAACAATTAATAGACTGGATGGAGGCGGATAAAGTTGCAGGACCACTTCTGCGCTCGGCCCTTCCGGCTGGCTGGTTTATTGCTGATAAATCTGGAGCCGGTGAGCGTGGGTCTCGCGGTATCATTGCAGCACTGGGGCCAGATGGTAAGCCCTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAGTTTACTCATATATACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTGTTCTTCTAGTGTAGCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGTGCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGTCGGGTTTCGCC
ACCTCTGACTTGAGCGTCGATTTTTGTGATGCTCGTCAGGGGGGCGGAGCCTATGGAAAAACGCCAGCAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCGCCGCAGCCGAACGACCGAGCGCAGCGAGTCAGTGAGCGAGGAAGCGGAAGAGCGCCCAATACGCAAAC
CGCCTCTCCCCGCGCGTTGGCCGATTCATTAATGCAGCTGGCACGACAGGTTTCCCGACTGGAAAGCGGGCAGTGA
```

Fig. 26B

```
                        SEQUENCE LISTING

<160> NUMBER OF SEQ ID NOS: 31

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      nucleotide leader sequence
<220> FEATURE:
<221> NAME/KEY: CDS
<222> LOCATION: (1)..(57)

<400> SEQUENCE: 1 gtg aaa aaa tta tta ttc gca att cct tta gtt gtt cct ttc tat tct      48
Val Lys Lys Leu Leu Phe Ala Ile Pro Leu Val Val Pro Phe Tyr Ser
  1               5                  10                  15 cac tcc gct                                                          57
His Ser Ala <210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      amino acid leader sequence

<400> SEQUENCE: 2

Val Lys Lys Leu Leu Phe Ala Ile Pro Leu Val Val Pro Phe Tyr Ser
  1               5                  10                  15

His Ser Ala

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      nucleotide leader sequence
<220> FEATURE:
<221> NAME/KEY: CDS
<222> LOCATION: (1)..(57)

<400> SEQUENCE: 3 gtg aaa aaa tta tta ttc gca att cct tta gtg gta cct ttc tat tct      48
Val Lys Lys Leu Leu Phe Ala Ile Pro Leu Val Val Pro Phe Tyr Ser
  1               5                  10                  15 cac tcc gct                                                          57
His Ser Ala <210> SEQ ID NO 4
<211> LENGTH: 222
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(222)
```

<400> SEQUENCE: 4

```
tta gtg gta cct ttc tat tct cac tcc gct aca tcc cgc ctg gag ggc      48
Leu Val Val Pro Phe Tyr Ser His Ser Ala Thr Ser Arg Leu Glu Gly
 1               5                  10                  15 cta cag tca gaa aac cat cgc ctg cga atg aag atc aca gag ctg gat      96
Leu Gln Ser Glu Asn His Arg Leu Arg Met Lys Ile Thr Glu Leu Asp
            20                  25                  30 aaa gac ttg gaa gag gtc acc atg cag ctg cag gac gtc gga ggt tgc     144
Lys Asp Leu Glu Glu Val Thr Met Gln Leu Gln Asp Val Gly Gly Cys
        35                  40                  45 gcg gcc gca gaa caa aaa ctc atc tca gaa gag gat ctg aga tct gga     192
Ala Ala Ala Glu Gln Lys Leu Ile Ser Glu Glu Asp Leu Arg Ser Gly
    50                  55                  60 ggc ggt act gtt gaa agt tgt tta gca aaa                              222
Gly Gly Thr Val Glu Ser Cys Leu Ala Lys
65                  70
```

<210> SEQ ID NO 5
<211> LENGTH: 74
<212> TYPE: PRT
<213> ORGANISM: Artificial Sequence
<220> FEATURE:
<223> OTHER INFORMATION: Description of Artificial Sequence: Synthetic amino acid sequence

<400> SEQUENCE: 5

```
Leu Val Val Pro Phe Tyr Ser His Ser Ala Thr Ser Arg Leu Glu Gly
 1               5                  10                  15

Leu Gln Ser Glu Asn His Arg Leu Arg Met Lys Ile Thr Glu Leu Asp
            20                  25                  30

Lys Asp Leu Glu Glu Val Thr Met Gln Leu Gln Asp Val Gly Gly Cys
        35                  40                  45

Ala Ala Ala Glu Gln Lys Leu Ile Ser Glu Glu Asp Leu Arg Ser Gly
    50                  55                  60

Gly Gly Thr Val Glu Ser Cys Leu Ala Lys
65                  70
```

<210> SEQ ID NO 6
<211> LENGTH: 56
<212> TYPE: PRT
<213> ORGANISM: Artificial Sequence
<220> FEATURE:
<223> OTHER INFORMATION: Description of Artificial Sequence: Synthetic amino acid sequence

<400> SEQUENCE: 6

```
Thr Ser Arg Leu Glu Gly Leu Gln Ser Glu Asn His Arg Leu Arg Met
 1               5                  10                  15

Lys Ile Thr Glu Leu Asp Lys Asp Leu Glu Glu Val Thr Met Gln Leu
            20                  25                  30

Gln Asp Val Gly Gly Cys Ala Ala Ala Glu Gln Lys Leu Ile Ser Glu
        35                  40                  45

Glu Asp Leu Arg Ser Gly Gly Gly
    50                  55
```

<210> SEQ ID NO 7
<211> LENGTH: 3093
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 7

```
gcgcaacgca attaatgtga gttagctcac tcattaggca ccccaggctt tacactttat     60
gcttccggct cgtatgttgt gtggaattgt gagcggataa caatttaccg gttctttaag    120
gaggaattaa aaaatgaaat acctattgcc tacggcagcc gctggattgt tattactcgc    180
ggcccagccg gccatggcgg ccctgcaggc ctctagagcg gccgctggag gtgaggagaa    240
gtcccggctg ttggagaagg agaaccgtga actggaaaag atcattgctg agaaagagga    300
gcgtgtctct gaactgcgcc atcaactcca gtctgtagga ggttgtagat cttatccata    360
cgacgtacca gactacgcag gaggtcatca ccatcatcac cattaatgag tcgacctcga    420
ccaattcgcc ctatagtgag tcgtattaca attcactggc cgtcgtttta caacgtcgtg    480
actgggaaaa ccctggcgtt acccaactta atcgccttgc agcacatccc ctttcgcca     540
gctggcgtaa tagcgaagag gcccgcaccg atcgccctc caacagttg cgcagcctga      600
atggcgaatg ggacgcgccc tgtagcggcg cattaagcgc ggcgggtgtg gtggttacgc    660
gcagcgtgac cgctacactt gccagcgccc tagcgcccgc tcctttcgct ttcttccctt    720
cctttctcgc cacgttcgcc ggctttcccc gtcaagctct aaatcggggg ctccctttag    780
ggttccgatt tagtgcttta cggcacctcg acccccaaaaa acttgattag ggtgatggtt    840
cacgtagtgg gccatcgccc tgatagacgg ttttttcgccc tttgacgttg gagtccacgt    900
tctttaatag tggactcttg ttccaaactg gaacaacact caaccctatc tcggtctatt    960
cttttgattt ataagggatt ttgccgattt cggcctattg gttaaaaaat gagctgattt   1020
aacaaaaatt taacgcgaat tttaacaaaa tattaacgct tacaatttag gtggcacttt   1080
tcggggaaat gtgcgcggaa cccctatttg tttatttttc taaatacatt caaatatgta   1140
tccgctcatg agacaataac cctgataaat gcttcaataa tattgaaaaa ggaagagtat   1200
gagtattcaa catttccgtg tcgcccttat tcccttttt gcggcatttt gccttcctgt   1260
ttttgctcac ccagaaacgc tggtgaaagt aaaagatgct gaagatcagt tgggtgcacg   1320
agtgggttac atcgaactgg atctcaacag cggtaagatc cttgagagtt ttcgccccga   1380
agaacgtttt ccaatgatga gcacttttaa agttctgcta tgtggcgcgg tattatcccg   1440
tattgacgcc gggcaagagc aactcggtcg ccgcatacac tattctcaga atgacttggt   1500
tgagtactca ccagtcacag aaaagcatct tacggatggc atgacagtaa gagaattatg   1560
cagtgctgcc ataaccatga gtgataacac tgcggccaac ttacttctga acgatcgg     1620
aggaccgaag gagctaaccg cttttttgca acatgggg gatcatgtaa ctcgccttga    1680
tcgttgggaa ccggagctga atgaagccat accaaacgac gagcgtgaca ccacgatgcc   1740
tgtagcaatg gcaacaacgt tgcgcaaact attaactggc gaactactta ctctagcttc   1800
ccggcaacaa ttaatagact ggatggaggc ggataaagtt gcaggaccac ttctgcgctc   1860
ggcccttccg gctggctggt ttattgctga taaatctgga gccggtgagc gtgggtctcg   1920
cggtatcatt gcagcactgg ggccagatgg taagccctcc cgtatcgtag ttatctacac   1980
gacgggagt caggcaacta tggatgaacg aaatagacag atcgctgaga taggtgcctc   2040
actgattaag cattggtaac tgtcagacca agtttactca tatatacttt agattgattt   2100
aaaacttcat ttttaattta aaaggatcta ggtgaagatc cttttttgata atctcatgac   2160
caaaatccct taacgtgagt tttcgttcca ctgagcgtca gaccccgtag aaaagatcaa   2220
aggatcttct tgagatcctt ttttttctgcg cgtaatctgc tgcttgcaaa caaaaaaacc   2280
accgctacca gcggtggttt gtttgccgga tcaagagcta ccaactcttt ttccgaaggt   2340
```

-continued

```
aactggcttc agcagagcgc agataccaaa tactgtcctt ctagtgtagc cgtagttagg    2400
ccaccacttc aagaactctg tagcaccgcc tacatacctc gctctgctaa tcctgttacc    2460
agtggctgct gccagtggcg ataagtcgtg tcttaccggg ttggactcaa gacgatagtt    2520
accggataag gcgcagcggt cgggctgaac gggggggttcg tgcacacagc ccagcttgga    2580
gcgaacgacc tacaccgaac tgagatacct acagcgtgag ctatgagaaa gcgccacgct    2640
tcccgaaggg agaaaggcgg acaggtatcc ggtaagcggc agggtcggaa caggagagcg    2700
cacgagggag cttccagggg gaaacgcctg gtatctttat agtcctgtcg ggtttcgcca    2760
cctctgactt gagcgtcgat ttttgtgatg ctcgtcaggg gggcggagcc tatggaaaaa    2820
cgccagcaac gcggcctttt tacggttcct ggccttttgc tggccttttg ctcacatgtt    2880
ctttcctgcg ttatcccctg attctgtgga taaccgtatt accgcctttg agtgagctga    2940
taccgctcgc cgcagccgaa cgaccgagcg cagcgagtca gtgagcgagg aagcggaaga    3000
gcgcccaata cgcaaaccgc ctctccccgc gcgttggccg attcattaat gcagctggca    3060
cgacaggttt cccgactgga aagcgggcag tga                                 3093
```

<210> SEQ ID NO 8
<211> LENGTH: 192
<212> TYPE: DNA
<213> ORGANISM: Artificial Sequence
<220> FEATURE:
<223> OTHER INFORMATION: Description of Artificial Sequence: Synthetic vector sequence
<220> FEATURE:
<221> NAME/KEY: CDS
<222> LOCATION: (1)..(192)

<400> SEQUENCE: 8

```
tta gtg gta cct ttc tat tct cac tcc gct tag gct tgc ggt ggt gcg      48
Leu Val Val Pro Phe Tyr Ser His Ser Ala Gln Ala Cys Gly Gly Ala
 1               5                  10                  15 gcc gca gaa caa aaa ctc atc tca gaa gag gat ctg aga tct aga tct      96
Ala Ala Glu Gln Lys Leu Ile Ser Glu Glu Asp Leu Arg Ser Arg Ser
                20                  25                  30 gga ggc ggt act gtt gaa agt tgt tta gca aaa cct cat aca gaa aat     144
Gly Gly Gly Thr Val Glu Ser Cys Leu Ala Lys Pro His Thr Glu Asn
        35                  40                  45 tca ttt act aac gtc tgg aaa gac gac aaa act tta gat cgt tac gct     192
Ser Phe Thr Asn Val Trp Lys Asp Asp Lys Thr Leu Asp Arg Tyr Ala
    50                  55                  60
```

<210> SEQ ID NO 9
<211> LENGTH: 64
<212> TYPE: PRT
<213> ORGANISM: Artificial Sequence
<220> FEATURE:
<223> OTHER INFORMATION: Description of Artificial Sequence: Synthetic vector sequence
<220> FEATURE:
<221> NAME/KEY: MOD_RES
<222> LOCATION: (11)
<223> OTHER INFORMATION: May be Gln or a true stop codon

<400> SEQUENCE: 9

```
Leu Val Val Pro Phe Tyr Ser His Ser Ala Gln Ala Cys Gly Gly Ala
 1               5                  10                  15

Ala Ala Glu Gln Lys Leu Ile Ser Glu Glu Asp Leu Arg Ser Arg Ser
                20                  25                  30

Gly Gly Gly Thr Val Glu Ser Cys Leu Ala Lys Pro His Thr Glu Asn
        35                  40                  45
```

Ser Phe Thr Asn Val Trp Lys Asp Asp Lys Thr Leu Asp Arg Tyr Ala
    50                  55                  60

<210> SEQ ID NO 10
<211> LENGTH: 2961
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 10

| | | | | | |
|---|---|---|---|---|---|
| gcgcaacgca | attaatgtga | gttagctcac | tcattaggca | ccccaggctt | tacactttat | 60 |
| gcttccggct | cgtatgttgt | gtggaattgt | gagcggataa | caatttaccg | gttcttttaa | 120 |
| ctttagtaag | gaggaattaa | aaaatgaaat | acctattgcc | tacggcagcc | gctggattgt | 180 |
| tattactcgc | ggcccagccg | gccatggcgg | ccctgcaggc | ctctagagcg | gccgcttacc | 240 |
| cgtacgacgt | tccggactac | gcaggtggct | gctgataagt | cgacctcgac | caattcgccc | 300 |
| tatagtgagt | cgtattacaa | ttcactggcc | gtcgttttac | aacgtcgtga | ctgggaaaac | 360 |
| cctggcgtta | cccaacttaa | tcgccttgca | gcacatcccc | ctttcgccag | ctggcgtaat | 420 |
| agcgaagagg | cccgcaccga | tcgcccttcc | caacagttgc | gcagcctgaa | tggcgaatgg | 480 |
| gacgcgccct | gtagcggcgc | attaagcgcg | gcgggtgtgg | tggttacgcg | cagcgtgacc | 540 |
| gctacacttg | ccagcgccct | agcgcccgct | cctttcgctt | tcttcccttc | ctttctcgcc | 600 |
| acgttcgccg | gctttccccg | tcaagctcta | aatcgggggc | tccctttagg | gttccgattt | 660 |
| agtgctttac | ggcacctcga | ccccaaaaaa | cttgattagg | gtgatggttc | acgtagtggg | 720 |
| ccatcgccct | gatagacggt | ttttcgccct | ttgacgttgg | agtccacgtt | ctttaatagt | 780 |
| ggactcttgt | tccaaactgg | aacaacactc | aaccctatct | cggtctattc | ttttgattta | 840 |
| taagggattt | tgccgatttc | ggcctattgg | ttaaaaaatg | agctgattta | acaaaaattt | 900 |
| aacgcgaatt | ttaacaaaat | attaacgctt | acaatttagg | tggcactttt | cggggaaatg | 960 |
| tgcgcggaac | ccctatttgt | ttatttttct | aaatacattc | aaatatgtat | ccgctcatga | 1020 |
| gacaataacc | ctgataaatg | cttcaataat | attgaaaaag | gaagagtatg | agtattcaac | 1080 |
| atttccgtgt | cgcccttatt | ccctttttttg | cggcattttg | ccttcctgtt | tttgctcacc | 1140 |
| cagaaacgct | ggtgaaagta | aaagatgctg | aagatcagtt | gggtgcacga | gtgggttaca | 1200 |
| tcgaactgga | tctcaacagc | ggtaagatcc | ttgagagttt | tcgccccgaa | gaacgttttc | 1260 |
| caatgatgag | cacttttaaa | gttctgctat | gtggcgcggt | attatcccgt | attgacgccg | 1320 |
| ggcaagagca | actcggtcgc | cgcatacact | attctcagaa | tgacttggtt | gagtactcac | 1380 |
| cagtcacaga | aaagcatctt | acggatggca | tgacagtaag | agaattatgc | agtgctgcca | 1440 |
| taaccatgag | tgataacact | gcggccaact | tacttctgac | aacgatcgga | ggaccgaagg | 1500 |
| agctaaccgc | ttttttgcac | aacatggggg | atcatgtaac | tcgccttgat | cgttgggaac | 1560 |
| cggagctgaa | tgaagccata | ccaaacgacg | agcgtgacac | cacgatgcct | gtagcaatgg | 1620 |
| caacaacgtt | gcgcaaacta | ttaactggcg | aactacttac | tctagcttcc | cggcaacaat | 1680 |
| taatagactg | gatggaggcg | gataaagttg | caggaccact | tctgcgctcg | gcccttccgg | 1740 |
| ctggctggtt | tattgctgat | aaatctggag | ccggtgagcg | tgggtctcgc | ggtatcattg | 1800 |
| cagcactggg | gccagatggt | aagccctccc | gtatcgtagt | tatctacacg | acggggagtc | 1860 |
| aggcaactat | ggatgaacga | aatagacaga | tcgctgagat | aggtgcctca | ctgattaagc | 1920 |
| attggtaact | gtcagaccaa | gtttactcat | atatacttta | gattgattta | aaacttcatt | 1980 |

-continued

```
tttaatttaa aaggatctag gtgaagatcc tttttgataa tctcatgacc aaaatccctt    2040
aacgtgagtt ttcgttccac tgagcgtcag accccgtaga aaagatcaaa ggatcttctt    2100
gagatccttt ttttctgcgc gtaatctgct gcttgcaaac aaaaaaacca ccgctaccag    2160
cggtggtttg tttgccggat caagagctac caactctttt tccgaaggta actggcttca    2220
gcagagcgca gataccaaat actgtccttc tagtgtagcc gtagttaggc caccacttca    2280
agaactctgt agcaccgcct acatacctcg ctctgctaat cctgttacca gtggctgctg    2340
ccagtggcga taagtcgtgt cttaccgggt tggactcaag acgatagtta ccggataagg    2400
cgcagcggtc gggctgaacg gggggttcgt gcacacagcc cagcttggag cgaacgacct    2460
acaccgaact gagatacctg cagcgtgagc tatgagaaag cgccacgctt cccgaaggga    2520
gaaaggcgga caggtatccg gtaagcggca gggtcggaac aggagagcgc acgagggagc    2580
ttccaggggg aaacgcctgg tatctttata gtcctgtcgg gtttcgccac ctctgacttg    2640
agcgtcgatt tttgtgatgc tcgtcagggg gcggagcct atggaaaaac gccagcaacg    2700 cggcctttt acggttcctg gccttttgct ggccttttgc tcacatgttc tttcctgcgt    2760
tatcccctga ttctgtggat aaccgtatta ccgccttgag tgagctgata ccgctcgccg    2820
cagccgaacg accgagcgca gcgagtcagt gagcgaggaa gcggaagagc gcccaatacg    2880
caaaccgcct ctccccgcgc gttggccgat tcattaatgc agctggcacg acaggtttcc    2940
cgactggaaa gcgggcagtg a                                              2961
```

<210> SEQ ID NO 11
<211> LENGTH: 903
<212> TYPE: DNA
<213> ORGANISM: Artificial Sequence
<220> FEATURE:
<223> OTHER INFORMATION: Description of Artificial Sequence: Synthetic vector sequence
<220> FEATURE:
<221> NAME/KEY: CDS
<222> LOCATION: (1)..(759)
<220> FEATURE:
<221> NAME/KEY: CDS
<222> LOCATION: (802)..(903)

<400> SEQUENCE: 11

```
tta gtg gta cct ttc tat tct cac tcc gct aca tcc cgc ctg gag ggc     48
Leu Val Val Pro Phe Tyr Ser His Ser Ala Thr Ser Arg Leu Glu Gly
  1               5                  10                  15 cta cag tca gaa aac cat cgc ctg cga atg aag atc aca gag ctg gat    96
Leu Gln Ser Glu Asn His Arg Leu Arg Met Lys Ile Thr Glu Leu Asp
             20                  25                  30 aaa gac ttg gaa gag gtc acc atg cag ctg cag gac gtc gga ggt tgc   144
Lys Asp Leu Glu Glu Val Thr Met Gln Leu Gln Asp Val Gly Gly Cys
         35                  40                  45 gcg gcc gca gaa caa aaa ctg atc tca gaa gag gat ctg acg cgt gct   192
Ala Ala Ala Glu Gln Lys Leu Ile Ser Glu Glu Asp Leu Thr Arg Ala
     50                  55                  60 ggc ggc ggc tct ggt ggt ggt tct ggt ggc ggc tct gag ggt ggc ggc   240
Gly Gly Gly Ser Gly Gly Gly Ser Gly Gly Gly Ser Glu Gly Gly Gly
 65                  70                  75                  80 tct gag ggt ggc ggt tct gag ggt ggc ggc tct gag ggt ggc ggt tcc   288
Ser Glu Gly Gly Gly Ser Glu Gly Gly Gly Ser Glu Gly Gly Gly Ser
                 85                  90                  95 ggt ggc ggc tcc ggt tcc ggt gat ttt gat tat gaa aaa atg gca aac   336
Gly Gly Gly Ser Gly Ser Gly Asp Phe Asp Tyr Glu Lys Met Ala Asn
            100                 105                 110 gct aat aag ggg gct atg acc gaa aat gcc gat gaa aac gcg cta cag   384
Ala Asn Lys Gly Ala Met Thr Glu Asn Ala Asp Glu Asn Ala Leu Gln
```

```
                 Ala Asn Lys Gly Ala Met Thr Glu Asn Ala Asp Glu Asn Ala Leu Gln
                             115                 120                 125 tct gac gct aaa ggc aaa ctt gat tct gtc gct act gat tac ggt gct      432
Ser Asp Ala Lys Gly Lys Leu Asp Ser Val Ala Thr Asp Tyr Gly Ala
        130                 135                 140 gct atc gat ggt ttc att ggt gac gtt tcc ggc ctt gct aat ggt aat      480
Ala Ile Asp Gly Phe Ile Gly Asp Val Ser Gly Leu Ala Asn Gly Asn
145                 150                 155                 160 ggt gct act ggt gat ttt gct ggc tct aat tcc caa atg gct caa gtc      528
Gly Ala Thr Gly Asp Phe Ala Gly Ser Asn Ser Gln Met Ala Gln Val
                165                 170                 175 ggt gac ggt gat aat tca cct tta atg aat aat ttc cgt caa tat tta      576
Gly Asp Gly Asp Asn Ser Pro Leu Met Asn Asn Phe Arg Gln Tyr Leu
            180                 185                 190 cct tcc ctc cct caa tcg gtt gaa tgt cgc cct ttt gtc ttt ggc gct      624
Pro Ser Leu Pro Gln Ser Val Glu Cys Arg Pro Phe Val Phe Gly Ala
        195                 200                 205 ggt aaa cca tat gaa ttt tct att gat tgt gac aaa ata aac tta ttc      672
Gly Lys Pro Tyr Glu Phe Ser Ile Asp Cys Asp Lys Ile Asn Leu Phe
    210                 215                 220 cgt ggt gtc ttt gcg ttt ctt tta tat gtt gcc acc ttt atg tat gta      720
Arg Gly Val Phe Ala Phe Leu Leu Tyr Val Ala Thr Phe Met Tyr Val
225                 230                 235                 240 ttt tct acg ttt gct aac ata ctg cgt aat aag gag tct taataaggcg      769
Phe Ser Thr Phe Ala Asn Ile Leu Arg Asn Lys Glu Ser
                245                 250 cgccacaatt tcacagtaag gaggtttaat aa atg aaa aag aca gct att gcg      822
                                   Met Lys Lys Thr Ala Ile Ala
                                       255                 260 att gca gtg gca ctg gct ggt ttc gct acc gta gcg cag gct aga tct      870
Ile Ala Val Ala Leu Ala Gly Phe Ala Thr Val Ala Gln Ala Arg Ser
                265                 270                 275 gga ggc ggt act gtt gaa agt tgt tta gca aaa                          903
Gly Gly Gly Thr Val Glu Ser Cys Leu Ala Lys
            280                 285

<210> SEQ ID NO 12
<211> LENGTH: 253
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 12

Leu Val Val Pro Phe Tyr Ser His Ser Ala Thr Ser Arg Leu Glu Gly
 1               5                  10                  15

Leu Gln Ser Glu Asn His Arg Leu Arg Met Lys Ile Thr Glu Leu Asp
            20                  25                  30

Lys Asp Leu Glu Glu Val Thr Met Gln Leu Gln Asp Val Gly Gly Cys
        35                  40                  45

Ala Ala Ala Glu Gln Lys Leu Ile Ser Glu Glu Asp Leu Thr Arg Ala
    50                  55                  60

Gly Gly Gly Ser Gly Gly Gly Ser Gly Gly Gly Ser Glu Gly Gly Gly
65                  70                  75                  80

Ser Glu Gly Gly Gly Ser Glu Gly Gly Gly Ser Glu Gly Gly Gly Ser
                85                  90                  95

Gly Gly Gly Ser Gly Ser Gly Asp Phe Asp Tyr Glu Lys Met Ala Asn
            100                 105                 110

Ala Asn Lys Gly Ala Met Thr Glu Asn Ala Asp Glu Asn Ala Leu Gln
```

```
                115                 120                 125
Ser Asp Ala Lys Gly Lys Leu Asp Ser Val Ala Thr Asp Tyr Gly Ala
        130                 135                 140

Ala Ile Asp Gly Phe Ile Gly Asp Val Ser Gly Leu Ala Asn Gly Asn
145                 150                 155                 160

Gly Ala Thr Gly Asp Phe Ala Gly Ser Asn Ser Gln Met Ala Gln Val
                165                 170                 175

Gly Asp Gly Asp Asn Ser Pro Leu Met Asn Asn Phe Arg Gln Tyr Leu
            180                 185                 190

Pro Ser Leu Pro Gln Ser Val Glu Cys Arg Pro Phe Val Phe Gly Ala
        195                 200                 205

Gly Lys Pro Tyr Glu Phe Ser Ile Asp Cys Asp Lys Ile Asn Leu Phe
    210                 215                 220

Arg Gly Val Phe Ala Phe Leu Leu Tyr Val Ala Thr Phe Met Tyr Val
225                 230                 235                 240

Phe Ser Thr Phe Ala Asn Ile Leu Arg Asn Lys Glu Ser
                245                 250

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 13

Met Lys Lys Thr Ala Ile Ala Ile Ala Val Ala Leu Ala Gly Phe Ala
1               5                   10                  15

Thr Val Ala Gln Ala Arg Ser Gly Gly Gly Thr Val Glu Ser Cys Leu
            20                  25                  30

Ala Lys

<210> SEQ ID NO 14
<211> LENGTH: 272
<212> TYPE: DNA
<213> ORGANISM: Artificial Sequence
<220> FEATURE:
<223> OTHER INFORMATION: Description of Artificial Sequence: Synthetic
      vector sequence
<220> FEATURE:
<221> NAME/KEY: CDS
<222> LOCATION: (60)..(263)

<400> SEQUENCE: 14
aattgtgagc ggataacaat ttaccggttc ttttaacttt agtaaggagg aattaaaaa      59 atg aaa aag tct tta gtc ctc aaa gcc tcc gta gcc gtt gct acc ctc     107
Met Lys Lys Ser Leu Val Leu Lys Ala Ser Val Ala Val Ala Thr Leu
1               5                   10                  15 gtt ccg atg cta agc ttc gct tct aga gcg gcc gct tat cca tac gac     155
Val Pro Met Leu Ser Phe Ala Ser Arg Ala Ala Ala Tyr Pro Tyr Asp
            20                  25                  30 gta cca gac tac gca gga ggt cat cac cat cat cac cat tag aga tct     203
Val Pro Asp Tyr Ala Gly Gly His His His His His His Gln Arg Ser
        35                  40                  45 gga ggc ggt act gtt gaa agt tgt tta gca aaa gct aac ata ctg cgt     251
Gly Gly Gly Thr Val Glu Ser Cys Leu Ala Lys Ala Asn Ile Leu Arg
    50                  55                  60 aat aag gag tct taagtcgac                                           272
Asn Lys Glu Ser
65
```

<210> SEQ ID NO 15
<211> LENGTH: 68
<212> TYPE: PRT
<213> ORGANISM: Artificial Sequence
<220> FEATURE:
<223> OTHER INFORMATION: Description of Artificial Sequence: Synthetic
      vector sequence
<220> FEATURE:
<221> NAME/KEY: MOD_RES
<222> LOCATION: (46)
<223> OTHER INFORMATION: May be Gln or a true stop codon

<400> SEQUENCE: 15

Met Lys Lys Ser Leu Val Leu Lys Ala Ser Val Ala Val Ala Thr Leu
 1               5                  10                  15

Val Pro Met Leu Ser Phe Ala Ser Arg Ala Ala Ala Tyr Pro Tyr Asp
                20                  25                  30

Val Pro Asp Tyr Ala Gly Gly His His His His His His Gln Arg Ser
            35                  40                  45

Gly Gly Gly Thr Val Glu Ser Cys Leu Ala Lys Ala Asn Ile Leu Arg
        50                  55                  60

Asn Lys Glu Ser
 65

<210> SEQ ID NO 16
<211> LENGTH: 281
<212> TYPE: DNA
<213> ORGANISM: Artificial Sequence
<220> FEATURE:
<223> OTHER INFORMATION: Description of Artificial Sequence: Synthetic
      vector sequence
<220> FEATURE:
<221> NAME/KEY: CDS
<222> LOCATION: (60)..(272)

<400> SEQUENCE: 16
aattgtgagc ggataacaat ttaccggttc ttttaacttt agtaaggagg aattaaaaa       59 atg aaa tac cta ttg cct acg gca gcc gct gga ttg tta tta ctc gcg      107
Met Lys Tyr Leu Leu Pro Thr Ala Ala Ala Gly Leu Leu Leu Leu Ala
 1               5                  10                  15 gcc cag ccg gcc atg gcg gcc ctg cag gcc tct aga gcg gcc gct tat      155
Ala Gln Pro Ala Met Ala Ala Leu Gln Ala Ser Arg Ala Ala Ala Tyr
                20                  25                  30 cca tac gac gta cca gac tac gca gga ggt cat cac cat cat cac cat      203
Pro Tyr Asp Val Pro Asp Tyr Ala Gly Gly His His His His His His
            35                  40                  45 tag aga tct gga ggc ggt act gtt gaa agt tgt tta gca aaa gct aac      251
Gln Arg Ser Gly Gly Gly Thr Val Glu Ser Cys Leu Ala Lys Ala Asn
        50                  55                  60 ata ctg cgt aat aag gag tct taagtcgac                                 281
Ile Leu Arg Asn Lys Glu Ser
 65                  70

<210> SEQ ID NO 17
<211> LENGTH: 71
<212> TYPE: PRT
<213> ORGANISM: Artificial Sequence
<220> FEATURE:
<223> OTHER INFORMATION: Description of Artificial Sequence: Synthetic
      vector sequence
<220> FEATURE:
<221> NAME/KEY: MOD_RES
<222> LOCATION: (49)
<223> OTHER INFORMATION: May be Gln or a true stop codon

```
<400> SEQUENCE: 17

Met Lys Tyr Leu Leu Pro Thr Ala Ala Ala Gly Leu Leu Leu Leu Ala
 1               5                  10                  15

Ala Gln Pro Ala Met Ala Ala Leu Gln Ala Ser Arg Ala Ala Ala Tyr
            20                  25                  30

Pro Tyr Asp Val Pro Asp Tyr Ala Gly Gly His His His His His His
        35                  40                  45

Gln Arg Ser Gly Gly Gly Thr Val Glu Ser Cys Leu Ala Lys Ala Asn
    50                  55                  60

Ile Leu Arg Asn Lys Glu Ser
65               70

<210> SEQ ID NO 18
<211> LENGTH: 146
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(132)

<400> SEQUENCE: 18 tct aga ggt gga gga ggt gag gag aag tcc cgg ctg ttg gag aag gag      48
Ser Arg Gly Gly Gly Gly Glu Glu Lys Ser Arg Leu Leu Glu Lys Glu
 1               5                  10                  15 aac cgt gaa ctg gaa aag atc att gct gag aaa gag gag cgt gtc tct      96
Asn Arg Glu Leu Glu Lys Ile Ile Ala Glu Lys Glu Glu Arg Val Ser
            20                  25                  30 gaa ctg cgc cat caa ctc cag tct gta gga ggt tgt taatagggcg cgcc     146
Glu Leu Arg His Gln Leu Gln Ser Val Gly Gly Cys
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 19

Ser Arg Gly Gly Gly Gly Glu Glu Lys Ser Arg Leu Leu Glu Lys Glu
 1               5                  10                  15

Asn Arg Glu Leu Glu Lys Ile Ile Ala Glu Lys Glu Glu Arg Val Ser
            20                  25                  30

Glu Leu Arg His Gln Leu Gln Ser Val Gly Gly Cys
        35                  40

<210> SEQ ID NO 20
<211> LENGTH: 141
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(141)
<220> FEATURE:
<221> NAME/KEY: modified_base
<222> LOCATION: (141)
<223> OTHER INFORMATION: a, c, g, or t

<400> SEQUENCE: 20
```

```
tct cga gga ggt ggt gga aca tcc cgc ctg gag ggc cta cag tca gaa         48
Ser Arg Gly Gly Gly Gly Thr Ser Arg Leu Glu Gly Leu Gln Ser Glu
  1               5                  10                  15 aac cat cgc ctg cga atg aag atc aca gag ctg gat aaa gac ttg gaa         96
Asn His Arg Leu Arg Met Lys Ile Thr Glu Leu Asp Lys Asp Leu Glu
             20                  25                  30 gag gtc acc atg cag ctg cag gac gtc gga ggt tgc gcg gcc gcn           141
Glu Val Thr Met Gln Leu Gln Asp Val Gly Gly Cys Ala Ala Ala
         35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 21

Ser Arg Gly Gly Gly Gly Thr Ser Arg Leu Glu Gly Leu Gln Ser Glu
  1               5                  10                  15

Asn His Arg Leu Arg Met Lys Ile Thr Glu Leu Asp Lys Asp Leu Glu
             20                  25                  30

Glu Val Thr Met Gln Leu Gln Asp Val Gly Gly Cys Ala Ala Ala
         35                  40                  45

<210> SEQ ID NO 22
<211> LENGTH: 3057
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 22
gcgcaacgca attaatgtga gttagctcac tcattaggca ccccaggctt tacactttat     60
gcttccggct cgtatgttgt gtggaattgt gagcggataa caatttaccg gttctttaag    120
gaggaattaa aaaatgaaaa agtctttagt cctcaaagcc tccgtagccg ttgctaccct    180
cgttccgatg ctaagcttcg ctggtgagga aaagtcccgt ctgctggaga agagaaccg    240 tgaactggaa aagatcattg ctgagaaaga ggagcgtgtt tctgaactgc ccatcaact    300 gcagtctgta ggcggttgca cgcgttctag agcggccgct tacccgtacg acgttccgga    360
ctacgcatga taagtcgacc tcgaccaatt cgccctatag tgagtcgtat tacaattcac    420
tggccgtcgt tttacaacgt cgtgactggg aaaaccctgg cgttacccaa cttaatcgcc    480
ttgcagcaca tccccctttc gccagctggc gtaatagcga agaggcccgc accgatcgcc    540
cttcccaaca gttgcgcagc ctgaatggcg aatgggacgc gccctgtagc ggcgcattaa    600
gcgcggcggg tgtggtggtt acgcgcagcg tgaccgctac acttgccagc gccctagcgc    660
ccgctccttt cgctttcttc ccttcctttc tcgccacgtt cgccggcttt ccccgtcaag    720
ctctaaatcg gggctccct  ttaggggtcc gatttagtgc tttacggcac ctcgacccca    780
aaaaacttga ttagggtgat ggttcacgta gtgggccatc gccctgatag acggttttc    840 gccctttgac gttggagtcc acgttcttta atagtggact cttgttccaa actggaacaa    900
cactcaaccc tatctcggtc tattcttttg atttataagg gattttgccg atttcggcct    960
attggttaaa aaatgagctg atttaacaaa aatttaacgc gaattttaac aaaatattaa   1020
cgcttacaat ttaggtggca cttttcgggg aaatgtgcgc ggaaccccta tttgtttatt   1080
```

```
tttctaaata cattcaaata tgtatccgct catgagacaa taaccctgat aaatgcttca    1140
ataatattga aaaggaaga gtatgagtat tcaacatttc cgtgtcgccc ttattccctt     1200
ttttgcggca ttttgccttc ctgttttgc tcacccagaa acgctggtga agtaaaaga     1260 tgctgaagat cagttgggtg cacgagtggg ttacatcgaa ctggatctca acagcggtaa   1320
gatccttgag agttttcgcc ccgaagaacg ttttccaatg atgagcactt ttaaagttct   1380
gctatgtggc gcggtattat cccgtattga cgccgggcaa gagcaactcg gtcgccgcat   1440
acactattct cagaatgact tggttgagta ctcaccagtc acagaaaagc atcttacgga   1500
tggcatgaca gtaagagaat tatgcagtgc tgccataacc atgagtgata acactgcggc   1560
caacttactt ctgacaacga tcggaggacc gaaggagcta accgcttttt tgcacaacat   1620
gggggatcat gtaactcgcc ttgatcgttg ggaaccggag ctgaatgaag ccataccaaa   1680
cgacgagcgt gacaccacga tgcctgtagc aatggcaaca acgttgcgca aactattaac   1740
tggcgaacta cttactctag cttcccggca acaattaata gactggatgg aggcggataa   1800
agttgcagga ccacttctgc gctcggccct tccggctggc tggtttattg ctgataaatc   1860
tggagccggt gagcgtgggt ctcgcggtat cattgcagca ctggggccag atggtaagcc   1920
ctcccgtatc gtagttatct acacgacggg gagtcaggca actatggatg aacgaaatag   1980
acagatcgct gagataggtg cctcactgat taagcattgg taactgtcag accaagttta   2040
ctcatatata ctttagattg atttaaaact tcattttaa tttaaaagga tctaggtgaa    2100
gatccttttt gataatctca tgaccaaaat cccttaacgt gagttttcgt tccactgagc    2160
gtcagacccc gtagaaaaga tcaaaggatc ttcttgagat cctttttttc tgcgcgtaat    2220
ctgctgcttg caaacaaaaa aaccaccgct accagcggtg gtttgtttgc cggatcaaga    2280
gctaccaact ctttttccga aggtaactgg cttcagcaga gcgcagatac caaatactgt    2340
ccttctagtg tagccgtagt taggccacca cttcaagaac tctgtagcac cgcctacata    2400
cctcgctctg ctaatcctgt taccagtggc tgctgccagt ggcgataagt cgtgtcttac    2460
cgggttggac tcaagacgat agttaccgga taaggcgcag cggtcgggct gaacgggggg    2520
ttcgtgcaca cagcccagct tggagcgaac gacctacacc gaactgagat acctacagcg    2580
tgagctatga gaaagcgcca cgcttcccga agggagaaag gcggacaggt atccggtaag    2640
cggcagggtc ggaacaggag agcgcacgag ggagcttcca gggggaaacg cctggtatct    2700
ttatagtcct gtcgggtttc gccacctctg acttgagcgt cgatttttgt gatgctcgtc    2760
agggggggcg gagcctatgg aaaaacgcca gcaacgcggc ctttttacggt tcctggcctt    2820 ttgctggcct tttgctcaca tgttctttcc tgcgttatcc cctgattctg tggataaccg    2880
tattaccgcc tttgagtgag ctgataccgc tcgccgcagc cgaacgaccg agcgcagcga    2940
gtcagtgagc gaggaagcgg aagagcgccc aatacgcaaa ccgcctctcc ccgcgcgttg    3000
gccgattcat taatgcagct ggcacgacag gtttcccgac tggaaagcgg gcagtga     3057
```

<210> SEQ ID NO 23
<211> LENGTH: 3817
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 23

```
gcgcaacgca attaatgtga gttagctcac tcattaggca ccccaggctt tacactttat     60
gcttccggct cgtatgttgt gtggaattgt gagcggataa caatttcaca caggaaacag    120
```

```
ctatgaccat gattacgcca agcgcgttta actttagtaa ggaggaatta aaaaatgaaa      180
tacctgctgc cgaccgcagc cgcgggtttg ctgttactgg cggcccagcc ggctatggcg      240
atgaaagcta ctaaactggt actgggcaac ccgtatgttg ctttgaaat gggttacgac       300 tggttaggtc gtatgccgta caaaggcagc gttgaaaacg gtgcatacaa agctcagggc      360
gttcaactga ccgctaaact gggttaccca atcactgacg acctggacat ctacactcgt      420
ctgggtggca tggtatggcg tgcagacact aaatccaacg tttatggtaa aaaccacgac      480
accggcgttt ctccggtctt cgctggcggt gttgagtacg cgatcactcc tgaaatcgct      540
acccgtctgg aataccagtg gacgaacaac atcggtgacg cacacaccat cggcactcgt      600
ccggacggag gtacatcccg cctggagggc ctacagtcag aaaaccatcg cctgcgaatg      660
aagatcacag agctggataa agacttggaa gaagtcacca tgcagctgca agacgttggc      720
ggttgctaat gagcgcgctc actggccgtc gttttacaac gtcgtgactg ggaaaaccct      780
ggcgttaccc aacttaatcg ccttgcagca catccccctt cgccagctg gcgtaatagc       840 gaagaggccc gcaccgatcg cccttcccaa cagttgcgca gcctgaatgg cgaatgggac      900
gcgccctgta gcggcgcatt aagcgcggcg ggtgtggtgg ttacgcgcag cgtgaccgct      960
acacttgcca gcgccctagc gcccgctcct ttcgctttct tcccttcctt tctcgccacg      1020
ttcgccggct ttccccgtca gctctaaat cggggctcc ctttaggtt ccgatttagt         1080 gctttacggc acctcgaccc caaaaaactt gattagggtg atggttcacg tagtgggcca      1140
tcgccctgat agacggtttt tcgccctttg acgttggagt ccacgttctt taatagtgga     1200
ctcttgttcc aaactggaac aacactcaac cctatctcgg tctattcttt tgatttataa     1260
gggattttgc cgatttcggc ctattggtta aaaaatgagc tgatttaaca aaaatttaac     1320
gcgaatttta acaaaatatt aacgcttaca atttaggtgg cacttttcgg ggaaatgtgc     1380
gcggaacccc tatttgttta ttttttctaaa tacattcaaa tatgtatccg ctcatgagac     1440
aataaccctg ataaatgctt caataatatt gaaaaaggaa gagtatgagt attcaacatt     1500
tccgtgtcgc ccttattccc ttttttgcgg cattttgcct tcctgttttt gctcacccag     1560
aaacgctggt gaaagtaaaa gatgctgaag atcagttggg tgcacgagtg ggttacatcg     1620
aactggatct caacagcggt aagatccttg agagttttcg ccccgaagaa cgttttccaa     1680
tgatgagcac ttttcgaccg aataaatacc tgtgacggaa gatcacttcg cagaataaat     1740
aaatcctggt gtccctgttg ataccgggaa gccctgggcc aacttttggc gaaaatgaga     1800
cgttgatcgg cacgtaagag gttccaactt tcaccataat gaaataagat cactaccggg     1860
cgtatttttt gagttgtcga gattttcagg agctaaggaa gctaaaatgg agaaaaaaat     1920
cactggatat accaccgttg atatatccca atggcatcgt aaagaacatt ttgaggcatt     1980
tcagtcagtt gctcaatgta cctataacca gaccgttcag ctggatatta cggcctttt     2040 aaagaccgta agaaaaata agcacaagtt ttatccggcc tttattcaca ttcttgcccg      2100
cctgatgaat gctcatccgg aattacgtat ggcaatgaaa gacggtgagc tggtgatatg     2160
ggatagtgtt caccttgtt acaccgtttt ccatgagcaa actgaaacgt ttcatcgct       2220 ctggagtgaa taccacgacg atttccggca gtttctacac atatattcgc aagatgtggc     2280
gtgttacggt gaaaacctgg cctatttccc taaagggttt attgagaata tgttttttcgt    2340 ctcagccaat ccctgggtga gtttcaccag ttttgattta aacgtggcca atatggacaa     2400
cttcttcgcc ccgttttcac catgggcaaa tattatacgc aaggcgacaa ggtgctgatg     2460
ccgctggcga ttcaggttca tcatgccgtt tgtgatggct tccatgtcgg cagaatgctt     2520
```

```
aatgaattac aacagtactg cgatgagtgg cagggcgggg cgtaattttt ttaaggcagt    2580
tattggtgcc cttaaacgcc tggttgctac gcctgaataa gtgataataa gcggatgaat    2640
ggcagaaatt cgaaagcaaa ttcgacccgg tcgtcggttc agggcagggt cgttaaatag    2700
ccgcttatgt ctattgctgg tttaccggtt tattgactac cggaagcagt gtgaccgtgt    2760
gcttctcaaa tgcctgaggc cagtttgctc aggctctccc cgtggaggta ataattgacg    2820
atatgatcct ttttttctga tcaaaaagga tctaggtgaa gatccttttt gataatctca    2880
tgaccaaaat cccttaacgt gagttttcgt tccactgagc gtcagacccc gtagaaaaga    2940
tcaaaggatc ttcttgagat cctttttttc tgcgcgtaat ctgctgcttg caaacaaaaa    3000
aaccaccgct accagcggtg gtttgtttgc cggatcaaga gctaccaact cttttccga    3060 aggtaactgg cttcagcaga gcgcagatac caaatactgt ccttctagtg tagccgtagt    3120
taggccacca cttcaagaac tctgtagcac cgcctacata cctcgctctg ctaatcctgt    3180
taccagtggc tgctgccagt ggcgataagt cgtgtcttac cgggttggac tcaagacgat    3240
agttaccgga taaggcgcag cggtcgggct gaacggggggg ttcgtgcaca cagcccagct    3300
tggagcgaac gacctacacc gaactgagat acctacagcg tgagctatga aaagcgcca    3360 cgcttcccga agggagaaag gcggacaggt atccggtaag cggcagggtc ggaacaggag    3420
agcgcacgag ggagcttcca gggggaaacg cctggtatct ttatagtcct gtcgggtttc    3480
gccacctctg acttgagcgt cgatttttgt gatgctcgtc aggggggcgg agcctatgga    3540
aaaacgccag caacgcggcc ttttacggt tcctggcctt ttgctggcct tttgctcaca    3600
tgttctttcc tgcgttatcc cctgattctg tggataaccg tattaccgcc tttgagtgag    3660
ctgataccgc tcgccgcagc cgaacgaccg agcgcagcga gtcagtgagc gaggaagcgg    3720
aagagcgccc aatacgcaaa ccgcctctcc ccgcgcgttg gccgattcat taatgcagct    3780
ggcacgacag gtttcccgac tggaaagcgg gcagtga                           3817

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Cys Gly Gly
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Gly Gly Cys
  1

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
```

-continued

```
                           primer

<400> SEQUENCE: 26
tttagtggta cctttctatt ctcactccgc tg                                      32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tagaaaggta ccactaaagg aattgcgaat aa                                      32

<210> SEQ ID NO 28
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggaattgtga gcggataaca atttaccggt cacacaggaa acagctatga ccatg             55

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
catggtcata gctgtttcct gtgtgaccgg taaattgtta tccgctcaca attcc             55

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
  1               5

<210> SEQ ID NO 31
<211> LENGTH: 70
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(14)
<223> OTHER INFORMATION: Any amino acid
<220> FEATURE:
<221> NAME/KEY: MOD_RES
<222> LOCATION: (16)..(21)
<223> OTHER INFORMATION: Any amino acid
<220> FEATURE:
```

```
<221> NAME/KEY: MOD_RES
<222> LOCATION: (23)..(28)
<223> OTHER INFORMATION: Any amino acid
<220> FEATURE:
<221> NAME/KEY: MOD_RES
<222> LOCATION: (30)..(35)
<223> OTHER INFORMATION: Any amino acid
<220> FEATURE:
<221> NAME/KEY: MOD_RES
<222> LOCATION: (37)..(42)
<223> OTHER INFORMATION: Any amino acid
<220> FEATURE:
<221> NAME/KEY: MOD_RES
<222> LOCATION: (44)..(49)
<223> OTHER INFORMATION: Any amino acid
<220> FEATURE:
<221> NAME/KEY: MOD_RES
<222> LOCATION: (51)..(56)
<223> OTHER INFORMATION: Any amino acid
<220> FEATURE:
<221> NAME/KEY: MOD_RES
<222> LOCATION: (58)..(63)
<223> OTHER INFORMATION: Any amino acid
<220> FEATURE:
<221> NAME/KEY: MOD_RES
<222> LOCATION: (65)..(70)
<223> OTHER INFORMATION: Any amino acid
<220> FEATURE:
<223> OTHER INFORMATION: This sequence may encompass 2 to 10 repeating
      units of LXXXXXX

<400> SEQUENCE: 31

Leu Xaa Xaa Xaa Xaa Xaa Xaa Leu Xaa Xaa Xaa Xaa Xaa Xaa Leu Xaa
 1               5                  10                  15

Xaa Xaa Xaa Xaa Xaa Leu Xaa Xaa Xaa Xaa Xaa Xaa Leu Xaa Xaa Xaa
                20                  25                  30

Xaa Xaa Xaa Leu Xaa Xaa Xaa Xaa Xaa Xaa Leu Xaa Xaa Xaa Xaa Xaa
            35                  40                  45

Xaa Leu Xaa Xaa Xaa Xaa Xaa Xaa Leu Xaa Xaa Xaa Xaa Xaa Xaa Leu
    50                  55                  60

Xaa Xaa Xaa Xaa Xaa Xaa
65                  70
```

ADAPTOR-DIRECTED HELPER SYSTEMS

CROSS-REFERENCE

This application is a continuation application of Ser. No. 10/033,399, filed Nov. 2, 2001 now U.S. Pat. No. 7,175,983. This priority application is incorporated herein by reference in its entirety.

TECHNICAL FIELD

This invention is in the field of display technology. Specifically, the invention relates to the generation of adapter-directed display systems for exogenous display of polypeptides on genetic packages. The compositions and methods embodied in the present invention are particularly useful for identifying from a vast repertoire of polypeptides those individual members exhibiting desired properties.

BACKGROUND OF THE INVENTION

The display of polypeptides on the surface of genetic packages represents a powerful methodology for carrying out molecule evolution in the laboratory. The ability to construct libraries of enormous molecular diversity and to select for molecules with desired properties has made this technology applicable to a wide range of problems. The origins of phage display date to the mid-1980s when George Smith first expressed an exogenous segment of a protein on the surface of bacteriophage M13 virus particles by fusing the exogenous sequence to a phage coat protein (*Science* (1985) 228: 1315-1317). Two groundbreaking concepts emerged from Smith's initial experiment. First, the experiment suggested that a vast diverse repertoire of polypeptides could be constructed in which individual phage particles display unique polypeptides. Second, the experiment confirmed a direct physical link between phenotype and genotype. That is, the phage displaying the desired polypeptide also harbors the DNA encoding the polypeptide, which can be readily isolated for subsequent analyses. McCafferty and Ladner extended these concepts to screen repertoire of polypeptides such as single-chain antibodies displayed on the surface of phage particles (U.S. Pat. Nos. 5,969,108 and 5,837,500). Since then, phage display has become a popular technique for protein engineering.

A range of display systems have been developed based on George Smith's findings. These systems can be broadly classified into two categories. The first generation system is a one-vector system. The vector in this system contains the entire phage genome, insert therein an exogenous sequence in-frame with a coat protein gene. Because the resulting phage particles carry the entire phage genomes, they are relatively unstable and less infectious. The second generation system, commonly referred to as the phagemid system, has two components: (1) a phagemid vector carrying the exogenous sequence fused to phage coat protein, and a phage-derived origin of replication to allow packaging the phagemid into a phage particle; and (2) a helper phage vector carrying all other sequences required for phage packaging. The helper vector is typically replication-defective such as M13KO7 helper vector manufactured by Amersham Pharmacia Biotech and its derivative VCSM13 that is produced by Stratagen. Upon superinfection of a bacterial cell with the helper phages, newly packaged phages carrying the phagemid vector and displaying the exogenous sequence are produced.

As such, the prior phagemid system requires fusion of the exogenous sequence to at least part of a phage outer-surface sequence (i.e. the coat sequence). The fusion or display sites most commonly used are within genes III and VIII of M13 bacteriophage, although genes VI, VII and IX fusions have been reported. However, these fusion systems bear a number of pronounced limitations. First and foremost, the expression of coat proteins is toxic to the host cells, thus tight regulation of the coat-fusion must be monitored. Even so, the unavoidable promoter leakage can cause loss of members of a diverse library. Maintaining the stability of a library is especially critical for generating a vast diverse repertoire of molecules (such as antigen-binding units) with a complexity of at least $10^9$. Second, expression of certain coat proteins such as the gene III product (pIII) can render host cells resistant to infection with helper phage-required for the production of progeny phage particles. Third, the fusion format including the gene III and gene VIII phage display systems restrict the point of insertion to the 5' end of the outer-surface sequence. The exogenous polypeptide thus must be linked to the N-terminus of the outer-surface proteins. Consequently, cDNA libraries containing fragments of coding sequences of all reading frames cannot be fully displayed by these fusion systems due to frequent disruption of reading frames by internal stop codons. Furthermore, the fusion system is unstable due to recombination between the fusion and the wildtype outer-surface protein that is typically provided by a helper vector. Finally, since the phagemid vector contains at least a portion of the outer-surface sequences, large exogenous sequence may not be efficiently expressed because of low transformation efficiency of a large vector. Transformation efficiency, however, is a critical factor for the production of libraries of high complexity.

Various modifications to the fusion phagemid system have been described. WO 91/17271 proposes construction of a phage display system in which the exogenous sequence is displayed via interaction of a "tag" and a "tag ligand." The system contains a phage genomic vector that carries the exogenous sequence joined to a tag sequence. The same vector carries a tag ligand sequence fused in-frame with a coat protein gene. Upon infection of a host cell with the vector, it is speculated that phage particles expressing the exogenous sequences would be produced. However, the disclosure of WO 91/17271 does not provide a teaching which enables the general idea to be carried out. For example, WO 91/17271 does not demonstrate that any sequence has been displayed on the surface of phage particle via the interaction between a "tag" and a "ligand;" nor has it demonstrated that the protein, if expressed, retains biological activity. Furthermore, because the proposed system employs a phage genomic vector carrying all phage coat protein genes in the same vector, the system inevitably inherits all limitations and drawbacks as described above.

Crameri et al. devised a system to display cDNA products, in which Fos oncogene was inserted adjacent to the exogenous sequence to be displayed on a phagemid vector, and Jun oncogene was inserted adjacent to gene III on the same vector (see Crameri et al. (1993) *Gene* 137:69-75). These two fusion sequences were placed under the control of two separate promoters. The Crameri approach exploits the preferential interaction between fos and jun proteins: as the Fos-exogenous polypeptide is expressed and secreted into the periplasmic space, it forms a complex with pIII-Jun which is then packaged into the phage particles upon superinfection with M13KO7 helper phage. Although the exogenous sequence in this system is not directly linked to an outer-surface sequence, the constitutive expression of phage coat protein pIII under a separate promoter of the same vector still causes substantial toxicity to the host cells.

Another variant similar to the Crameri system is the "cysteine-coupled" display system described in WO 01/05950. The attachment and display of the exogenous polypeptide are mediated by the formation of disulfide bond between two cysteine residues, one of which is contained in the exogenous sequence, and the other is inserted in the outer-surface sequence. The one vector system described in WO 01/05950 is a phagemid vector carrying two separate promoter-controlled expression cassettes: one expresses the exogenous sequence, and the another expresses the coat protein pIII. The two-vector system described in WO 01/05950 contains a phagemid vector carrying an exogenous sequence, and a plasmid expressing the coat protein pIII. The two vectors are used to co-transfect E. Coli cells. Upon superinfection with the helper phages, M13KO7, the phagemid and/or the plasmid are packaged into the resulting phage particles. Although this system avoids the expression of a fusion comprising the exogenous protein linked to an outer-surface protein, the system again fails to minimize the toxicity of coat proteins to the host cells because of the constitutive expression of the coat protein pIII in either the one-vector or the two-vector system. Furthermore, the two-vector system described in WO 01/05950 inevitably produces phage particles with mispackaged vectors carrying the outer-surface sequences and not the exogenous gene upon infection of the helper phages. Mispackaging is a well-known problem associated with two-vector system. It has been shown that the pIII-supplementing plasmid vectors were mispackaged into helper phage particles (Rondot et al. (2000) *Nature* 19: 75-78).

Finally, the aforementioned prior phage display systems are not compatible with other display systems, such as a bacterial display system. To present the same phage-displayed exogenous sequence directly onto a bacterial cell, the exogenous sequence must first be subcloned into a bacterial display vector.

Thus, there remains a considerable need for improved compositions and methods for exogenous display on genetic packages. An ideal system would avoid the drawbacks of the previously reported systems. The present invention satisfies these needs and provides related advantages as well.

SUMMARY OF THE INVENTION

A principal aspect of the present invention is the design of systems that enable display of polypeptides not linked to any outer-surface sequences of a genetic package via peptide bonds. The experimental design provides an unprecedented flexibility for the presentation and/or selection of proteins with desired properties on a genetic package such as a phage particle. The technical advantages of the subject phage-display system are manifold. First, the system avoids all drawbacks associated with expression of the outer-surface proteins by the expression vectors. As mentioned above, the drawbacks include (1) high toxicity to the host cell as a result of constitutive expression of the outer-surface sequences; (2) resistance of host cells to the infection of helper phages that is required for the production of progeny phage particles; (3) limitation on the orientation of the proteins to be displayed because of the unidirectional display of N-terminal fusion product; and (4) instability of the fusion product due to recombination between the fusion outer-surface sequence and the wildtype outer-surface sequence which is typically provided by the helper vector. Second, the system eliminates the possibility of mispackaging plasmids carrying the outer-surface sequences and not the gene of interest; such plasmids are used in the two-vector system described in WO 01/0595. While avoiding these and other intrinsic shortcomings of the prior display systems, the subject system further provides the flexibility of presenting one copy (monovalent display) or multiple copies (multivalent display) of a polypeptide per genetic package. The subject systems are particularly useful for expressing and screening a vast diverse repertoire of polypeptides (i.e. antigen-binding units) based on their ability to bind molecules of particular interest. The polypeptides displayed by the subject systems are functional.

Accordingly, the present invention provides an adapter-directed display system for displaying an exogenous polypeptide on the outer surface of a genetic package. The system comprises: (a) an expression vector comprising a coding sequence that encodes the exogenous polypeptide fused in-frame to a first adapter sequence, wherein the vector is devoid of outer-surface sequences encoding any functional outer-surface proteins of the genetic package; (b) a helper vector comprising outer-surface sequences encoding outer-surface proteins necessary for packaging the genetic package, wherein at least one of the outer-surface protein is fused in-frame to a second adapter, said first and second adapter acting, when the polypeptide is produced in a suitable host cell, to cause the display of the polypeptide via pairwise interaction between the first and second adapters.

The employed genetic package can be viruses, cells, and spores. In one embodiment, the subject system is a phage display system. The outer-surface sequences encode functional coat proteins of a phage. The preferred outer-surface sequences encode functional coat proteins of a phage such as a filamentous phage. Preferred outer-surface sequences are selected from the group consisting of gene III, gene VI, gene VII, gene VIII, and gene IX of a filamentous phage.

In another embodiment the subject system is a bacterial display system. The outer-surface sequences excluded in the expression vector but included in the bacterial helper vector encode bacterial outer-surface proteins. Preferred outer-surface proteins are selected from the group consisting of Lpp-OmpA, TraT, Pal, Oprl, Inp and AIDA-I.

For constructing the subject display systems, the first and second adapters can be homodimerization sequences or heterodimerization sequences. Preferred homodimerization sequences are two pairing cysteine residues capable of forming disulfide bond. Preferred heterodimerization sequences include those that are essentially incapable of forming homodimers under physiological buffer conditions and/or physiological body temperatures, such as those that are derived from heterodimeric receptors GABA$_B$ receptors 1 and 2. Other preferred adapters may adopt a coiled-coil secondary structure.

The present invention also provides a helper vector for displaying a polypeptide on the outer surface of a genetic package. The vector comprises: outer-surface sequences necessary for packaging the genetic package, wherein at least one of the surface presenting sequences is fused in-frame to an adapter, said adapter acting, when the polypeptide is produced in a suitable host cell, to cause the display of the polypeptide. In one aspect, the subject helper vector is a bacterial helper vector (see, e.g. FIG. 26). In another aspect, the helper vector is a phage helper vector (also referred to herein as "UltraHelper phage vector"). Preferred phage helper vectors include but are not limited to GM-UltraHelper phage vector shown in FIG. 5A, CM-UltraHelper phage vector shown in FIG. 13A, and GMCT-UltraHelper phage vector shown in FIG. 19A.

The present invention further provides an expression vector for producing a polypeptide within or on the outer surface of a genetic package. The subject expression vector comprises: a coding sequence encoding the polypeptide fused in-frame to a first adapter, wherein the vector is devoid of outer-surface sequences encoding any functional outer-surface proteins of the genetic package, and display of the polypeptide on the outer surface of the genetic package is mediated via non-covalent pairwise interaction between the first adapter and a second adapter, wherein the second adapter is fused to an outer-surface sequence. In one aspect the expression vector is a phagemid. Illustrative phagemid of the subject phage display systems are pABMX14 shown in FIG. 9A, pABMX15 shown in FIG. 15A, and pAMBX22 shown in FIG. 25A.

Also included in the present invention are kits comprising the adapter-directed display systems, and individual components of the systems including expression and helper vectors. Further provided in the invention are host cells comprising the subject vectors.

In a separate embodiment, the present invention provides a genetic package displaying on its external surface a fusion polypeptide. The fusion polypeptide comprises a polypeptide sequence to be displayed, fused in-frame with a first adapter, said first adapter acting, when the fusion polypeptide is produced in a suitable host cell, to cause the display of the fusion polypeptide via non-covalent pairwise interaction between the first adapter and a second adapter that is linked to an outer-surface protein. The genetic package can be viruses, cells, and spores.

In yet another embodiment, the present invention provides a selectable library comprising a plurality of genetic packages at least one being the genetic package as described above.

In still another embodiment, the present invention provides a method of displaying a polypeptide on the outer surface of a genetic package by causing the subject adapter-directed display system to be transcribed and translated in a suitable host cell. Selectable libraries produced by this method are also encompassed by the present invention.

The present invention further provides a method of detecting the presence of a specific interaction between a test agent and an exogenous polypeptide that is displayed on a genetic package. The method comprises the steps of (a) providing a genetic package displaying the exogenous polypeptide that is prepared according to the above-mentioned method; (b) contacting the genetic package with the test agent under conditions suitable to produce a stable polypeptide-agent complex; and (c) detecting the formation of the stable polypeptide-agent complex on the genetic package, thereby detecting the presence of a specific interaction. In one aspect, the exogenous polypeptide is selected from the group consisting of antigen-binding unit, cell surface receptor, receptor ligand, cytosolic protein, secreted protein, and nuclear protein. In a preferred aspect, the exogenous polypeptide is an antigen-binding unit. The test agent can be composed of protein, carbohydrate, lipid, and combinations thereof. Preferred test agent is an antigen or a ligand.

Finally, the present invention provides a method of obtaining a polypeptide with desired property. The method comprises: (a) providing a selectable library made by the invention method; and (b) screening the selectable library to obtain at least one genetic package displaying a polypeptide with the desired property. In one aspect, the desired property is binding specificity to an agent of interest. In another aspect, the step if screening the selectable library further comprises isolating the genetic package that displays a polypeptide having the desired property. Such step may further involve obtaining a nucleotide sequence from the genetic package that encodes the polypeptide with the desired property. The polypeptide with the desired property may be one of the following types of proteins: antigen-binding unit, cell surface receptor, receptor ligand, cytosolic protein, secreted protein, and nuclear protein.

EXPLAINATION OF ABBREVIATIONS USED HEREIN

1. Nsc: Non-single chain
2. Sc: Sing-chain
3. Abu: Antigen-binding unit
4. Abus: Antigen-binding units
4. L chain: Light chain
5. H chain: Heavy chain
6. VL: Light chain variable region
7. VH: Heavy chain variable region

BRIEF DESCRIPTION OF THE DRAWINGS

FIG. 3B depicts the nucleotide and amino acid (top: SEQ ID NO: 1 encodes SEQ ID NO: 2) sequence of the gene III leader sequence contained in the helper phage vector. A KpnI restriction site is introduced downstream of the leader sequence without altering coding region of gene III (bottom: SEQ ID NO: 3 encodes SEQ ID NO: 2).

FIG. 5B depicts the nucleotide (SEQ ID NO: 4) and amino acid (SEQ ID NO: 5) sequences of the segment spanning the KpnI and BgIII sites. FIG. 5C depicts the trypsin cleavage sites (Tryp) in the GR2-Myc domain (SEQ ID NO: 6).

FIG. 9B shows the complete nucleotide sequence of pABMX14 (SEQ ID NO: 7). The vector contains an ampicillin-resistance gene for antibiotic selection (AMP), a plasmid replication origin (ColE1ori), the fl phage replication origin (fl ori), and the lac promoter/lac O1 driving the expression of downstream sequence plac-RBS-pelB-GR1-DH (HA and 6xHis tag (SEQ ID NO: 30)). The NcoI/XbaI or NcoI/NotI or XbaI/NotI restriction sites can be used to insert exogenous sequence for display or production of soluble protein in a bacterial cell.

When the same blot was reprobed with the anti-HA antibodies (see right panel of FIG. 11), a band corresponding to the scFv-GR1-DH/GR2-Myc-pIII complex was detected by the anti-HA antibodies in lane 2. This confirms the display of scFv-GR1-DH fusion upon the superinfection of GM-Ultra-Helper phages.

Figure 12:
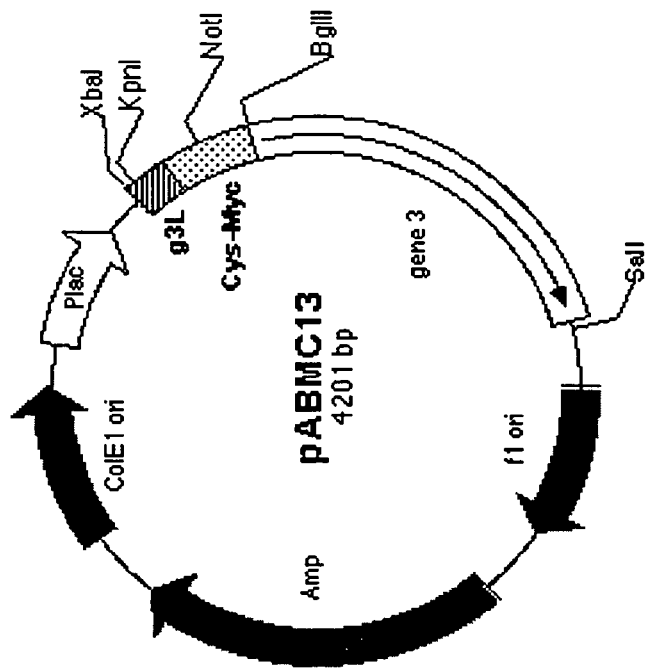

FIG. 12 is a schematic representation of vector pABMC13. The vector contains a DNA fragment including a partial gIII leader sequence with KpnI site, Ala-Cys-Gly-Gly (SEQ ID NO: 24) coding sequence and a Myc-tag placed to 5' of gene III.

Figure 13A:
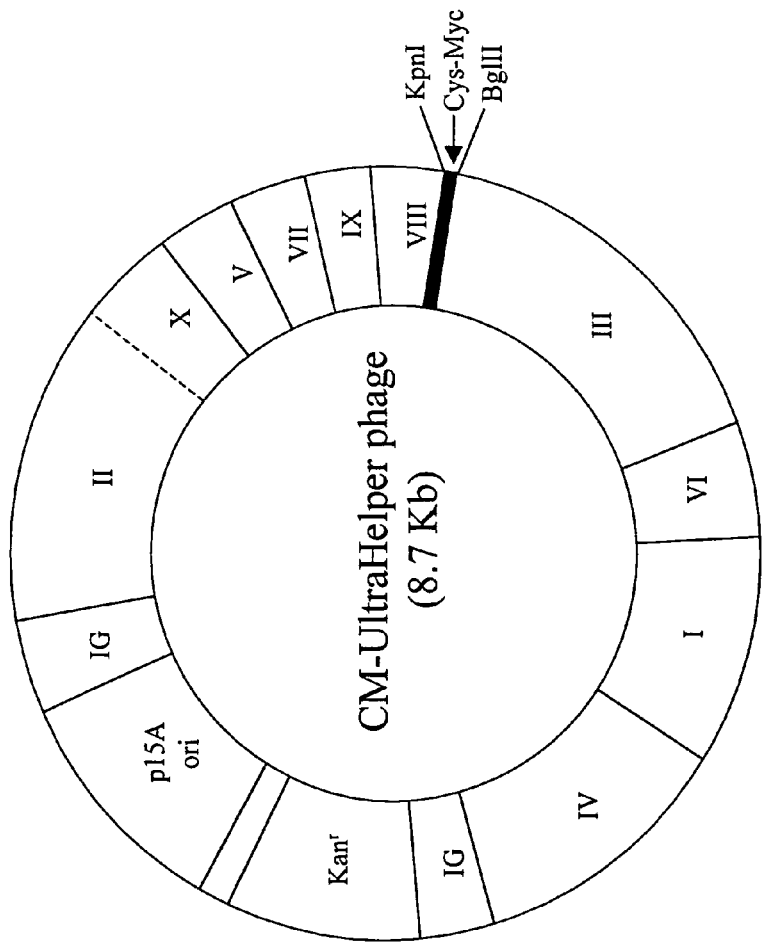

FIG. 13A is a schematic representation of the CM-UltraHelper phage vector. FIG. 13B depicts the nucleotides (SEQ ID NO: 8) and amino acids (SEQ ID NO: 9) of the segment spanning the Kpni and BglII sites. The vector contains a nucleotide sequence encoding Ala-Cys-Gly-Gly (SEQ ID NO: 24) fused with a Myc-tag, which is placed to the 5' of gene III sequence. In addition, the vector comprises an amber stop codon flanked by the gene III leader sequence and the Cys-Myc coding region. The introduction of an amber codon permits phage production only in suppressor bacterial strains.

Figure 14:
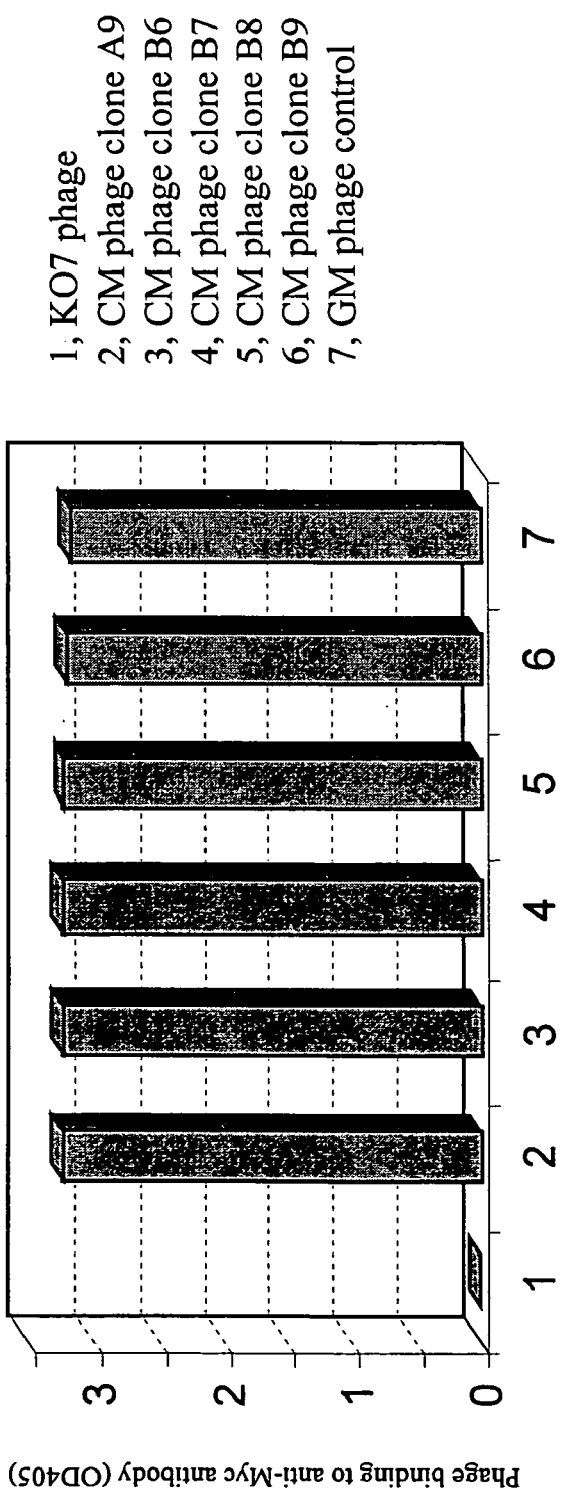

FIG. 14 depicts the results of an ELISA assay using anti-Myc antibody to detect Cys-Myc-pIII fusions that are assembled into the CM-UltraHelper phage particles. Line 1 represents the negative control, M13KO7 helper phage. Lanes 2-6 represents five clones of CM-UltraHelper phages. Line 7 represents the positive control, GM-UltraHelper phage.

Figure 15A:
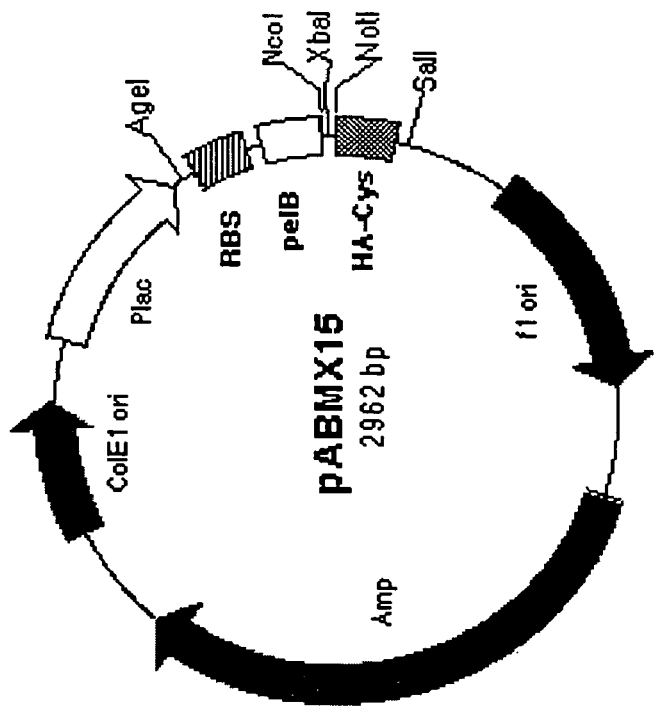

FIG. 15A is a schematic representation of vector pABMX15. FIG. 15B shows the complete nucleotide sequence of pAMBX15 (SEQ ID NO: 10). The vector contains an ampicillin-resistance gene for antibiotic selection (AMP), a plasmid replication origin (ColE1 ori), the fl phage replication origin (fl ori), and the lac promoter/lac O1 driving the expression of the downstream sequence plac-RBS-pelB-HA-Cys. The NcoI/XbaI or NcoI/NotI or XbaI/NotI restriction sites can be used to insert exogenous sequence for display or production of soluble protein in a bacterial cell.

Figure 16:
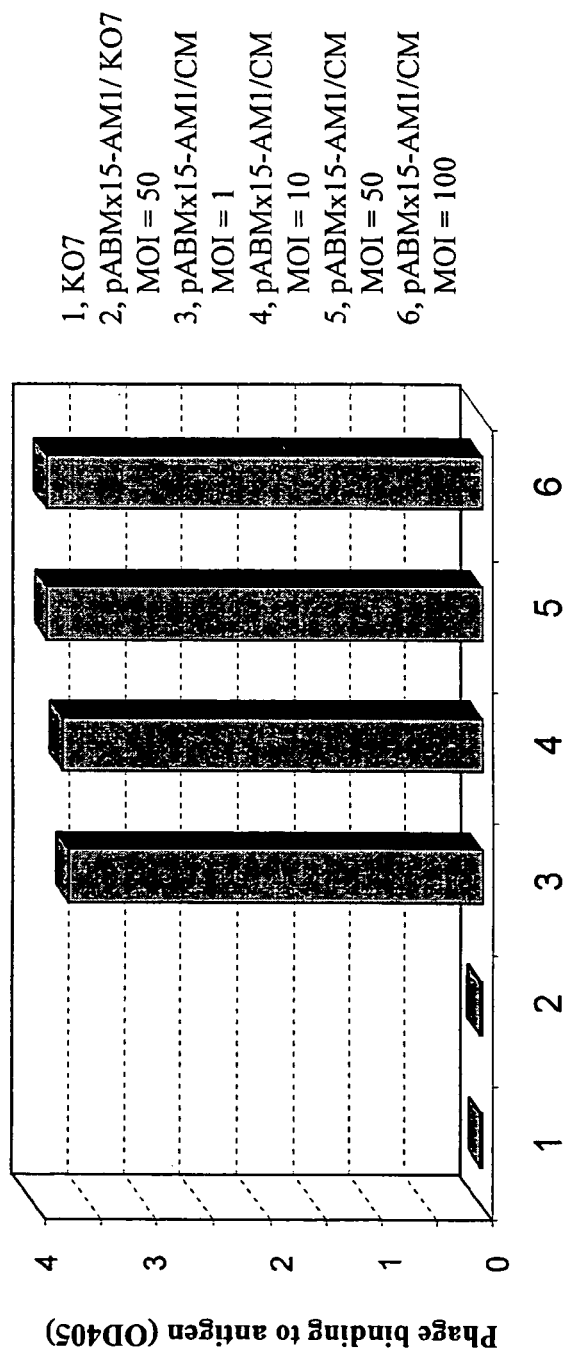

FIG. 16 depicts the results of a phage binding assay, in which the phage particles were generated upon superinfection of bacterial TG1 cells with either CM-UltraHelper phage or M13KO7 (also denoted "KO7") helper phage. The bacterial TG1 cells harbors the pABMX15-AM1 phagemid vector for expression of scFv-HA-Cys fusion. The results demonstrate the display of functional scFv on phage particles using pABMX15 phagemid and the CM-UltraHelper phage vector. There is no significant change in the level of scFv display in the range of 1 to 100 of multiplicity of infection (MIO) shown in line 3-6. Lines 1 and 2 represent two negative control of KO7 helper phages. As indicated by lane 2, no scFv-HA-Cys was detected when negative control M13KO7 helper phages were employed.

Figure 17:
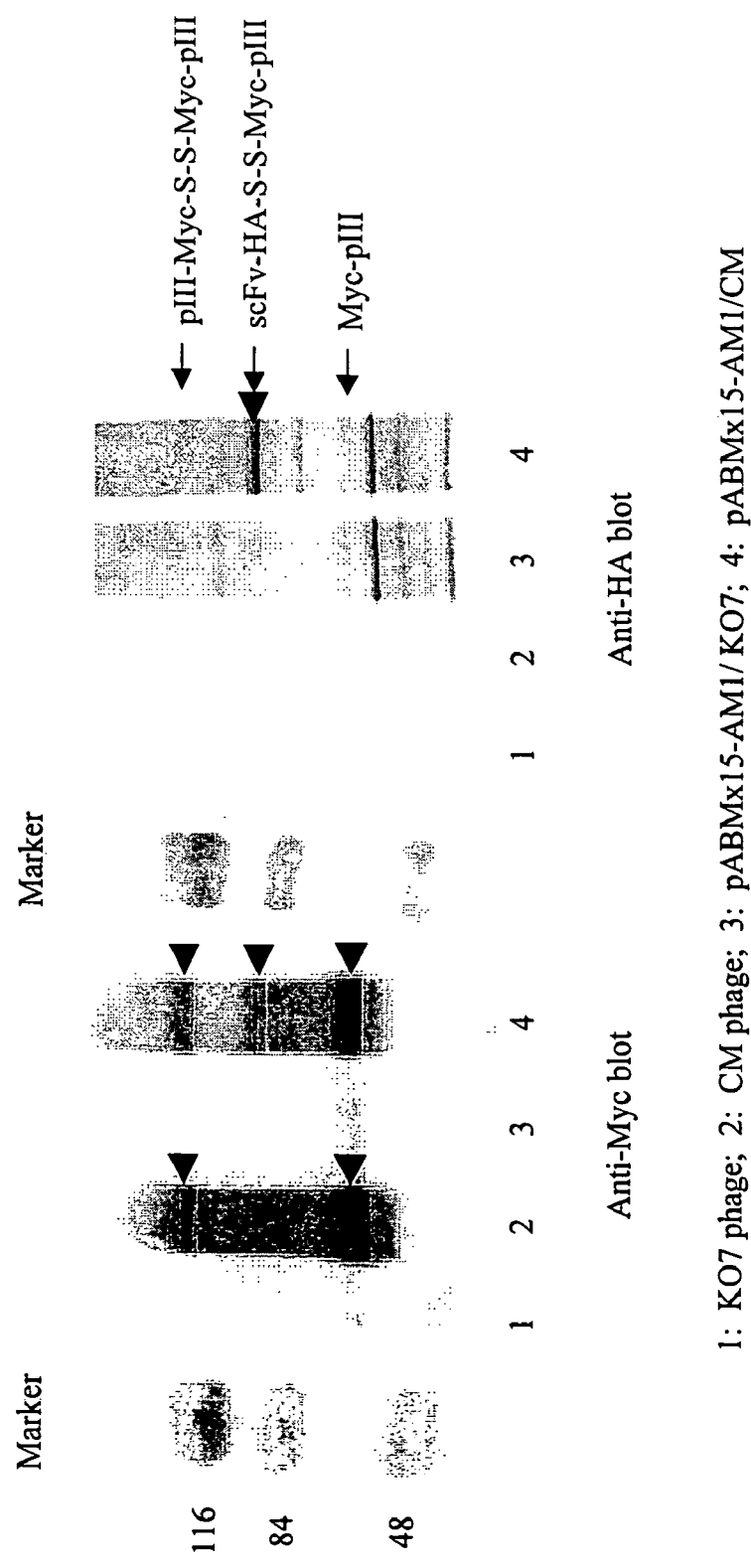

FIG. 17, left panel, is a reproduction of an anti-Myc immunoblot of phage coat proteins. Lane 1 represents a negative control in which KO7 phage alone was employed. Lane 2 represents a negative control in which CM-UltraHelper phage vector alone was used. Lane 3 represents a negative control in which the scFv-HA-Cys fusion expressed by phagemid pABMX15 was not detected upon superinfection with KO7 phage. Lane 4 represents a phage clone in which the scFv-HA-Cys fusion expressed by phagemid pABMX15 was displayed successfully upon superinfection with CM-Ultra-Helper phage vector. Anti-Myc antibody detects, only in lane 4, a band corresponding to the scFv-HA-S-S-Myc-pIII complex formed via the pairwise interaction of the paring cysteines. This result indicates that display of scFv-HA-Cys occurs only when the phagemid is rescued by CM-Ultra- Helper phage and not by M13KO7 helper phage. pIII-Myc dimer was detected in line 2 and line 4 due to the disulfide bond established between two cysteine residues introduced at the 5' end of pIII sequence.

When the same blot was reprobed with the anti-HA antibodies (see right panel of FIG. 17), a band corresponding to the scFv-HA-S-S-Myc-pIII complex was detected by the anti-HA antibodies in lane 4 and not in control lanes 1-3. This confirms the display of scFv-HA-S fusion upon the rescue of GM-UltraHelper phages.

Figure 18:
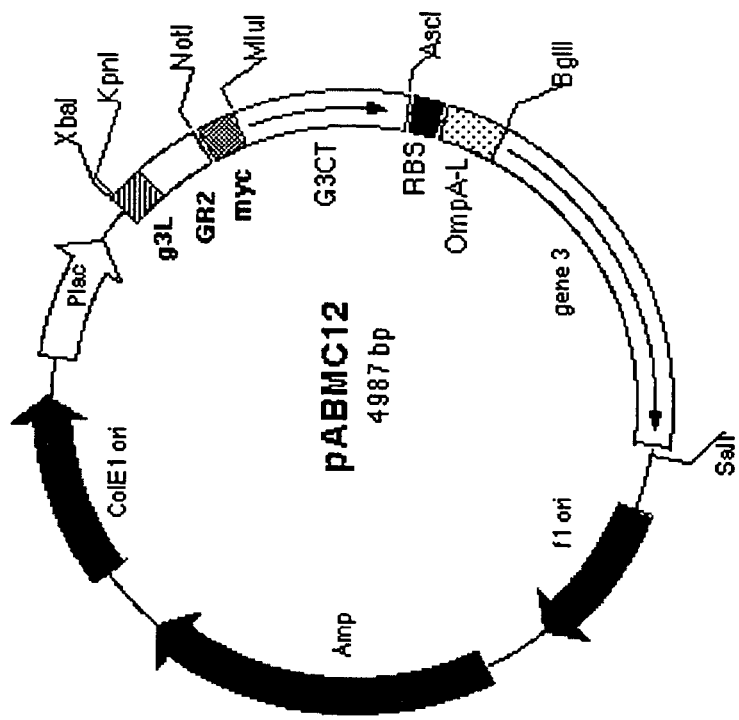

FIG. 18 is a schematic representation of vector pABMC12. In addition to the nucleotide sequence of vector pABMC6, vector pABMC12 contains a DNA fragment including coding sequence for the C-terminal portion of gene III fused to GR2-Myc coding sequence, and a ribosome binding sequence (RBS)-OmpA leader sequence fused to a gene III sequence.

Figure 19A:
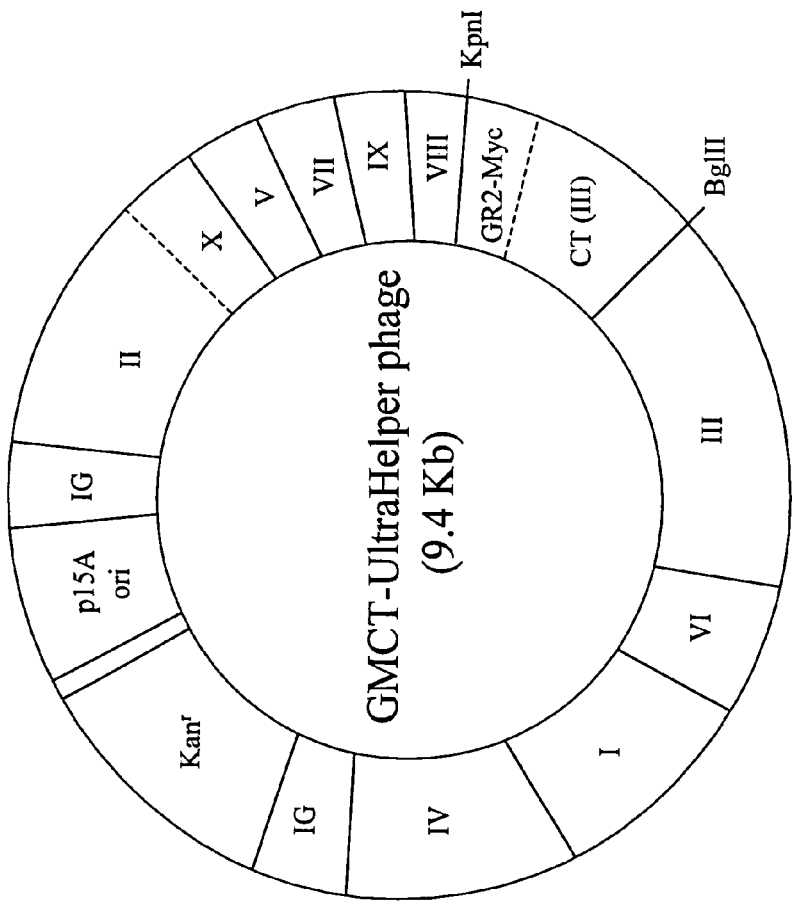

FIG. 19A is a schematic representation of the GMCT-UltraHelper phage vector. FIG. 19B depicts the nucleotides (SEQ ID NO: 11) and amino acids (SEQ ID NOS: 12 and 13, respectively) of the segment spanning the KpnI and BglII sites. The vector contains nucleotide sequence encoding the additional copy of engineered gene III fused to adapter GR2 and Myc-tag in K07/kpn phage vector, and ribosome binding sequence-OmpA leader sequence adjacent to the K07 gene III sequence.

Figure 20:
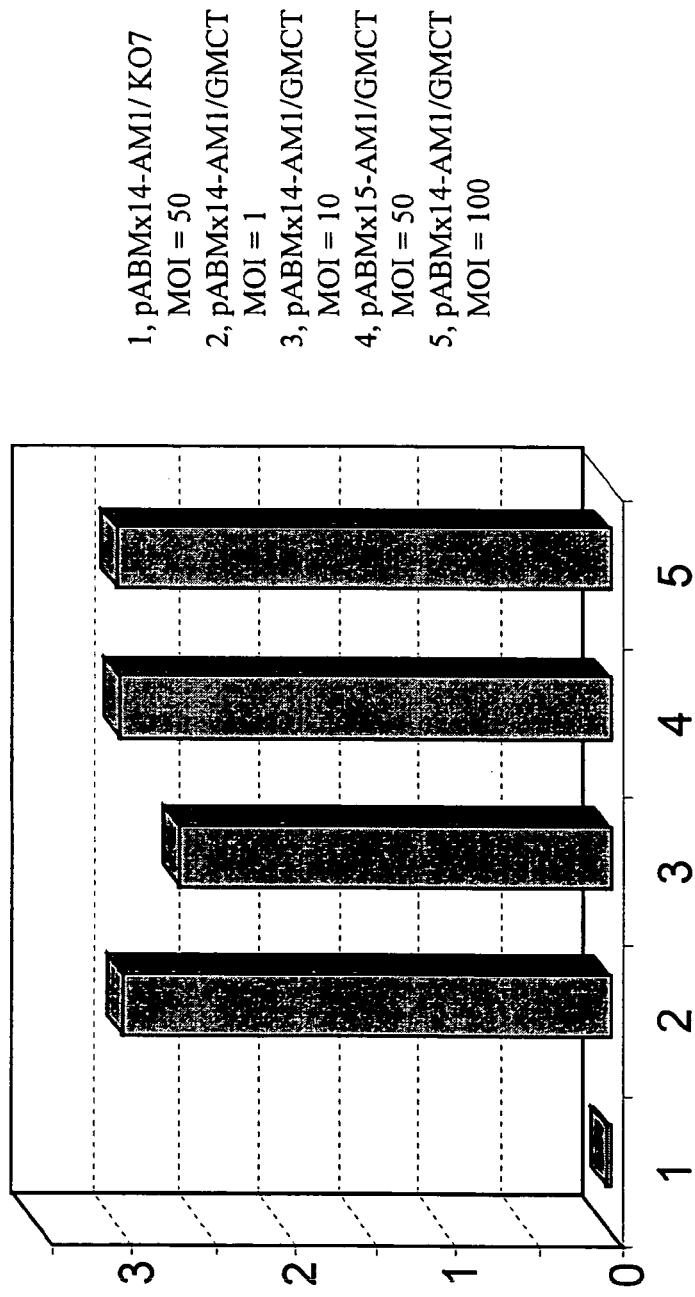

FIG. 20 depicts the results of a phage binding assay, in which the phage particles were generated upon superinfection bacterial TG1 cells with either GMCT-UltraHelper phage or the control M13KO7 helper phage. The TG1 cells harbor the pABMX14-AM1 phagemid vector for expression of the scFv-GR1-DH fusion. The results demonstrate the display of functional scFv on phage particles using pABMX14 phagemid and the GMCT-UltraHelper phage vector (lanes 2-5). There is no significant change in the level of scFv display in the range of 1 to 100 of multiplicity of infection (MIO). Line 1 represents a negative control in which scFv was not displayed upon superinfection of KO7 helper phages.

Figure 21:
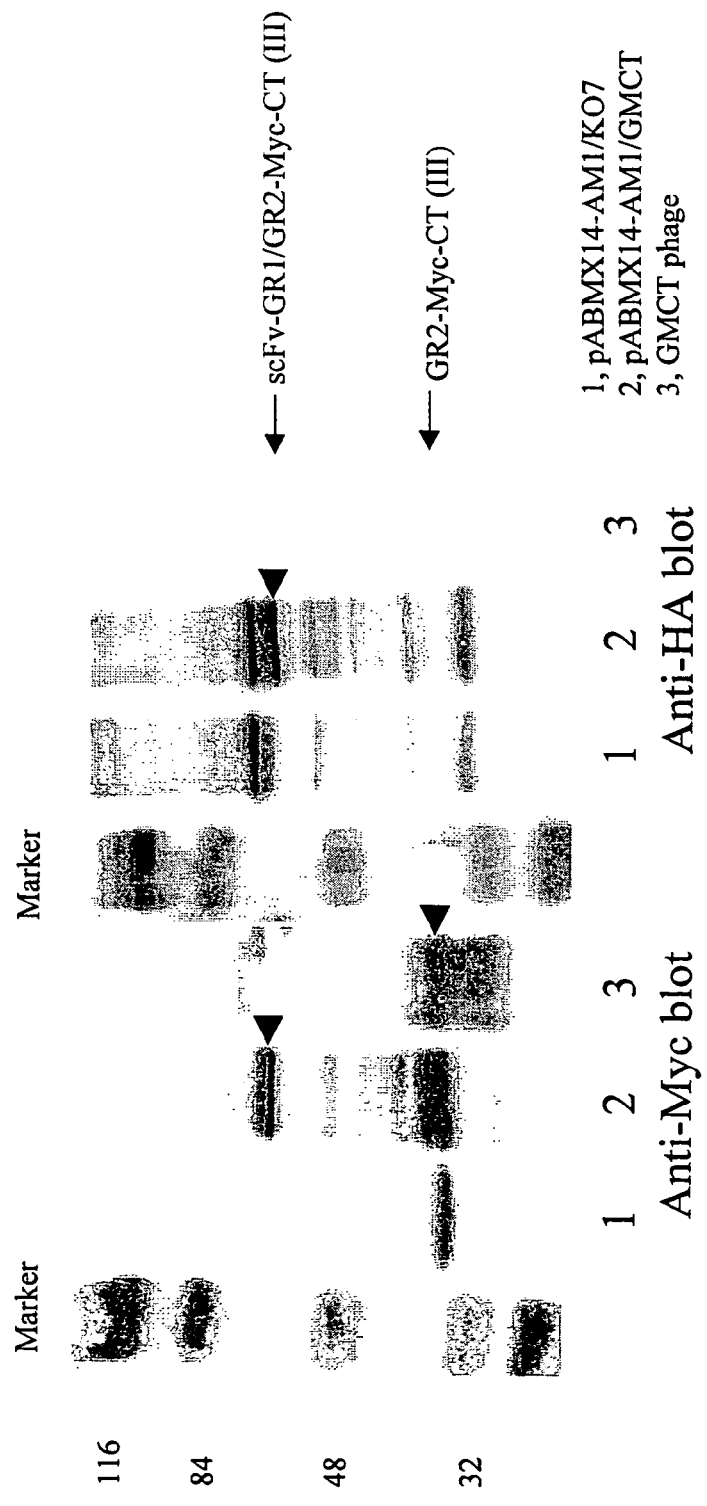

FIG. 21, left panel, is a reproduction of an anti-Myc immunoblot of phage coat proteins. Lane 1 represents a negative control in which KO7 phage was employed to rescue pABMX14 phagemid. Lane 2 represents a phage clone in which the scFv antibody expressed by phagemid pABMX14 was displayed successfully upon superinfection with GMCT-UltraHelper phages. Lane 3 represents another negative control in which GMCT-UltraHelper phage alone was used. Anti-Myc antibody detects, only in lane 2, a band corresponding to the scFv-GR1/GR2-Myc-CT (III) complex formed via the pairwise interaction of GR1 and GR2. This result indicates that display of scFv-GR1 occurs only when the phagemid is rescued by GMCT-UltraHelper phage and not by KO7 helper phage.

When the same blot was reprobed with the anti-HA antibodies (see right panel of FIG. 21), a band corresponding to the scFv-GR1/GR2-Myc-CT (III) complex was detected by the anti-HA antibodies in lane 2 and not in control lane 1 or 3. This confirms the display of scFv-HA-S fusion upon the rescue of GMCT-UltraHelper phages.

FIG. 22A depicts a schematic representation of vector pABMD1 and pABMD2. FIG. 22B depicts the nucleotide (SEQ ID NOS: 14 and 16, respectively) and amino acid sequences (SEQ ID NOS: 15 and 17, respectively) spanning the lac promoter/lac O1 and the SalI site.

FIG. 23 depicts the C-terminal sequences of GABA$_B$ receptors 1 (SEQ ID NO: 18 encodes SEQ ID NO: 19) and 2 (SEQ ID NO: 20 encodes SEQ ID NO: 21). An exogenous cysteine residue is introduced by adding "ValGlyGlyCys" spacer (SEQ ID NO: 25) at the C-termini of the sequence.

Figure 24:
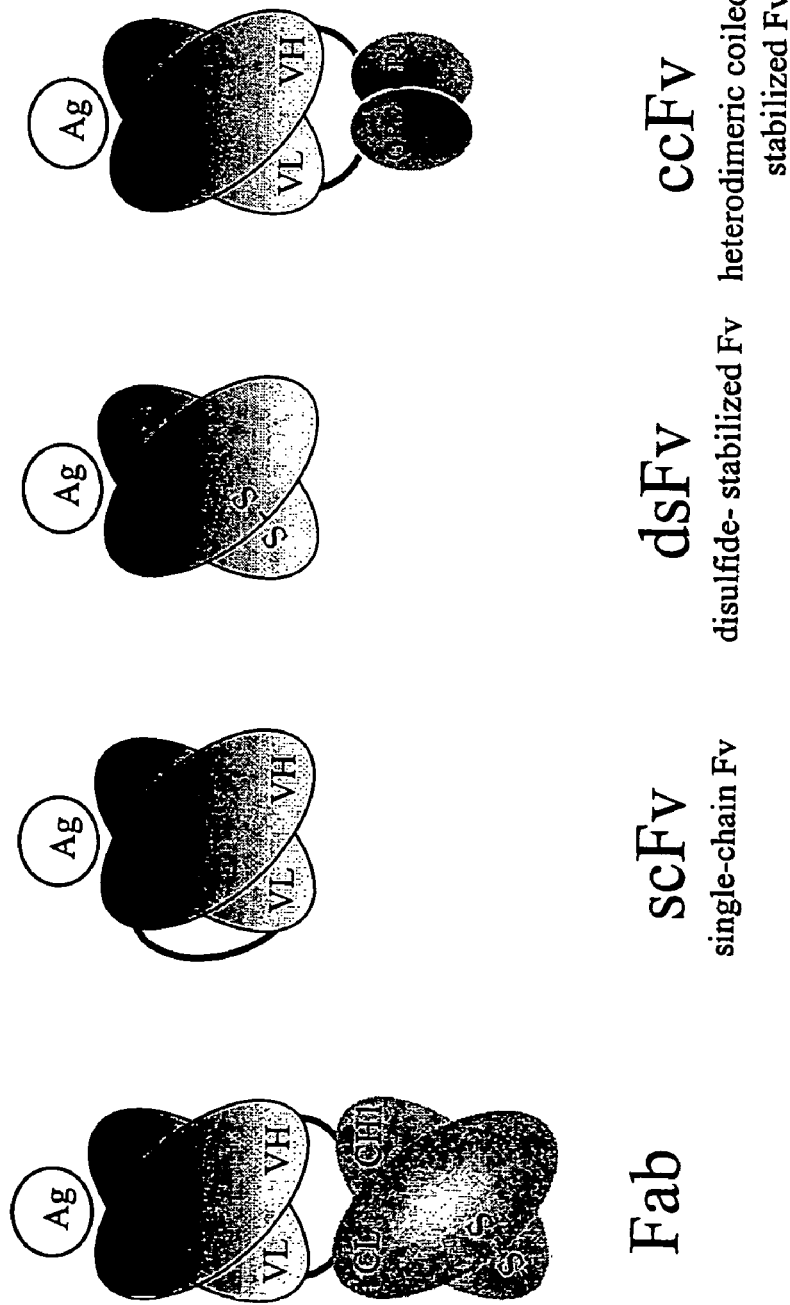

FIG. 24 is a schematic representation depicting various antigen-binding units.

Figure 25A:
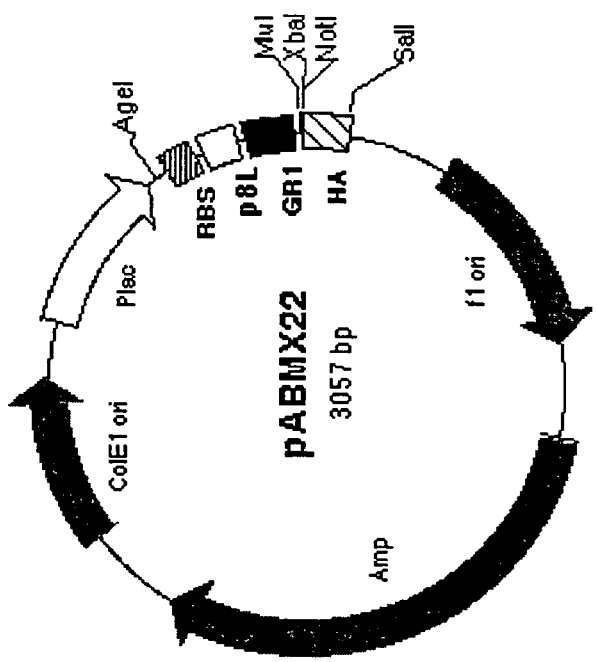

FIG. 25A is a schematic representation of the bacterial expression vector pABMX22. FIG. 25B depicts the complete nucleotide sequence of pABMX22 (SEQ ID NO: 22). The vector contains an ampicillin-resistance gene for antibiotic selection (AMP), a plasmid replication origin (ColE1 ori), the f1 phage replication origin (f1 ori), and the lac promoter/lac O1 driving the expression of downstream sequence plac-RBS-p8L-GR1-HA. The MluI/XbaI or MluI/NotI or XbaI/NotI restriction sites can be used to insert exogenous sequence for display on a bacterial cell.

Figure 26A:
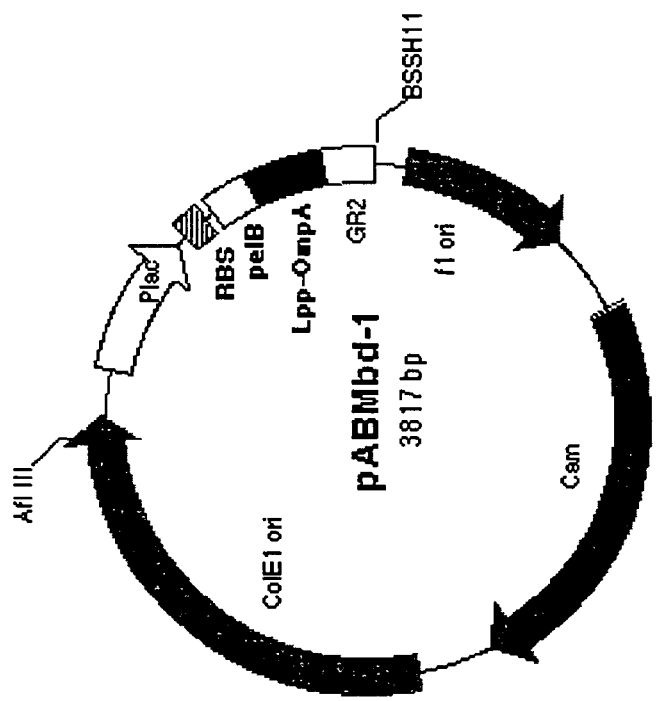

FIG. 26A is a schematic representation of the bacterial helper vector pABMbd-1. FIG. 26B depicts the complete nucleotide sequence of pABMbd-1 (SEQ ID NO: 23). The vector contains a chloramphenicol-resistance gene for antibiotic selection (Cam), a plasmid replication origin (ColE1 ori), the f1 phage replication origin (f1 ori), and the lac promoter/lac O1 driving the expression of downstream sequence plac-RBS-pelB-Lpp-OmpA-GR2.

MODE(S) FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., PHAGE DISPLAY OF PEPTIDES AND PROTEINS (B. K. Kay et al., 1996); PHAGE DISPLAY, A LABORATORY MANUAL (C. F. Barbas III et al., 2001) Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

Definitions:

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A polypeptide or amino acid sequence "derived from" a designated protein refers to the origin of the polypeptide. Preferably, the polypeptide have an amino acid sequence that is essentially identical to that of a polypeptide encoded in the sequence, or a portion thereof wherein the portion consists of at least 10-20 amino acids, preferably at least 20-30 amino acids, more preferably at least 30-50 amino acids, or which is immunologically identifiable with a polypeptide encoded in the sequence. This terminology also includes a polypeptide expressed from a designated nucleic acid sequence.

A "chimeric" protein contains at least one fusion polypeptide comprising regions in a different position in the sequence than that occurs in nature. The regions may normally exist in separate proteins and are brought together in the fusion polypeptide; or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship.

A "multimeric protein" as used herein refers to a globular protein containing more than one separate polypeptide or protein chain associated with each other to form a single globular protein in vitro or in vivo. The multimeric protein may consist of more than one polypeptide of the same kind to form a "homomultimer." Alternatively, the multimeric protein may also be composed of more than one polypeptide of distinct sequences to form a "heteromultimer." Thus, a "heteromultimer" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where more than two polypeptides are present. Exemplary structures for the heteromultimer include heterodimers (e.g. Fv and Fab fragments, diabodies, $GABA_B$ receptors 1 and 2 complexes), trimeric G-proteins, heterotetramers (e.g. $F(ab')_2$ fragments) and further oligomeric structures.

A "ligand" refers to a molecule capable of being bound by the ligand-binding domain of a receptor. The molecule may be chemically synthesized or may occur in nature.

An "agonist" is a molecule capable of stimulating the biological activity of a signaling molecule, e.g., a receptor.

An "antagonist" is a molecule capable of inhibiting the biological activity of a receptor.

By "pairwise interaction" is meant that the two adapters can interact with and bind to each other to form a stable complex. The stable complex must be sufficiently long-lasting to permit packaging the polypeptide onto the outer surface of a genetic package. The complex or dimer must be able to withstand whatever conditions exist or are introduced between the moment of formation and the moment of detecting the displayed polypeptide, these conditions being a function of the assay or reaction which is being performed.

"Monovalent display" refers to expression of a single copy of the exogenous polypeptide per genetic package. In a monovalent phage display system, the collection of phage particles on average carries zero to one exogenous polypeptide per phage particle. By contrast, "multivalent display" refers to the expression of more than one copy of the exogenous polypeptide per genetic package. Thus, in a multivalent phage display system, the collection of phage particles on average carries more than one copy of the exogenous polypeptide.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units" ("Abus"). Abus can be broadly divided into "single-chain" ("Sc") and "non-single-chain" ("Nsc") types based on their molecular structures.

Also encompassed within the terms "antibodies" and "Abus" are immunoglobulin molecules of a variety of species origins including invertebrates and vertebrates. The term "human" as applies to an antibody or an Abu refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

"Non-single-chain antigen-binding unit" ("Nsc Abus") are heteromultimers comprising a light-chain polypeptide and a heavy-chain polypeptide. Examples of the Nsc Abus include but are not limited to (1) a ccFv fragment (FIG. 24) stabilized by the heterodimerization sequences disclosed herein; (2) any other monovalent and multivalent molecules comprising at least one ccFv fragment as described herein; (3) an Fab fragment consisting of the VL, VH, CL and CH1 domains; (4) an Fd fragment consisting of the VH and CH1 domains; (5) an Fv fragment consisting of the VL and VH domains of a single arm of an antibody; (6) an F(ab')2 fragment, a bivalent fragment comprising two Fab fragments linked by a disulfide bridge at the hinge region; (7) a diabody; and (8) any other Nsc Abus that are described in Little et al. (2000) Immunology Today.

As noted above, a Nsc Abus can be either "monovalent" or "multivalent." Whereas the former has one binding site per antigen-binding unit, the latter contains multiple binding sites capable of binding to more than one antigen of the same or different kind. Depending on the number of binding sites, a Nsc Abus may be bivalent (having two antigen-binding sites), trivalent (having three antigen-binding sites), tetravalent (having four antigen-binding sites), and so on.

Multivalent Nsc Abus can be further classified on the basis of their binding specificities. A "monospecific" Nsc Abu is a molecule capable of binding to one or more antigens of the same kind. A "multispecific" Nsc Abu is a molecule having binding specificities for at least two different antigens. While such molecules normally will only bind two distinct antigens (i.e. bispecific Abus), antibodies with additional specificities such as trispecific antibodies are encompassed by this expression when used herein. Examples of bispecific antigen binding units include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific Abus with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); bispecific Abus which can be used as fibrinolytic agents such as anti-fibrin/anti-tissue plasminogen activator (tPA), anti-fibrin/anti-urokinase-type plasminogen activator (uPA); bispecific antigen-binding units for targeting immune complexes to cell surface receptors such as anti-low density lipoprotein (LDL)/anti-Fc receptor (e.g. FcγRI, FcγRII or FcγRIII); bispecific Abus for use in therapy of infectious diseases such as anti-CD3/anti-herpes simplex virus (HSV), anti-T-cell receptor:CD3 complex/anti-influenza, anti-FcγR/anti-HIV; bispecific Abus for tumor detection in vitro or in vivo such as anti-CEA/anti-EOTUBE, anti-CEA/anti-DPTA, anti-p185$^{HER2}$/anti-hapten; BsAbs as vaccine adjuvants; and bispecific Abus as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase. Examples of trispecific antibodies include anti-CD3/anti-CD4/anti-CD37, anti-CD3/anti-CD5/anti-CD37 and anti-CD3/anti-CD8/anti-CD37.

Single-chain antigen-binding unit" ("Sc Abu") refers to a monomeric Abu. Although the two domains of the Fv fragment are coded for by separate genes, a synthetic linker can be made that enables them to be made as a single protein chain (i.e. single chain Fv ("scFv") as described in Bird et al. (1988) *Science* 242:423-426 and Huston et al. (1988) *PNAS* 85:5879-5883) by recombinant methods.

A "repertoire of antigen-binding units" refers to a plurality of antigen-binding units, at least two of which exhibit distinct binding specificities. A genetically diverse repertoire of antigen-binding units refers to a plurality of antigen-binding units, the majority and if not all of the antigen-binding units exhibit unique binding specificities with respect to each other. Genetically diverse repertoire typically has a complexity of at least $10^6$ to $10^{13}$, preferably between $10^7$ to $10^9$, more preferably between $10^8$ to $10^{10}$, even more preferably between $10^8$ to $10^{11}$ distinct antigen-binding units.

An antibody or Abu "specifically binds to" or "immunoreactive with" an antigen if it binds with greater affinity or avidity than it binds to other reference antigens including polypeptides or other substances.

An Abu is displayed "on the surface of a host cell" when the Abu is presented at the outer surface of a host cell. The displayed Abu may be directly attached to the outer surface of the host cell, or may be indirectly attached to the host cell via a host cell bound genetic package such as phage particle.

As used herein, "outer-surface sequences" refer to nucleotide sequences that encode "outer-surface proteins" of a genetic package. These proteins form a proteinaceous coat that encapsulates the genome of the genetic package. Typically, the outer-surface proteins direct the package to assemble the polypeptide to be displayed onto the outer surface of the genetic package, e.g. phage or bacteria.

The term "wildtype" as applied to a gene or a protein, refers to "naturally occurring," "native" gene or protein. These terms include full-length and processed polynucleotides and polypeptides that are naturally found in a cell or a genetic package. The term "wildtype outer-surface proteins" refers to those proteins forming the coat of naturally occurring genetic package, whether it is viruses, cells, or spores. In the case of filamentous bacteriophage, the wildtype proteins are gene III protein (pIII), gene VI protein (pVI), gene VII protein (pVII), gene VIII protein (pVIII), and gene IX protein (pIX).

"Antigen" as used herein means a substance that is recognized and bound specifically by an antibody. Antigens can include peptides, proteins, glycoproteins, polysaccharides and lipids; portions thereof and combinations thereof.

As used herein, the term "surface antigens" refers to the plasma membrane components of a cell. It encompasses integral and peripheral membrane proteins, glycoproteins, polysaccharides and lipids that constitute the plasma membrane. An "integral membrane protein" is a transmembrane protein that extends across the lipid bilayer of the plasma membrane of a cell. A typical integral membrane protein consists of at least one "membrane spanning segment" that generally comprises hydrophobic amino acid residues. Peripheral membrane proteins do not extend into the hydrophobic interior of the lipid bilayer and they are bound to the membrane surface by noncovalent interaction with other membrane proteins.

The terms "membrane", "cytosolic", "nuclear" and "secreted" as applied to cellular proteins specify the extracellular and/or subcellular location in which the cellular protein is mostly, predominantly, or preferentially localized. "Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements, i.e., signaling molecules, governing a variety of biological functions.

A "heterodimeric receptor" encompasses cellular proteins composed of two proteinaceous subunits which exhibits binding affinity to a ligand. The two proteinaceous subunits are distinct molecules which differ in amino acid sequence by at least one amino acid residue. Non-limiting illustrative heterodimeric receptors are those that bind to growth factors (e.g. heregulin), neurotransmitters (e.g. γ-Aminobutyric acid), and other organic or inorganic small molecules (e.g. mineralocorticoid, glucocorticoid). Preferred heterodimeric receptors are nuclear hormone receptors (Belshaw et al. (1996) *Proc. Natl. Acad. Sci. U. S. A* 93(10):4604-4607), erbB3 and erbB2 receptor complex, and G-protein-coupled receptors including but not limited to opioid (Gomes et al. (2000) *J. Neuroscience* 20(22): RC110); Jordan et al. (1999) *Nature* 399:697-700), muscarinic, dopamine, serotonin, adenosine/dopamine, and $GABA_B$ families of receptors.

"Domain" refers to a portion of a protein that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain. A "membrane anchorage domain" refers to the portion of a protein that mediates membrane association. Generally, the membrane anchorage domain is composed of hydrophobic amino acid residues. Alternatively, the membrane anchorage domain may contain modified amino acids, e.g. amino acids that are attached to a fatty acid chain, which in turn anchors the protein to a membrane.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cysteine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring the polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (OFRs) to form a continuous longer OFR, in a manner that maintains the correct reading frame of the original OFRs. Thus, the resulting recombinant fusion protein is a single protein containing two or more segments that correspond to polypeptides encoded by the original OFRs (which segments are not normally so joined in nature.) Although the reading frame is thus made continuous throughout the fused segments, the segments may be physically or spatially separated by, for example, in-frame linker sequence (e.g. "flexon").

"Flexon" as used herein, refers to a flexible polypeptide linker (or a nucleic acid sequence encoding such a polypeptide) which typically comprises amino acids having small side chains (e.g. glycine, alanine, valine, leucine, isoleucine, and serine). Incorporating flexons between one or more sites of the subject fusions may promote functionality by allowing them to assume a conformations relatively independent of each other.

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

"Heterologous" means derived from a genotypically distinct entity from the rest of the entity to which it is being compared. For example, a promoter removed from its native coding sequence and operatively linked to a coding sequence other than the native sequence is a heterologous promoter. The term "heterologous" as applied to a polynucleotide, a polypeptide, means that the polynucleotide or polypeptide is derived from a genotypically distinct entity from that of the rest of the entity to which it is being compared. For instance, a heterologous polynucleotide or antigen may be derived from a different species origin, different cell type, and the same type of cell of distinct individuals.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "fusion gene" is a gene composed of at least two heterologous polynucleotides that are linked together.

A gene "database" denotes a set of stored data which represent a collection of sequences including nucleotide and peptide sequences, which in turn represent a collection of biological reference materials.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

A "replicon" refers to a polynucleotide comprising an origin of replication (generally referred to as an ori sequence) which allows for replication of the polynucleotide in an appropriate host cell. Examples of replicons include episomes (such as plasmids), as well as chromosomes (such as the nuclear or mitochondrial chromosomes).

"Signal transduction" is a process during which stimulatory or inhibitory signals are transmitted into and within a cell to elicit an intracellular response. A "modulator of a signal transduction pathway" refers to a compound which modulates the activity of one or more cellular proteins mapped to the same specific signal transduction pathway. A modulator may augment or suppress the activity of a signaling molecule.

Adapter-Directed Display System of the Present Invention

A central aspect of the present invention is the design of display systems that permit display on genetic packages of an exogenous polypeptide or a library of random or predetermined polypeptides, which is unlinked to any functional outer-surface sequences via peptide bonds. The subject systems avoid all drawbacks associated with expression of the outer-surface proteins by the expression vectors. The experimental design is particularly useful for presenting and/or selecting proteins with desired properties presented by genetic packages such as viruses, cells and spores.

The subject display systems comprise two components: (1) an expression vector that carries an exogenous gene of interest encoding a polypeptide to be displayed on the outer surface of a genetic package; and (2) a helper vector that facilitates the display of the polypeptide of particular interest. Distinguished from the previously reported display systems, the subject systems have the following unique features. First, the expression vector comprises a coding sequence encoding the exogenous polypeptide to be displayed fused in-frame with a first adapter. Second, the expression vector is devoid of outer-surface sequences that encode any functional outer-surface proteins of the genetic package. Third, the helper vector comprises all outer-surface sequences necessary for packaging the genetic package, at least one of the outer-surface sequences being fused in-frame to a second adapter sequence, and wherein the display of the exogenous polypeptide is mediated by pairwise interaction between the first and second adapters.

In one embodiment, the present invention provides a phage display system comprising a phagemid expression vector and a phage helper vector having the aforementioned characteristics. In another embodiment, the present invention provides a bacterial display system in which the bacterial expression vector and the bacterial helper vector exhibit the claimed features. The experimental design of the phage and bacterial display systems can be extended to the construction of eukaryotic expression systems such as a mammalian cell display system.

Phage Display System of the Present Invention:

As noted above, previously reported phage display systems have a number of pronounced disadvantages. For instance, the commonly employed gene III and gene VIII systems bear several intrinsic drawbacks. Among them are (1) toxicity to the host cells as a result of expressing the exogenous polypeptide as a fusion with certain outer-surface proteins of the genetic package; (2) strict limitation on the size and orientation of the exogenous polypeptide to be displayed because certain regions of the outer-surface proteins are required for packaging the exogenous polypeptide onto the genetic package; and (3) instability of the fusion product due to recombination between the fusion and the wildtype outer-surface protein that is typically provided by a helper vector. The recently reported "cysteine-coupled" display system (WO 01/05950) avoids the expression of outer-surface protein fusions via peptide bond, but still fails to minimize the toxicity of these proteins to the host cells. Moreover, one particularly design, namely the two-vector system described in WO 01/05950, inevitably produces mispackaged vectors upon infection of the helper phages. The mispackaged vector contains the outer-surface sequences but not the exogenous gene. The subject phage display systems avoid these shortcomings and provide other related advantages.

A central aspect of the subject design is the separation of the exogenous polypeptide from the outer-surface proteins required for phage packaging. Thus, the phagemid vector (expression vector) carrying exogenous polypeptide does not contain any sequences that encode functional outer-surface proteins. The presentation of the exogenous polypeptide on the surface of the phage particle is mediated by the pairwise interaction of two adapters. One of the adapters is fused in-frame with the exogenous polypeptide encoded by the phagemid vector, and the other is fused in-frame with at least one outer-surface proteins encoded by the helper phage vector. When the host cell carrying the phagemid vector is infected with the helper phage, the encoded exogenous polypeptide forms a complex with the outer-surface protein via pairwise interaction between the respective adapters. The complex is then packaged into surface sheath of the phage, leaving the exogenous polypeptide exposed on its outer surface.

General Characteristics of the Phagemid Vectors of Tile Present Invention:

Several factors apply to the construction of the subject phage display systems. First, the phagemid vector does not contain sequences that encode any functional outer-surface proteins of the genetic package on which the polypeptide is to be displayed. By "functional" is meant that the encoded outer-surface proteins retain the ability to facilitate or direct the genetic package to assemble the polypeptide of interest onto its outer surface. The precise outer-surface sequences to be excluded from the expression vectors will depend on the choice of phage packages.

As used herein, the term "phage" encompasses viruses consisting of a protein coat encapsulated therein a viral genome required for viral replication. The viral genome may be composed of DNA or RNA, single or double stranded, linear or circular. The phages may infect a wide range of host cells, including but not limited to prokaryotes such as bacterial cells. The genomes of many phages, filamentous or non-filamentous, have been sequenced. Representative filamentous phages include M13, fl, fd, Ifl, Ike, Xf, Pf1, and Pf3. Within the class of filamentous phages, M13 is the most well-characterized species. Its 3-dimentional structure is known, and the functions of its coat proteins are well understood. Specifically, the M13 genome encodes five coat proteins, namely pIII, VIII, VI, VII and IX. For constructing an M13-based expression vector of the subject phage display system, all of the coat-encoding sequences must be deleted, or altered so that the encoded protein products are incapable of effecting the presentation of the exogenous polypeptide onto the outer surface of a phage particle. Suitable modifications to a functional outer-surface protein may result in: (1) loss of functional signal peptide that directs the intracellular translocation of the outer-surface protein into the periplasm of the bacterial cells, where the signal peptide is then cleaved off; (2) loss of function of the coat protein domain that anchors the mature polypeptide into the bacterial cell membrane and/or phage coat; (3) loss of function of the coat protein domain that specifically binds to the phage receptor, the F-pilus of the host bacterium; and/or (4) introduction of internal stop codons to prevent expression of any functional coat proteins. These and other domains within several coat proteins, such as pIII, have been delineated (see, e.g. U.S. Pat. No. 5,969,108). The outer-surface proteins of other closely related members such as fl and fd filamentous phages are also well known in the art (see, e.g. Kay et al. (1996) Phage Display of Peptides and Protiens: A Laboratory Manual. Academic Press., Inc. San Diego). Preferably, the only phage sequence presented in an M13-based expression vector contains fl origin required for phagemid replication and package. A stepwise illustration on constructing an M13-based expression vector is detailed in Examples 1-4. Thus, one of ordinary skill in the art can readily construct an expression vector with the claimed features without undue experimentation.

Similar constructions can be made with other filamentous phage. Pf3 is another well-known filamentous phage that infects *Pseudomonas aerugenosa* cells that harbor an IncP-1 plasmid. The entire genome of Pf3 has been sequenced and the genetic signals involved in replication and assembly have been characterized (Luiten et al. (1985) *J. Virology* 56 (1): 268-276). The major coat protein of Pf3 is unusual in having no signal peptide to direct its secretion. The sequence has charged residues $ASP_7$, $ARG_{37}$, $LYS_{40}$, and $PHE_{44}$-$COO^-$ which is consistent with the amino terminus being exposed. The viral strand replication origin of 139 bp DNA for Pf3 phage has also been identified (Luiten et al. (1991) *J. Bacteriol* 173(13): 4007-4012). To construct a Pf3-based expression vector, the Pf3 coat-encoding sequence must be deleted or altered so that no functional major coat protein is encoded. A preferred expression vector only contains the Pf3 phage replication origin for its replication and packaging.

The same approach applies to construction of phagemid vectors derived from non-filamentous phages. Non-limiting representative members of this class of phages are bacteriophage ΦX174, λ, T4 and T7. The bacteriophage ΦX174 is a very small icosahedral virus which has been thoroughly studied by genetics, biochemistry, and electron microscopy. Three gene products of ΦX174 are present on the outside of the mature virion: F (capsid), G (major spike protein, 60 copies per virion), and H (minor spike protein, 12 copies per virion). The G protein comprises 175 amino acids, while H comprises 328 amino acids. The F protein interacts with the single-stranded DNA of the virus. The proteins F, G, and H are translated from a single mRNA in the viral infected cells. Thus, an exemplary expression vector based on this class of non-filamentous phage lacks all coding sequences of the F, G and H proteins. Other alternative expression vectors comprise altered F-, G-, or H-encoding sequences that do not yield functional F, G and H proteins.

General Characteristics of the Helper Phage Vectors of the Present Invention:

The second component of the subject phage display systems is a helper vector that functions to complement the expression vectors devoid of any functional outer-surface sequences. Unlike previously described helper vectors (U.S. Pat. No. 5,969,108) that either lack one of the necessary coat-protein encoding sequences, or contain a sequence encoding a defective coat protein of the genetic package, the subject helper vectors provide all of the outer-surface sequences required for packaging the genetic package. The precise outer-surface sequences employed again depend on the choice of the phage packages.

As mentioned above, a wealth of structural and biochemical information on a variety of phages is available in the art. The gene sequences encoding structural proteins and enzymes required for replicating and packaging numerous types of genetic package have been identified, and widely used to construct prior display systems (U.S. Pat. Nos. 6,248, 516, 5,969,108, 5,885,793, 5,837,500, 5,571,698, 5,223,409, 5,514,548, WO9005144, EP0368684, WO09201047, WO09311236, and WO09708320). These sequences are generally applicable for constructing the subject helper vectors exhibiting additional unique features.

Specifically, the subject helper phage vector generally comprises all outer-surface sequences responsible for encapsulating both the helper phage and the phagemid vector. In one aspect, the helper phage vector comprises outer-surface sequences encoding all coat proteins of one of the following filamentous phages M13, f1, fd, Ifl, Ike, Xf, Pf1, and Pf3. Preferred coat-encoding sequences of an M13-based helper phage vector are gIII, gIII, gVI, gVII, gIX or their functional equivalents. In another aspect, the helper phage vector contains coat encoding sequences of a non-filamentous phage selected from the group consisting of bacteriophage ΦX174, λ, T4 and T7. In addition to these structural proteins, the helper phage vector typically encodes other phage-derived enzymes that act in trans on the phage origins of replication carried on both the phagemid vector and helper phage to "help" replicate and package the phagemid vector. A preferred M13 helper vector of the present invention is replication-defective, so as to ensure preferential packaging of the phagemid vectors. Preferably, more than 90% of the packaged vectors are phagemid vectors; even more preferably more than 99% of the packaged vectors are phagemid vectors. The preferred M13 helper phage vector further comprises sequences encoding proteins I, II, IV, V, X or functional equivalents. As used herein, the functional equivalents of outer-surface proteins include those coding for modified outer-surface proteins that retain the functionality of the wildtype outer-surface proteins. Functionally equivalent outer-surface proteins include those that enhance, decrease or not significantly affect properties of the corresponding wildtype proteins. These equivalents may be polypeptides having conservative amino acid substitutions, analogs including fusions and mutants. A preferred M13 helper vector is interference-resistant. Exemplary interference-resistant helper vectors are M13KO7 (Amersham Pharmacia Biotech) and in its derivatives such as VCSM13 (Stratagene). These two interference-resistant helper vectors provide the phage sequences necessary for packaging a phage particle.

Figure 5A:
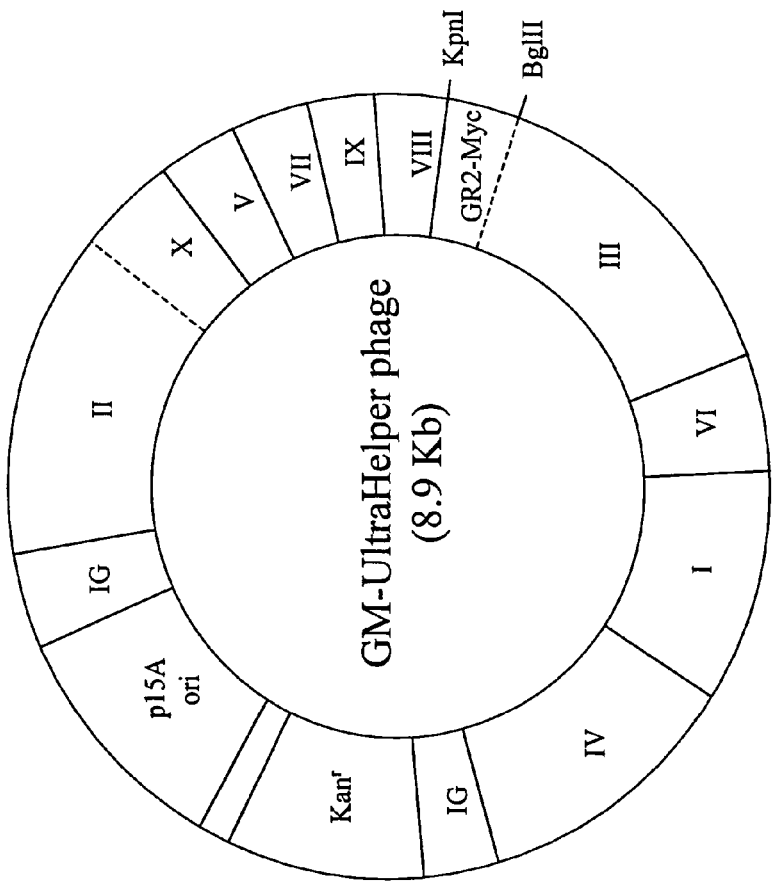
FIG. 5A is a schematic representation of the GM-Ultra-Helper phage.

The helper phage vector of the present invention may contain one or more copies of a given outer-surface sequence, so long as all of the outer-surface sequences necessary for phage packaging are present. The use of one copy of each necessary outer-surface sequence typically yields a "multivalent" phage display system. By contrast, the incorporation of more than one copy of a given outer-surface sequence or its functional equivalent potentially yields a "monovalent" phage display system. Monovalent display allows the discrimination of displayed polypeptides that bind targets with moderate versus high affinity. It also aids in selection of polypeptides such as antibodies, on the basis of affinity by avoiding the "avidity" effect where a phage expressing more than one copy of a low affinity antibody would have the same apparent affinity as a phage expressing one copy of a higher affinity antibody. Multivalent display, however, provides alternative advantages. It is particularly useful in the initial stages of selection of binding polypeptides. At the early stages of screening, it is often preferably to accumulate a broad spectrum of polypeptides as potential leads than to identify a single high-affinity candidate. The polypeptides obtained through the initial screen can then be ordered in terms of their affinities using monovalent display or other methods. The present invention provides an exemplary helper phage vector (FIG. 5A) of a multivalent display system. Upon infecting bacterial cells with the resulting helper phages, the packaged phagemid particles exhibit about two fold more exogenous polypeptide/pIII complex than the free pIII, indicating that the packaged phages have a valency of more than one copy (see Example 2, FIG. 11). Also provided in the present invention is an M13 helper phage vector carrying a copy of the KO7 gene III outer-surface sequence and a copy the C-terminal portion of gene III (FIG. 19A and Example 4). The latter sequence encodes a functional equivalent capable of competing with the wildtype pIII for packaging. The resulting helper phages are expected to yield a monovalent display system.

A particularly preferred helper vector supports both monovalent and multivalent display. Such a helper vector can be constructed by incorporating a suppressible translational stop codon between the first and second copy of an outer-surface sequence, e.g. gene III of M13 phage. The suppressible codon allows the translation of nucleotide sequences downstream of the codon (e.g. gene III) under suppressive condition, but under non-suppressive conditions translation ends at the codon. When the helper phage is grown in suppressive condition, for example in suppressor bacterial strains, the second copy of the outer-surface protein is expressed which competes with the first copy for packaging; a monovalent phage display occurs. However, when the same helper phage is grown in a non-suppressive bacterial strain, the second copy of the outer-surface sequence will not be expressed, and thus yield a multivalent display system. As such, the suppressible codon functions as a convenient "switch" that controls either form of display when subjected to two different conditions. Examples of suppressible translational stop codons are the amber, ochre and opal codons.

General Characteristics of the Adapters of the Present Invention:

A further consideration in constructing the phage display system is to select a pair of adapter sequences that encode two adapters capable of pairwise interaction. Whereas one of the adapter sequences is inserted in-frame with the exogenous sequence carried by the phagemid vector, the other is fused in-frame with at least one of the outer-surface protein of the helper phage vector. By "pairwise interaction" is meant that the two adapters can interact with and bind to each other to form a stable complex. The stable complex must be sufficiently long-lasting to permit packaging the polypeptide onto the outer surface of the genetic package. The complex or dimer must be able to withstand whatever conditions exist or are introduced between the moment of formation and the moment of detecting the displayed polypeptide, these conditions being a function of the assay or reaction which is being performed. For phages (e.g. M13) that are assembled periplasmically, the complex or dimer must be sufficiently stable when residing in the bacterial periplasm, where it is packaged along with the phage genome. The stable complex or dimer may be irreversible or reversible as long as it meets the other requirements of this definition. Thus, a transient complex or dimer may form in a reaction mixture, but it does not constitute a stable complex if it dissociates spontaneously and yields no detectable polypeptide displayed on the outer surface of a genetic package.

The pairwise interaction between the first and second adapters may be covalent or non-covalent interactions. Non-covalent interactions encompass every exiting stable linkage that do not result in the formation of a covalent bond. Non-limiting examples of noncovalent interactions include electrostatic bonds, hydrogen bonding, Van der Waal's forces, steric interdigitation of amphiphilic peptides. By contrast, covalent interactions result in the formation of covalent bonds, including but not limited to disulfide bond between two cysteine residues, C—C bond between two carbon-containing molecules, C—O or C—H between a carbon and oxygen- or hydrogen-containing molecules respectively, and O—P bond between an oxygen- and phosphate-containing molecule.

Adapter sequences applicable for constructing the expression and helper vectors of the subject display system can be derived from a variety of sources. Generally, any protein sequences involved in the formation of stable multimers are candidate adapter sequences. As such, these sequences may be derived from any homomultimeric or heteromultimeric protein complexes. Representative homomultimeric proteins are homodimeric receptors (e.g. platelet-derived growth factor homodimer BB (PDGF), homodimeric transcription factors (e.g. Max homodimer, NF-kappaB p65 (RelA) homodimer), and growth factors (e.g. neurotrophin homodimers). Non-limiting examples of heteromultimeric proteins are complexes of protein kinases and SH2-domain-containing proteins (Cantley et al. (1993) *Cell* 72: 767-778; Cantley et al. (1995) *J. Biol. Chem.* 270(44): 26029-26032), heterodimeric transcription factors, and heterodimeric receptors.

Preferred heterodimeric transcription factors are a-Pal/Max complexes and Hox/Pbx complexes. Hox represents a large family of transcription factors involved in patterning the anterior-posterior axis during embryogenesis. Hox proteins bind DNA with a conserved three alpha helix homeodomain. In order to bind to specific DNA sequences, Hox proteins require the presence of hetero-partners such as the Pbx homeodomain. Wolberger et al. solved the 2.35 Å crystal structure of a HoxB1-Pbx1-DNA ternary complex in order to understand how Hox-Pbx complex formation occurs and how this complex binds to DNA. The structure shows that the homeodomain of each protein binds to adjacent recognition sequences on opposite sides of the DNA. Heterodimerization occurs through contacts formed between a six amino acid hexapeptide N-terminal to the homeodomain of HoxB1 and a pocket in Pbx1 formed between helix 3 and helices 1 and 2. A C-terminal extension of the Pbx1 homeodomain forms an alpha helix that packs against helix 1 to form a larger four helix homeodomain (Wolberger et al. (1999) *Cell* 96: 587-597; Wolberger et al. *J Mol Biol.* 291: 521-530).

A vast number of heterodimeric receptors have also been identified. They include but are not limited to those that bind to growth factors (e.g. heregulin), neurotransmitters (e.g. γ-Aminobutyric acid), and other organic or inorganic small molecules (e.g. mineralocorticoid, glucocorticoid). Preferred heterodimeric receptors are nuclear hormone receptors (Belshaw et al. (1996) *Proc. Natl. Acad. Sci. U.S.A* 93(10): 4604-4607), erbB3 and erbB2 receptor complex, and G-protein-coupled receptors including but not limited to opioid (Gomes et al. (2000) *J. Neuroscience* 20(22): RC110); Jordan et al. (1999) *Nature* 399:697-700), muscarinic, dopamine, serotonin, adenosine/dopamine, and $GABA_B$ families of receptors. For majority of the known heterodimeric receptors, their C-terminal sequences are found to mediate heterodimer formation.

Sequence of antibody chains that are involved in dimerizing the L and H chains can also be used as adapters for constructing the subject display systems. These sequences include but are not limited to constant region sequences of an L or H chain. Additionally, adapter sequences can be derived from antigen-binding site sequences and its binding antigen. In such case, one adapter of the pair contains antigen-binding site amino acid residues that is recognized (i.e. being able to stably associate with) by the other adapter containing the corresponding antigen residues.

Based on the wealth of genetic and biochemical data on vast families of genes, one of ordinary skill will be able to select and obtain suitable adapter sequences for constructing the subject display system without undue experimentation.

Where desired, sequences from novel hetermultimeric proteins can be employed as adapters. In such situation, the identification of candidate sequences involved in formation of heteromultimers can be determined by any genetic or biochemical assays without undue experimentation. Additionally, computer modeling and searching technologies further facilitates detection of heteromultimeric sequences based on sequence homologies of common domains appeared in related and unrelated genes. Non-limiting examples of programs that allow homology searches are Blast (http://www.ncbi.nlm.nih.gov/BLAST/), Fasta (Genetics Computing Group package, Madison, Wis.), DNA Star, Clustlaw, TOFFEE, COBLATH, Genthreader, and MegAlign. Any sequence databases that contains DNA sequences corresponding to a target receptor or a segment thereof can be used for sequence analysis. Commonly employed databases include but are not limited to GenBank, EMBL, DDBJ, PDB, SWISS-PROT, EST, STS, GSS, and HTGS.

The subject adapters that are derived from heterodimerization sequences can be further characterized based on their physical properties. Preferred heterodimerization sequences exhibit pairwise affinity resulting in predominant formation of heterodimers to a substantial exclusion of homodimers. Preferably, the predominant formation yields a heteromultimeric pool that contains at least 60% heterodimers, more preferably at least 80% heterodimers, more preferably between 85-90% heterodimers, and more preferably between 90-95% heterodimers, and even more preferably between 96-99% heterodimers that are allowed to form under physiological buffer conditions and/or physiological body temperatures. In certain embodiments of the present invention, at least one of the heterodimerization sequences of the adapter pair is essentially incapable of forming a homodimer in a physiological buffer and/or at physiological body temperature. By "essentially incapable" is meant that the selected heterodimerization sequences when tested alone do not yield detectable amounts of homodimers in an in vitro sedimentation experiment as detailed in Kammerer et al. (1999) *Biochemistry* 38: 13263-13269), or in the in vivo two-hybrid yeast analysis (see e.g. White et al. *Nature* (1998) 396: 679-682). In addition, individual heterodimerization sequences can be expressed in a host cell and the absence of homodimers in the host cell can be demonstrated by a variety of protein analyses including but not limited to SDS-PAGE, Western blot, and immunoprecipitation. The in vitro assays must be conducted under a physiological buffer conditions, and/or preferably at physiological body temperatures. Generally, a physiological buffer contains a physiological concentration of salt and at adjusted to a neutral pH ranging from about 6.5 to about 7.8, and preferably from about 7.0 to about 7.5. A variety of physiological buffers is listed in Sambrook et al.

(1989) supra and hence is not detailed herein. Preferred physiological conditions are described in Kammerer et al., supra.

An illustrative adapter pair exhibiting the above-mentioned physical properties is $GABA_B$-R1/$GABA_B$-R2 receptors. These two receptors are essentially incapable of forming homodimers under physiological conditions (e.g. in vivo) and at physiological body temperatures. Research by Kuner et al. and White et al. (*Science* (1999) 283: 74-77); *Nature* (1998) 396: 679-682)) has demonstrated the heterodimerization specificity of $GABA_B$-R1 and $GABA_B$-R2 in vivo. In fact, White et al. were able to clone $GABA_B$-R2 from yeast cells based on the exclusive specificity of this heterodimeric receptor pair. In vitro studies by Kammerer et al. supra has shown that neither $GABA_B$-R1 nor $GABA_B$-R2 C-terminal sequence is capable of forming homodimers in physiological buffer conditions when assayed at physiological body temperatures. Specifically, Kammerer et al. have demonstrated by sedimentation experiments that the heterodimerization sequences of $GABA_B$ receptor 1 and 2, when tested alone, sediment at the molecular mass of the monomer under physiological conditions and at physiological body temperatures (e.g. at 37° C.). When mixed in equimolar amounts, $GABA_B$ receptor 1 and 2 heterodimerization sequences sediment at the molecular mass corresponding to the heterodimer of the two sequences (see Table 1 of Kammerer et al.). However, when the $GABA_B$-R1 and $GABA_B$-R2 C-terminal sequences are linked to a cysteine residue, homodimers may occur via formation of disulfide bond.

Adapters can be further characterized based on their secondary structures. Preferred adapters consist of amphiphilic peptides that adopt a coiled-coil helical structure. The helical coiled coil is one of the principal subunit oligomerization sequences in proteins. Primary sequence analysis reveals that approximately 2-3% of all protein residues form coiled coils (Wolf et al. (1997) *Protein Sci.* 6:1179-1189). Well-characterized coiled-coil-containing proteins include members of the cytoskeletal family (e.g. α-keratin, vimentin), cytoskeletal motor family (e.g. myosine, kinesins, and dyneins), viral membrane proteins (e.g. membrane proteins of Ebola or HIV), DNA binding proteins, and cell surface receptors (e.g. $GABA_B$ receptors 1 and 2). Coiled-coil adapters of the present invention can be broadly classified into two groups, namely the left-handed and right-handed coiled coils. The left-handed coiled coils are characterized by a heptad repeat denoted "abcdefg" with the occurrence of apolar residues preferentially located at the first (a) and fourth (d) position. The residues at these two positions typically constitute a zig-zag pattern of "knobs and holes" that interlock with those of the other stand to form a tight-fitting hydrophobic core. In contrast, the second (b), third (c) and sixth (f) positions that cover the periphery of the coiled coil are preferably charged residues. Examples of charged amino acids include basic residues such as lysine, arginine, histidine, and acidic residues such as aspartate, glutamate, asparagine, and glutamine. Uncharged or apolar amino acids suitable for designing a heterodimeric coiled coil include but are not limited to glycine, alanine, valine, leucine, isoleucine, serine and threonine. While the uncharged residues typically form the hydrophobic core, inter-helical and intra-helical salt-bridge including charged residues even at core positions may be employed to stabilize the overall helical coiled-coiled structure (Burkhard et al. (2000) *J. Biol. Chem.* 275:11672-11677). Whereas varying lengths of coiled coil may be employed, the subject coiled coil adapters preferably contain two to ten heptad repeats. More preferably, the adapters contain three to eight heptad repeats, even more preferably contain four to five heptad repeats.

In designing optimal coiled-coil adapters, a variety of existing computer software programs that predict the secondary structure of a peptide can be used. An illustrative computer analysis uses the COILS algorithm which compares an amino acid sequence with sequences in the database of known two-stranded coiled coils, and predicts the high probability coiled-coil stretches (Kammerer et al. (1999) *Biochemistry* 38:13263-13269).

While a diverse variety of coiled coils involved in multimer formation can be employed as the adapters in the subject display system. Preferred coiled coils are derived from heterodimeric receptors. Accordingly, the present invention encompasses coiled-coil adapters derived from $GABA_B$ receptors 1 and 2. In one aspect, the subject coiled coils adapters comprise the C-terminal sequences of $GABA_B$ receptor 1 and $GABA_B$ receptor 2. In another aspect, the subject adapters are composed of two distinct polypeptides of at least 30 amino acid residues, one of which is essentially identical to a linear sequence of comparable length depicted in FIG. 23 (GR1), and the other is essentially identical to a linear peptide sequence of comparable length depicted in FIG. 23 (GR2).

Another class of preferred coiled coil adapters are leucine zippers. The leucine zipper have been defined in the art as a stretch of about 35 amino acids containing 4-5 leucine residues separated from each other by six amino acids (Maniatis and Abel, (1989) *Nature* 341:24). The leucine zipper has been found to occur in a variety of eukaryotic DNA-binding proteins, such as GCN4, C/EBP, c-fos gene product (Fos), c-jun gene product (Jun), and c-Myc gene product. In these proteins, the leucine zipper creates a dimerization interface wherein proteins containing leucine zippers may form stable homodimers and/or heterodimers. Molecular analysis of the protein products encoded by two proto-oncogenes, c-fos and c jun, has revealed such a case of preferential heterodimer formation (Gentz et al., (1989) *Science* 243:1695; Nakabeppu et al., (1988) *Cell* 55:907; Cohen et al., (1989) *Genes Dev.* 3:173). Synthetic peptides comprising the leucine zipper regions of Fos and Jun have also been shown to mediate heterodimer formation, and, where the amino-termini of the synthetic peptides each include a cysteine residue to permit intermolecular disulfide bonding, heterodimer formation occurs to the substantial exclusion of homodimerization.

The leucine-zipper adapters of the present invention have the general structural formula known as the heptad repeat (Leucine-$X_1$-$X_2$-$X_3$-$X_4$-$X_5$-$X_6$)$_n$ (SEC) ID NO: 31), where X may be any of the conventional 20 amino acids, but are most likely to be amino acids with alpha-helix forming potential, for example, alanine, valine, aspartic acid, glutamic acid, and lysine, and n may be 2 or greater, although typically n is 3 to 10, preferably 4 to 8, more preferably 4 to 5. Preferred sequnes are the Fos or Jun leucine zippers.

As used herein, a linear sequence of peptide is "essentially identical" to another linear sequence, if both sequences exhibit substantial amino acid or nucleotide sequence homology. Generally, essentially identical sequences are at least about 60% identical with each other, after alignment of the homologous regions. Preferably, the sequences are at least about 70% identical; more preferably, they are at least about 80% identical; more preferably, they are at least about 90% identical; more preferably, the sequences are at least about 95% identical; still more preferably, the sequences are 100% identical.

In determining whether polypeptide sequences are essentially identical, a sequence that preserves the functionality of the polypeptide with which it is being compared is particularly preferred. Functionality may be established by different criteria, such as ability to form a stable complex with a pairing adapter, and ability to facilitate display of polypeptides fused in-frame with the adapter.

The subject adapters include modified leucine zippers and $GABA_B$ heterodimerization sequences which are functionally equivalent to the polypeptide sequences exemplified herein. Modified polypeptides providing improved stability to the paired adapters and/or display efficiency are preferred. Examples of modified polypeptides include those with conservative substitutions of amino acid residues, and one or more deletions or additions of amino acids which do not significantly deleteriously alter the heterodimerization specificity. Substitutions can range from changing or modifying one or more amino acid residues to complete redesign of a region as long as the pairwise interaction is maintained. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention can be in glycosylated or unglycosylated form, can be modified post-translationally (e.g., acetylation, and phosphorylation) or can be modified synthetically (e.g., the attachment of a labeling group).

The adapter sequences of the present invention can be obtained using conventional recombinant cloning methods and/or by chemical synthesis. Using well-established restriction and ligation techniques, the appropriate adapter sequences can be excised from various DNA sources and integrated in-frame with the exogenous gene sequences and the outer-surface sequences to generate the expression and helper vectors, respectively.

Figure 9A:
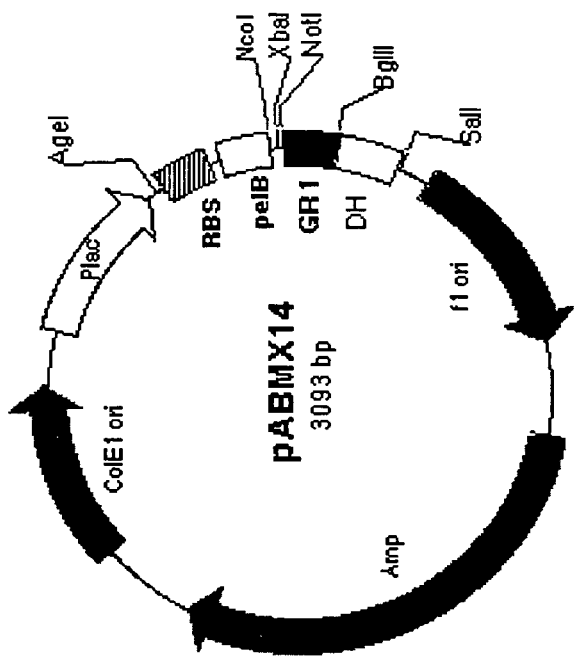
FIG. 9A is a schematic representation of vector pABMX14.

Preferably, the first adapter sequence is inserted into the expression vector in such a way to minimize structural interference, if any, on the resulting exogenous fusion polypeptide. Whereas the first adapter can be fused to the 5' or 3' of the exogenous gene sequence, FIG. 9A depicts a preferred phagemid vector in which the adapter sequence (i.e. hererodimerization sequence derived from $GABA_B$ receptor 1) is fused in-frame to the 3' end of the exogenous gene sequence.

Similarly, the second adapter sequence is inserted into the helper vector in a position where the integrity of the expressed phage coat is not undermined. The adapter sequence can be fused to the 5' or 3' end of an outer-surface sequence without disrupting the coding region. FIGS. 5 and 19 depict two preferred helper phage vectors in which the adapter sequence (i.e. heterodimerizeration sequence derived from $GABA_B$ receptor 2) is placed in-frame to the 5' end of the outer-surface sequence, gene III or a functional portion thereof.

Bacterial Display System of the Present Invention:

The present invention also provides a bacterial display system comprising the following two components: (1) a bacterial expression vector that carries an exogenous gene of interest encoding an exogenous polypeptide to be displayed on the outer surface of a bacterial cell or bacterial spore; and (2) a helper vector that facilitates the display of the polypeptide of particular interest. Unlike the previously described bacterial systems in which the exogenous polypeptide is expressed as a fusion with a bacterial outer-surface protein, the subject bacterial systems have the following unique features. First, the bacterial expression vector comprises a coding sequence encoding the exogenous polypeptide to be displayed fused in-frame with a first adapter. Second, the bacterial expression vector is devoid of outer-surface sequences that encode functional outer-surface proteins of a bacterial or bacterial spore. Third, the helper vector comprises all outer-surface sequences necessary for packaging the genetic package, at least one of the outer-surface sequences being fused in-frame to a second adapter sequence, and wherein the display of the exogenous polypeptide is mediated by pairwise interaction between the first and second adapters.

The general principle and experimental design outlined above for constructing the subject phage display system are equally applicable for generating the subject bacterial display system. Whereas the bacterial expression vector lacks sequences encoding any functional outer-surface proteins, the helper bacterial vector contains an outer-surface sequence necessary for compensating the deficiency.

The helper bacterial vector typically comprises an outer-surface sequence encoding an outer-surface protein having the following two domains: (1) a signal peptide that directs the protein to be secreted through the lipid bilayer to the periplasm; and (2) a membrane translocating domain capable of locating the outer-surface protein onto the outer surface of a bacterial cell. The expressed outer-surface protein is first transported to the periplasm where the leader peptide is cleaved off. When the outer-surface protein is expressed as a fusion with an adapter, the adapter facilitates the translocation of the exogenous polypeptide that is also present in the periplasm onto the bacterial outer surface upon binding to the paring adapter contained in the exogenous polypeptide.

Prior research has revealed a vast number of bacterial surface-protein encoding sequences that can be used for constructing the helper bacterial expression vector. Non-limiting examples of bacterial surface proteins are LamB (Bremer et al. *Proc. Natl. Acad. Sci U.S.A.* (1984) 81:3830-34; *Gene* (1987) 52:165-73); OmpA (*Prog Biophys Molec Biol* (1987) 49:89-115); OmpC (Misra et al. (1988) *J. Bacteriol* 170:528-33; OmpF (Pages et al. *Biochemimie* (1990) 72:169-76); PhoE (van der Ley et al. *J. Biol. Chem.* 261:12222-5); pilin (So et al. *Curr Top in Microbiol & Immunol* (1985) 118:13-28); pldA (de Geus et al. *EMBO J.* (1984) 3(8): 1799-1802); BtuB, FepA, FhuA, IutA, FecA, and FhuE (Gudmundsdottir et al, (1989) *J. Bacteriol* 171(12):6526-33); GIP-anchored protein INP (Kim et al. (1999) *Lett Appl Microbiol* 29(5):292-297) and β-autotransporter protein AIDA (Veiga et al. (1999) *Mol Microbiol* 33: 1232-1243), and other outer membrane lipoproteins such as TratT, Pal, Opr1, OsmB, NlpB and BlaZ, Numerous coat proteins residing on the surface of bacterial spores have also been identified. Their corresponding gene sequences have subsequently been isolated. For example, Donovan et al. reported the identification of *Bacillus subtilis* spore coat CotD and CotC genes (Donovan et al. (1987) *J. Mol. Biol.* 196:1-10). Characterization of these and other surface proteins are detailed in Pierre Cornelis et al. (2000) *Curr. Opin. Biotech.* 11(5):450-454; Lang et al. (2000) *Int. J. Med. Microbiol.* 290: 579-585; Daugherty et al. (1999) *Protein Engineering* 12 (7): 613-621; U.S. Pat. Nos. 5,837,500 and 5,348,867 as well as the references cited therein.

The signal peptide and the membrane translocation domain of these and other bacterial outer-surface proteins are well known in the art. The signal peptide generally consists of the first 5 to 30 N-terminal amino acids of the protein. The membrane translocation domain typically comprises one or more membrane spanning segments that are readily identifiable via computer-assisted conventional sequence analyses. One of ordinary skill in the art can readily obtain the appropriate polypeptide and nucleotide sequences using conventional synthetic and recombinant technology. Where desired, the signal peptide of one outer-surface protein may be attached in-frame to the membrane translocation domain of another outer-surface protein, or vice versa. It has been shown that such a chimera can be expressed on the bacterial outer surface (U.S. Pat. No. 5,837,500). As such, a signal peptide leader peptide of any one of the above-mentioned bacterial outer-surface proteins can be linked in-frame to the membrane translocation domain of suitable length of any native bacterial outer-surface proteins. Similarly, the translocation domain of any one of the aforementioned outer-surface proteins can be fused in-frame to a signal peptide of any protein of bacterial or other origins, known to be capable of directing the fusion to the bacterial periplasm.

The bacterial expression vector of the present invention lacks sequences encoding any functional bacterial outer-surface proteins. Any of the aforementioned outer-surface sequences are candidate sequences to be excluded while constructing the subject expression vector. As used herein, the term "functional" is meant that the encoded outer-surface proteins retain the ability to facilitate or direct the genetic package to assemble the polypeptide of interest onto its outer surface. The loss of the "function" may be attributed to modification(s) resulting in (1) loss of a functional signal peptide that direct the intracellular translocation of the outer-surface protein into the [periplasm] of the bacterial cells, where the signal peptide is then cleaved off; (2) loss of function of the membrane translocation domain that translocates the mature polypeptide onto the bacterial cell membrane; and/or (3) introduction of internal stop codons to prevent expression of any functional outer-surface proteins.

The two adapter sequences linked to the expression and helper vectors have the same structural and functional characteristics as the ones employed in the subject phage display system. Any adapter sequence applicable for constructing the phage display system is equally suited for generating the bacterial display system. Thus, the criteria and procedures for selecting and preparing the pairing adapters are not repeated in this section.

Suitable bacterial genetic packages include all bacterial strains, which can be grown in culture and can be engineered to display exogenous polypeptide on their outer surface, and are compatible with affinity selection. Preferred genetic packages are gram-negative bacteria. Non-limiting examples of preferred species include *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli.*

Bacterial spores have desirable properties as genetic packages. Spores are much more resistant than vegetative bacterial cells to chemical and physical agents, and hence permit the use of a great variety of test conditions. For instance, bacteria of the genus *Bacillus* form endospores that are extremely resistant to damage by heat, radiation, desiccation, and toxic chemicals (reviewed by Losick et al. *Ann. Rev. Genet.* (1986) 20:625-669). In addition, the *Bacillus* spores neither actively metabolize nor alter the proteins on their surface. This phenomenon is attributed to extensive intermolecular crosslinking of the coat proteins. Other spores useful as genetic packages are exospores, such as spores of *Streptomyces.*

Other Consideration for Constructing the Subject Phage and Bacterial Display Systems The vectors of the present invention generally comprise transcriptional or translational control sequences required for expressing the exogenous polypeptide. Suitable transcription or translational control sequences include but are not limited to replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes and the genetic packages are phage particles, the expression vector typically comprises two ori sequences, one directing autonomous replication of the vector within the prokaryotic cells, and the other ori supports packaging of the phage particles. Preferred prokaryotic ori is capable of directing vector replication in bacterial cells. Non-limiting examples of this class of on include pMB1, pUC, as well as other *E. Coli* origins. Preferred ori supporting packaging of the phage particles includes but is not limited to fl ori, Pf3 phage replication on.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For prokaryotic cells, a variety of robust promoters are known in the art. Preferred promoters are lac promoter, Trc promoter, T7 promoter and pBAD promoter.

Suitable promoter sequences for other eukaryotic cells include the promoters for 3-phosphoglycerate kinase, or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In constructing the subject vectors, the termination sequences associated with the exogenous sequence are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various polyadenylation sequences that are known in the art, widely available, and exemplified below. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In a preferred embodiment, the vector is a shuttle vector, capable of replicating in at least two unrelated expression systems. In order to facilitate such replication, the vector generally contains at least two origins of replication, one effective in each expression system. Typically, shuttle vectors are capable of replicating in a eukaryotic expression system and a prokaryotic expression system. This enables detection of protein expression in the eukaryotic host (the expression cell type) and amplification of the vector in the prokaryotic host (the amplification cell type). Preferably, one origin of replication is derived from SV40 and one is derived from pBR322 although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with the present invention.

The exogenous sequences expressed by the subject display systems can be heterolgous sequences of any length. "Heterologous" means derived from a genetically distinct entity from the rest of the entity to which it is being compared. For instance, the heterologous sequence can be a gene not normally expressed in the genetic package (e.g. bacterial cell or phage particle). Alternatively, the heterologous sequence can be a gene native to the genetic package but is linked to a coding sequence other than the native sequence that the gene is naturally operably linked to. Furthermore, the heterologous sequence may encode random or predetermined polypeptide.

The exogenous sequence expressed by the subject systems also can be characterized based on one or more of the following features: species origin, developmental origin, primary structural similarity, involvement in a particular biological process, association with or resistance to a particular disease or disease stage, tissue, sub-tissue or cell-specific expression pattern, and subcellular location of the expressed gene product.

In one aspect, the exogenous sequence may be any sequence expressed in an entity other than the genetic package, such as a plant cell, animal cell or a yeast cell.

In another aspect, the exogenous sequences are of a specific developmental origin, such as those expressed in an embryo or an adult organism, during ectoderm, mesoderm, or endoderm formation in a multi-cellular animal, or during development of leaves, tubers, bud of a plant.

In yet another aspect, the exogenous sequences belong to a family of genes, or a sub-family of genes that share primary structural similarities. Structural similarities can be discerned with the aid of computer software described above. Non-limiting examples of gene families include those encoding proteinase, proteinase inhibitors, cell surface receptors, protein kinases (e.g. tyrosine, serine/threonine or histidine kinases), trimeric G-proteins, cytokines, PH—, SH2-, SH3-, PDZ-domain containing proteins and any of those gene families published by the Institute for Genomic Research (TIGR), Incyte Pharmaceuticals, Inc., Human Genome Sciences Inc., Monsanto, and Celera.

In yet another aspect, the exogenous sequences are involved in a specific biological process, including but not limited to cell cycle regulation, cell differentiation, chemotaxsis, apoptosis, cell motility and cytoskeletal rearrangement. In still another aspect, the exogenous sequences embodied in the invention are associated with a particular disease or with a specific disease stage. Such sequences include but are not limited to those associated with autoimmune diseases, obesity, hypertension, diabetes, neuronal and/or muscular degenerative diseases, cardiac diseases, endocrine disorders, any combinations thereof.

In yet still another aspect, the exogenous sequences encompass those exhibiting restricted expression patterns. Non-limiting exemplary gene transcripts of this class include those that are not ubiquitously expressed, but rather are differentially expressed in one or more of the plant tissues including leaf, seed, tuber, stems, root, and bud; or expressed in animal body tissues including heart, liver, prostate, lung, kidney, bone marrow, blood, skin, bladder, brain, muscles, nerves, and selected tissues that are affected by various types of cancer (malignant or non-metastatic), affected by cystic fibrosis or polycystic kidney disease. Additional examples of non-ubiquitously expressed sequences are those whose protein products are localized to certain subcellular locations: extracellular matrix, nucleus, cytoplasm, cytoskeleton, plasma and/or intracellular membranous structures which include but are not limited to coated pits, Golgi apparatus, endoplasmic reticulum, endosome, lysosome, and mitochondria.

The subject display system may comprise a selectable library of genetic packages. The packages may express the same or distinct exogenous sequences. In one aspect, the library of genetic packages encodes a population of random or predetermined polypeptides. In another aspect, the library encodes a population of cDNAs that are derived from cells of specific host origin, tissue origin, developmental stage, or particular disease state.

A particularly preferred library encodes a population of antigen-binding units. The antigen-binding units may be monomeric or multimeric. Monomeric antigen-binding units are commonly referred as single-chain antigen-binding units (Sc Abus), whereas the multimeric antigen-binding units are referred to herein as non-single-chain antigen-binding units (Nsc Abus).

The Nsc Abus that can be displayed by the subject system may be either "monovalent" or "multivalent." The displayed multivalent-Abus can be further characterized as "monospecific" or "multispecific" Abus. To display multimeric Abus, two sets of expression vectors, one comprising the light chain (L) variable regions, and the other comprising the heavy chain (H) variable regions must be employed. Whereas the expressed antibody regions dimerize through preferably heterodimerization sequences fused in-frame with the antibody regions, one of the expressed antibody regions must comprise additionally, an adapter capable of pairwise interaction with the other adapter provided by the helper vector.

Nucleotide sequences corresponding to various regions of L or H chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection (http://www.atcc.org), which offers a diverse collection of well-characterized hybridoma cell lines. Alternatively, antibody nucleotides can be obtained from immunized or non-immunized rodents or humans, and form organs such as spleen and peripheral blood lymphocytes: Specific techniques applicable for extracting and synthesizing antibody nucleotides are described in Orlandi et al. (1989) *Proc. Natl. Acad. Sci. U.S.A* 86: 3833-3837; Larrick et al. (1989) *Biochem. Biophys. Res. Commun.* 160:1250-1255; Sastry et al. (1989) *Proc. Natl. Acad. Sci., U.S.A.* 86: 5728-5732; and U.S. Pat. No. 5,969,108.

The antibody nucleotide sequences may also be modified, for example, by substituting the coding sequence for human heavy and light chain constant regions in place of the homologous non-human sequences, or vice versa. In that manner, chimeric antibodies are prepared that retain the binding specificity of the original antibody.

Where desired, the exogenous sequence may comprise sequences coding for moieties that facilitate detection of the expression and purification of the protein product. Examples of such moieties are known in the art and include those encoding reporter proteins such as β-galactosidase, β-lactamase, chloramphenicol acetyltrnasferase (CAT), luciferase, green fluorescent protein (GFP) and their derivatives. Other sequences that facilitate purification may code for epitopes such as Myc, HA (derived from influenze virus hemagglutinin), His-6 (SEQ ID NO: 30), FLAG, or the Fc portion of immunoglobulin, glutathione S-transferase (GST), and maltose-binding protein (MBP).

Host Cells of the Present Invention:

The invention provides host cells comprising the expression and/or helper vectors described above. The expression vectors can be introduced into a suitable prokaryotic or eukaryotic host cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. Depending on the features of the host cells, one of ordinary skill can readily practice one or more of the appropriate means that are well established in the art.

Once introduced into a suitable host cell, expression of the exogenous sequence can be determined using any nucleic acid or protein assay known in the art. For example, the presence of transcribed mRNA of the exogenous sequence can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of the exogenous sequence.

Expression of the exogenous sequence can also be determined by examining the expressed protein product. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

The host cells of this invention can be used, inter alia, as repositories of the subject exogenous sequences, vectors, or as vehicles for producing and screening desired polypeptides such as Abus based on their binding specificities.

Uses of the Adapter-Directed Display Systems of the Present Invention:

The adapter-directed display systems of this invention have several specific uses. First, the systems permit the production of soluble monomeric and multimeric exogenous polypeptides in suitable host cells. Second, the systems allow the display of monomeric and multimeric polypeptides on selected genetic packages. The subject display systems also can be used to create libraries of random or predetermined polypeptides, full-length proteins, and protein domains for a variety of purposes. For instance, the displayed libraries can be employed for mapping epitopes and mimotopes, identifying antagonists and agonists of various target proteins, engineering antibodies, optimizing antibody specificities and creating novel binding activities.

Accordingly, the present invention provides a method of detecting the presence of a specific interaction between a test agent and an exogenous polypeptide that is displayed on a genetic package. The method involves the steps of: (a) providing a genetic package of the subject display system that presents the exogenous polypeptide; (b) contacting the genetic package with the test agent under conditions suitable to produce a stable polypeptide-agent complex; and (c) detecting the formation of the stable polypeptide-agent complex on the genetic package, thereby detecting the presence of the specific interaction.

For the purposes of this invention, a "test agent" is intended to include, but not be limited to a biological or chemical compound such as a simple or complex organic or inorganic molecule, a protein, carbohydrate, lipid, polynucleotide or combinations thereof. A vast array of compounds can be synthesized, for example oligomers, such as oligopeptides and oligonucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen. Preferred agents are candidate diagnostics and/or therapeutics, such as those capable of modulating the signal transduction pathways of a cell.

In a separate embodiment, the present invention provides a method of obtaining a polypeptide with desired property. The method comprises the steps of (a) providing a selectable library of the subject display system; and (b) screening the selectable library to obtain at least one genetic package displaying a polypeptide with the desired property. The method may further comprise the step of isolating the genetic package that displays a polypeptide having the desired property. Such isolation of the genetic package may involve obtaining a nucleotide sequence from the genetic package that encodes the desired polypeptide. The desired property encompasses the ability of the polypeptide to specifically bind to an agent of interest. The selected polypeptide with the desired property may fall within one or more classes of the following molecules, namely antigen-binding unit, cell surface receptor, receptor ligand, cytosolic protein, secreted protein, nuclear protein, and functional motif thereof. The choice of specific agent to be tested and the libraries of exogenous polypeptides to be displayed will depend on the intended purpose of the screening assay.

Isolating Antibodies Exhibiting Desired Binding Specificity or Affinity:

One of the most powerful applications of phage and bacterial display is in the arena of antibody engineering. It has been shown that scFv antigen-binding units can be expressed on the surface of both phage particles and bacterial cells with no apparent loss of binding specificity and affinity (McCafferty et al. (1990) *Nature* 348:552-554; Daugherty et al. (1999) *Protein Engineering* 12 (7): 613-621). It has also been demonstrated that functional Nsc Abus such as Fab fragments can be expressed the on phage surface. Today, antibodies to many diverse antigens have been successfully isolated using phage display technology.

The subject phage display system is particularly suited for this application because the system allows presentation of a vast diverse repertoire of Abus. In many respects the subject phage display system mimics the natural immune system. Antigen-driven stimulation of Abu can be achieved by selecting for high-affinity binders from a phage display library of Abus. The large number of chain permutations that occur during recombination of H and L chain genes in developing B cells can be mimicked by shuffling the cloned H and L chains as DNA, and protein and through the use of site-specific recombination (Geoffory et al. (1994) *Gene* 151:109-113). The somatic mutation can also be matched by the introduction of mutations in the CDR regions of phage-displayed Abus.

The Abus with desired binding specificity or affinity can be identified using a form of affinity selection known as "panning" (Parmley and Smith (1988) *Gene* 73:305-318). The library of Abus is first incubated with an antigen of interest followed by the capture of the antigen with bound phage. The phage recovered in this manner can then be amplified and again gain selected for binding to the antigen, thus enriching for those phages that bind the antigen of interest. Usually, three to four rounds of selection can be accomplished with a week, leading to the isolation of one to hundreds of binding phages. Thus rare phage expressing desired Abu can easily be selected from greater than $10^8$ different individuals in one experiment. The primary structure of the binding Abu is then deduced by nucleotide sequence of the individual phage clone. When human $V_H$ and $V_L$ regions are employed in the displayed Abus, the subject display systems allow selection of human antibodies without further manipulation of a non-human Abu.

Generating Novel Proteins Including Abus with Improved Binding Specificity or Affinity:

Using the subject display systems, one can obtain a replicable genetic package that displays a polypeptide, such as an Abu, having high affinity and specificity for a target protein. Such a package carries both amino acids of the binding polypeptide and a polynucleotide encoding the binding product. The presence of the polynucleotide facilitates recombinant expression and subsequent manipulation of the binding protein. For instance, the polynucleotide coding for the binding protein can be mutagenized by cassette mutagenesis, error-prone PCR, or shuffling to generate a refined repertoire of altered sequences that resemble the parent polynucleotide. Upon screening the refined repertoire of novel binding proteins, those exhibiting improved binding specificity or affinity can be identified.

Mapping Antigenic Epitopes:

Traditionally, epitope mapping of an antigen has relied heavily on physical chemical analysis. These approaches have included: (1) fragmenting the purified antigen with various proteases, identifying reactive fragments, and sequencing them; (2) chemical modification experiments in which residues interaction with the antigen-binding unit are protected from modification; (3) synthesizing a series of peptides corresponding to the primary structure of the antigen; and (4) direct physical characterization using NMR or X-ray crystallography. All of these methods are labor intensive and generally not amenable to high-throughput analyses. Phage or bacterial display provides a highly efficient and robust alternative for localizing the antigenic epitope. Fragments of DNA that encode portions of the antigen can be expressed as the exogenous polypeptides by the subject expression vectors. The genetic packages (e.g. phage, bacterial cells or spores) can then be tested with the antibody to determine which displayed fragments react with the antibody. This application of display technology has been widely used in the art and shown to be successful for determining the antigenic epitopes of a variety of molecules.

Mapping Binding Epitopes of Monoclonal and Polyclonal Abus

The subject display system also can be used to present random peptide libraries for mapping the specificity of the antigen-binding sites. Random peptide libraries represent a source of sequences from which epitopes and mimotopes can be operationally defined. With such a library, one can identify and obtain peptide competitors for antigen-antibody interactions, and thus map accessible and/or functional sites of numerous Abus.

Identifying Ligands of Receptors and Other Modulators of Signal Transduction Pathway:

The subject display systems can also be employed to identify ligands for receptors. The process generally proceeds with subjecting a population of genetic packages expressing the test ligands to the receptors, followed by identifying the packages bound to the receptors. Alternatively, the receptors may be presented in the genetic packages. Those that are bound to the test ligands are then isolated. For identification of peptide ligands, random peptide libraries are preferred staring materials for performing the assay. The same approach is applicable for identifying other modulators of the signal transduction pathways of a cell.

The activity of cells is regulated by external signals that stimulate or inhibit intracellular events. The process by which stimulatory or inhibitory signals are transmitted into and within a cell to elicit an intracellular response is referred to as signal transduction. Proper signal transduction is essential for proper cellular function. Over the past decades, numerous cellular signaling molecules have been identified, cloned and characterized. Non-limiting examples of the signaling proteins include cell surface receptors, protein kinases (e.g. tyrosine, serine/threonine or histidine kinases), trimeric G-proteins, cytokines, SH2-, SH3-, PH—, PDZ-, death-domain containing proteins, and any of those gene or protein families published by Human Genome Sciences Inc., Celera, the Institute for Genomic Research (TIGR), and Incyte Pharmaceuticals, Inc. Cascades of signal transduction events mediated by the ever-growing families of signaling proteins have been elucidated and found to play a central role in a variety of biological responses. Among them are cell cycle regulation, call differentiation, apoptosis, chemotaxis, cell motility and cytoskeletal rearrangement (Cantley et al. (1991) *Cell* 64:281-302); Liscovitch et al. (1994) *Cell* 77:329-334). Defects in various components of signal transduction pathways have also been found to account for a vast number of diseases, including numerous forms of cancer, vascular diseases and neuronal diseases. Indeed, agents capable of modulating signaling pathways (i.e. modulators of the signal transduction pathway) have long been acknowledged as potential diagnostic and/or therapeutic agents.

The modulators of the present invention is characterized by their ability to (1) bind to intracellular signaling proteins presented on the subject genetic packages; or (2) compete for binding to the displayed signaling proteins in the presence cellular proteins that are normally associated with the signaling proteins. The modulators can be an agonist or an antagonist of a target signal protein.

Expressing cDNA Libraries:

The subject display systems are particularly suited for expressing cDNA libraries. As noted above, the previously reported fusion systems including the gene III and gene VIII phage display systems restrict the point of insertion to the 5' end of the outer-surface sequence. The exogenous polypeptide thus must be linked to the N-terminus of the outer-surface proteins. Consequently, cDNA libraries containing fragments of coding sequences of all reading frames cannot be fully expressed by these fusion systems due to the disruption of reading frames by internal stop codons. The subject systems, however, do not suffer from this drawback of unidirectional cloning because the exogenous sequence is not fused in frame with the outer-surface sequence.

cDNA display can be a useful technique for defining protein-protein interactions. Expression and screening of cDNA libraries greatly facilitate the identification of novel genes based on the ability of the expressed product to bind a known protein of particular interest. The cDNA-encoded proteins can be expressed on the surface of the subject genetic packages, which can then be tested against a particular immobilized target in vitro via biopanning enrichment as detailed above.

The ability of a displayed exogenous polypeptide or a library of random or predetermined polypeptide to specifically bind to a test agent can be tested by a variety of procedures well established in the art. Generally selection is preferably performed using affinity chromatography. The method typically proceeds with binding the genetic packages a test-agent-coated plates, column matrices, cells or to biotinylated agents in solution followed by capture. The genetic packages bound to the solid phase are washed and then eluted by soluble hapten, acid or alkali. Alternatively, increasing concentrations of the test agent can be used to dissociate the genetic packages from the affinity matrix. For certain Abus with extremely high affinity or avidity to the test antigen, efficient elution may require high pH or mild reducing solution as described in WO 92/01047.

To avoid potential difficulties in recovering the bound polypeptide with the desired binding specificities, protease cleavage sites may be introduced between the adapter and exogenous polypeptide. Cleavage sites applicable for this purpose include but are not limited to Factor X, trypsin, and thrombin recognition sites. After binding the genetic packages to an affinity matrix and washing the non-specific packages, the remaining packages that display the exogenous polypeptide with the desired affinity can be collected by washing the antigen-affinity matrix with protease under conditions suitable for digestion at the cleavage site. Such digestion would release the exogenous polypeptide from the genetic packages such as phage particles.

An alternative procedure to the above is to take the affinity matrix which has retained the strongly bound phage or bacterial particles and extract their nucleic acids, for example by boiling in SDS solution. Extracted nucleic acids can be used to directly transform *E. coli* host cells or alternatively the exogenous sequence can be amplified by PCR using suitable primers.

The efficiency of selection is likely to depend on a combination of several factors, including the kinetics of dissociation during washing, and whether multiple copies of the exogenous polypeptides on a single phage or bacterium can simultaneously bind to the test agent on a solid support. For example, antibodies with fast dissociation kinetics (and weak binding affinities) should be retained by use of short washes, multivalent display and a high coating density of antigen at the solid support. Conversely, the selection of Abus with slow dissociation kinetics (and good binding affinities) should be favored by use of long washes, monovalent phages, and a low coating density of antigen.

Alternatively, specific binding to a given agent can be assessed by cell sorting. The technique involves presenting the exogenous polypeptide on genetic packages such as phage particles that are adhered to host cells to be sorted, then labeling the target cells with test agents that are coupled to detectable moieties, followed by separating the labeled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescent label is then measured.

Where desired, the repertoire of exogenous polypeptides can be pre-selected against an unrelated test agent to counter-select the undesired polypeptide. For instance, a repertoire of Abus may be counter-selected against a unrelated antigen. The repertoire may also be pre-selected against a related agent in order to isolate, for example, anti-idiotypic Abus. The subject display systems enables rapid isolation of Abus with desired specificities. Many of the isolated Abus would be expected to be difficult or impossible to obtain through conventional hybridoma or transgenic animal technology.

Subsequent analysis of the eluted Abus may involve protein sequencing for delineating the amino acid sequences of the L and H chains. Based on the deduced amino acid sequences, the cDNA encoding the antibody polypeptides can then be obtained by recombinant cloning methods including PCR, library screening, homology searches in existing nucleic acid databases, or any combination thereof. Commonly employed databases include but are not limited to GenBank, EMBL, DDBJ, PDB, SWISS-PROT, EST, STS, GSS, and HTGS.

Kits Comprising the Vectors of the Present Invention

The present invention also encompasses kits containing the expression and helper vectors of this invention in suitable packaging.

Each kit necessarily comprises the reagents which render the delivery of vectors into a host cell possible. The selection of reagents that facilitate delivery of the vectors may vary depending on the particular transfection or infection method used. The kits may also contain reagents useful for generating labeled polynucleotide probes or proteinaceous probes for detection of exogenous sequences and the protein product. Each reagent can be supplied in a solid form or dissolved/ suspended in a liquid buffer suitable for inventory storage, and later for exchange or addition into the reaction medium when the experiment is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

Further illustration of the development and use of subject display systems, host cells, and genetic packages are provided in the Example section below. The examples are provided as a guide to a practitioner of ordinary skill in the art, and are not meant to be limiting in any way.

EXAMPLES

Example 1

Preparation and Uses of KO7kpn Helper Phage

Figure 3A:
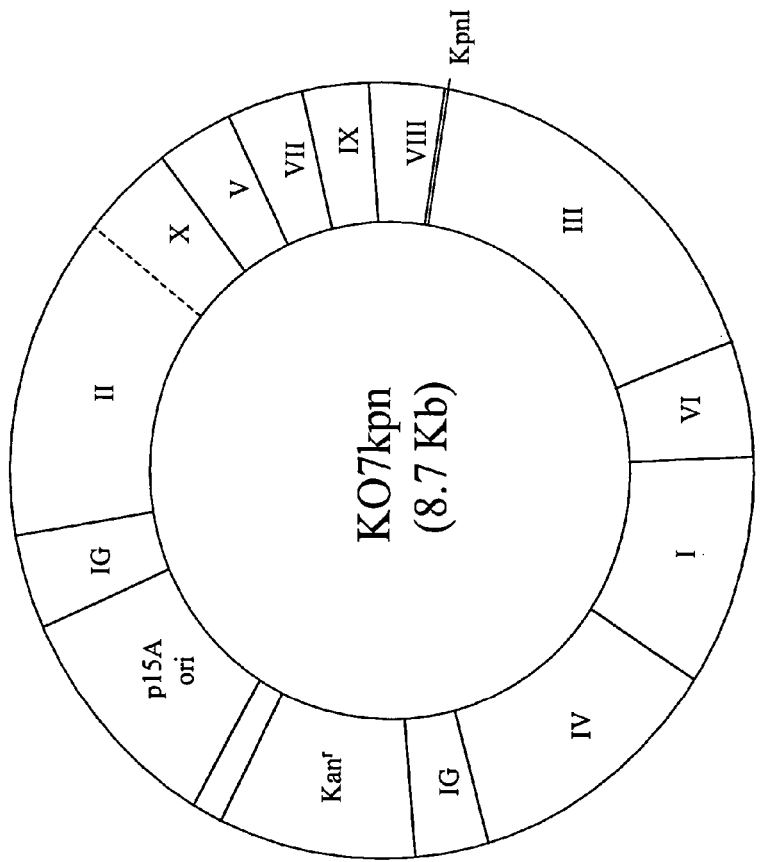
FIG. 3A is a schematic representation of the KO7kpn helper phage vector.

A. Construction of KO7kpn Vector:

The KO7kpn vector was constructed by modifying a well-characterized vector, namely M13KO7 (from Amersham Pharmacia) according to the procedure detailed below. The resulting vector is identical to KO7 except that a unique KpnI restriction site has been inserted into the gene III leader sequence without disrupting the gene III coding region (see FIGS. 3A and 3B).

The KpnI site was introduced into the gene III leader sequence of KO7 helper phage vector by PCR-based site-directed mutagenesis. The KO7 genome was amplified by PCR using the following primers which contain KpnI sites: p3KN1: 5'-TTTAGTGGTA CCTTTCTATTCTCACTC-CGCTG-3' (SEQ ID NO: 26) and p3KN2: 5'-TAGAAAGG-TACCACTAAAG GAATTGCGAATAA-3' (SEQ ID NO: 27). These primers share partial sequence homology to gene III leader sequence.

Figure 1:
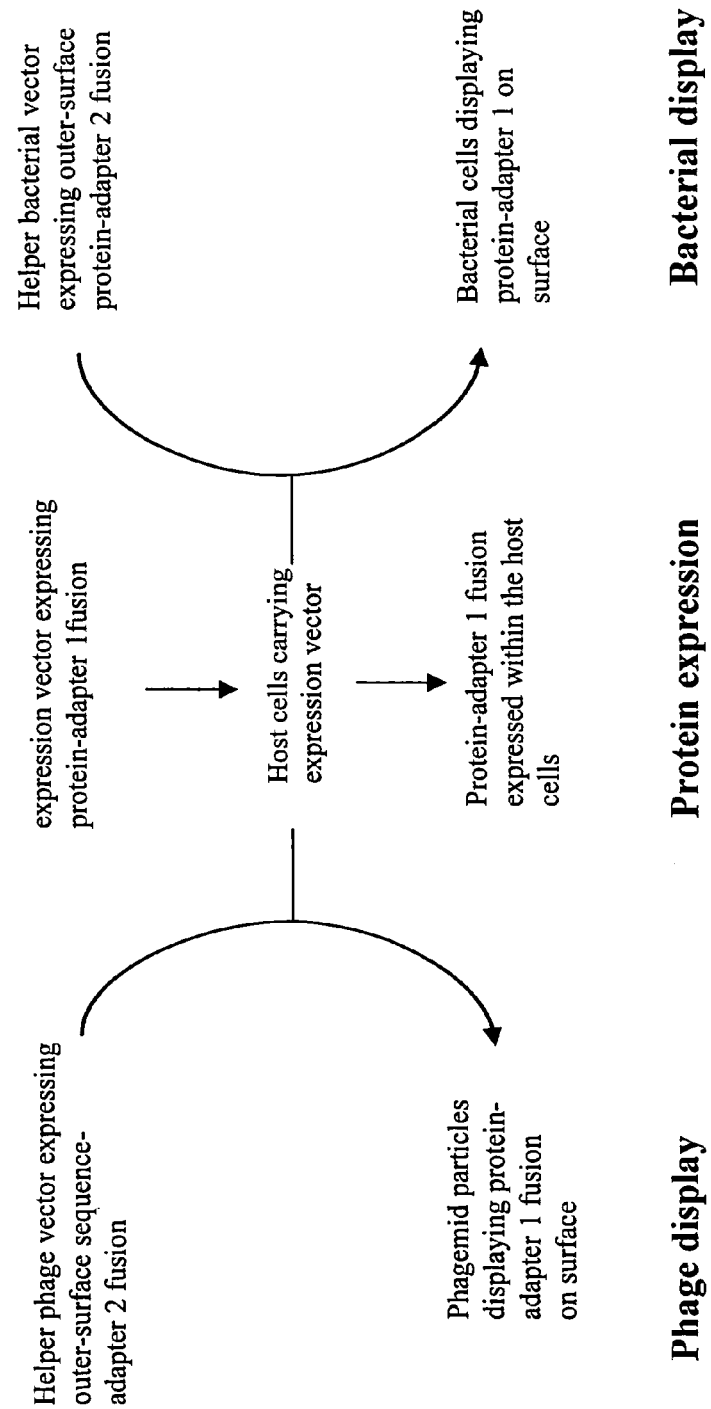
FIG. 1 is a schematic representation of the experimental design of the subject adapter-directed display systems. The depicted display systems not only permit expression of soluble exogenous polypeptides in a suitable host cell, but also allow display of the exogenous sequence on the outer surface of a genetic package. The system has two components: an expression vector and a helper vector. Introduction of the expression vector alone into a host cell such as E. Coli bacterium leads to expression and secretion into the bacterial periplasm of the exogenous polypeptide which is fused in-frame with an adapter (designated "adapter 1, " see center panel of FIG. 1). Superinfection of the bacterial cells with a helper phage vector that carries a phage outer-surface sequence fused in-frame with a second adapter (designated "adapter 2, " see left panel) permits display of the exogenous polypeptide on the phage particles via pairwise interaction between the first and second adapters. A diverse DNA sequences can be inserted into this expression vector to construct an expression library. Superinfection of the helper phages yields a diverse phage display libraries. Similarly, infection of the bacterial cells with the phagemid particles packaging a helper bacterial vector that carries a bacterial outer-surface sequence fused in-frame with a second adapter (designated "adapter 2, " see right panel), permits display of the exogenous polypeptide on bacteria via pairwise interaction between the first and second adapters. A selectable bacterial display library can be constructed in a similar manner.
Figure 2:
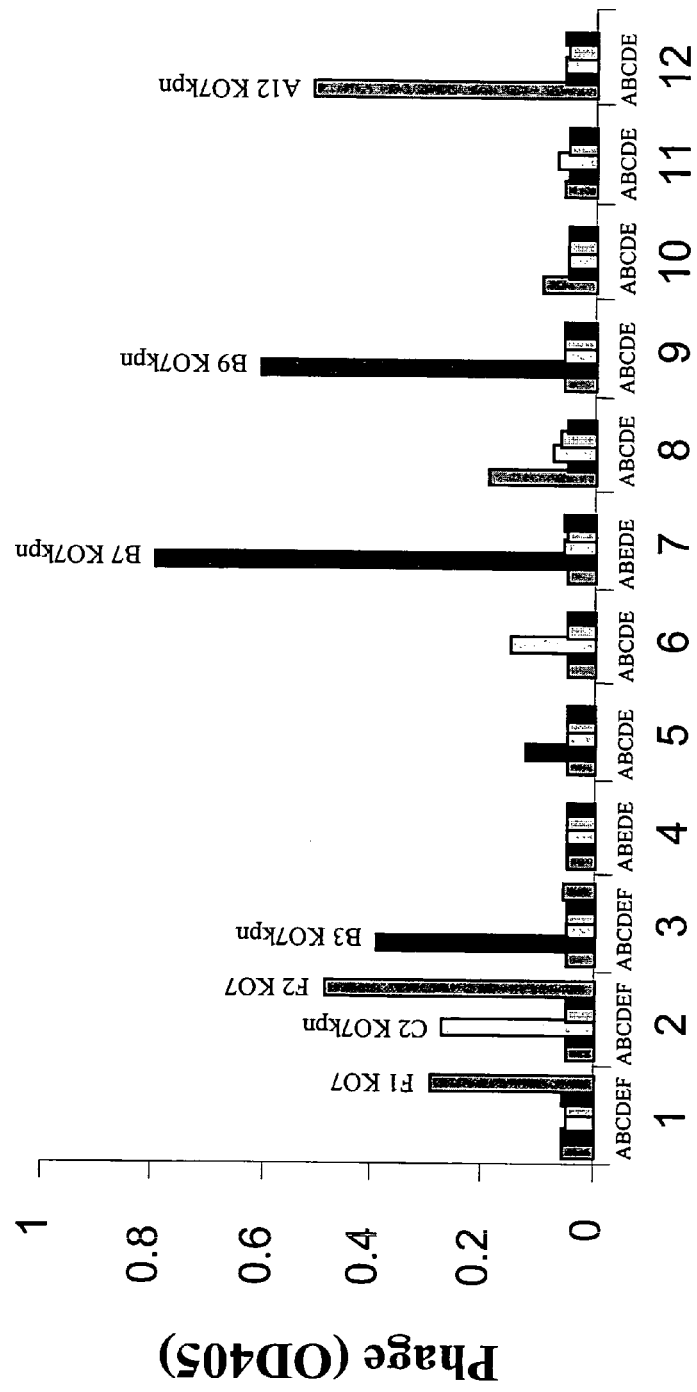
FIG. 2 shows the results of a phage ELISA screen for kanamycin-resistant, KO7kpn helper phage-positive clones. 48 clones were screened for phage generation. C2, B3, B7, B9, A12 represent KO7kpn helper phage-positive clones. F1 and F2 represent two positive controls of parent M13KO7 phages.

PCR was performed in a 100 ul reaction mixture containing 100 ng KO7 vector DNA, 20 pmol each of primers, 250 uM dNTP, and 1× pfu buffer and pfu DNA polymerase (Stratagene). The reaction mixture was initially incubated at about 96° C. and then subjected to 15 cycles of PCR in a thermocycler as follows:

denaturation 96° C., 30 seconds
annealing 55° C., 30 seconds
extension 72° C., 10 minutes After amplification, the products were gel purified, cut with KpnI and ligated to transform TG1 bacterial cells by electroporation. The bacterial cells were sleeted for kanamycin resistance. Specifically, the kanamycin-resistant ($Kan^R$) colonies were grown in 96-well microtiter plates in 2× YT medium with 70 ug/ml Kanamycin, and supernatants were used for phage screening by phage ELISA assay to eliminate the loss-of-function mutants caused by PCR errors. Briefly, the phage ELISA was conducted as follows: A 100 ul of the supernatant containing phage particles was employed to coat wells of the ELISA plates at 4° C. overnight. After blocking with 5% milk in PBS buffer for 30 minutes at room temperature, the phage particles bound on ELISA plates were further incubated with 100 ul of HRP-conjugated anti-M13 antibody (Amersham Pharmcia) for 1 hour at room temperature. The free anti-M13 antibodies were washed away by PBS containing 0.05% Tween 20. The substrate ABTS [2,2'Azino-bis(3-ethylbenzthiazoline-6-sulfonic acid)] was then added. The HRP activity was determined by the absorbance at 405 nm. FIG. 2 shows the results of a phage ELISA screen for kanamycin-resistant, phage-positive clones. 48 clones were screened for phage generation. The clones C2, B3, B7, B9, A12 were phage positive. The DNAs extracted from clones B7, B9 and A12 were prepared from TG1 cultures. Double digestion of vector DNA with Acc65I (isoschizomer of KpnI) and BamHI showed a 600 bp DNA fragment, which confirms the presence of KpnI site in all of the three KO7kpn vector clones.

B. KO7kpn Phage Generation:

The $Kan^R$TG1 supernatant containing KO7kpn helper phages produced from B9 clone was streaked on a 2×YT agar plate. 4 ml of soft agar mixed with 0.5 ml of TG1 culture (OD600=0.5) was poured on the plate. Phage plaques were formed after incubation at 37° C. overnight. A single phage plaque was picked and used to inoculate 10 ml 2×YT culture with 70 µg/ml kanamycin. After incubating at 37° C. for 2 hours with constant shaking at 250 rpm, the culture was transferred to a 2 liter flask containing 500 ml 2×YT with 70 µg/ml kanamycin. The culture was incubated overnight with constant shaking. The phages in the supernatants were then precipitated using polyethylene glycol (PEG)/NaCl, and re-suspended in phosphate-buffed saline (PBS). The phage concentration was determined by $OD_{268}$ measurement. Generally, a reading of 1 unit at $OD_{268}$ indicates that the supernatant contains approximately $5\times10^{12}$ phage/ml. The recorded phage yield for KO7kpn helper phage was approximately $1-2\times10^{12}$/ml, which was very similar to that of the M13KO7 helper phages.

C. Use of KO7Kpn Helper Phage for Phage Display:

The coding sequence of scFv antibody AM2 was subcloned into phage display vector pABMD1 (FIG. 22) that expresses scFv-pIII fusions. TG1 cells carrying the display vectors were grown to OD600=0.6, and superinfected by KO7kpn helper phage at MOI=10. The infected TG1 cells were grown in 2× YT/Amp/Kan at 30° C. overnight. The phagemid particles were precipitated twice by PEG/NaCl from culture supernatants, and resuspended in PBS. The scFv-pIII fusions displayed on phage were detected via phage ELISA assay. Briefly, 0.2 ug AM2-antigens were first coated onto 96-well ELISA plates at 4° C. overnight. After 5% milk/PBS blocking, the phage solution in 2% Milk/PBS was placed onto the ELISA plates for 1 hour. The phage bound to antigen was detected by incubation with HRP-conjugated anti-M13 antibody. The substrate ABTS [2,2'Azino-bis(3-ethylbenzthiazoline-6-sulfonic acid)] was used for measurement of HRP activity. The phagemids generated from the TG1 cells carrying pABMD1-AM2/KO7kpn vectors showed a very strong antigen binding activity, indicating the functional display of scFv antibody AM2 by KO7kpn helper phage. This series of experiments serve as positive controls for reagents employed for constructing and using the subject display systems.

Example 2

Figure 4:
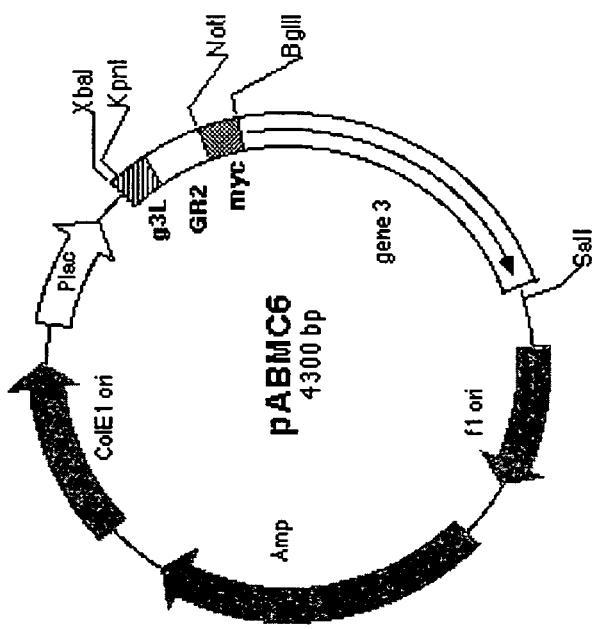
FIG. 4 is a schematic representation of vector pABMC6. The vector contains KpnI site, a partial gene III leader sequence, GR2 coding sequence and a Myc-tag placed to the 5' of gene III sequence.

Preparation of an Adapter-Directed Display System Comprising GM-UltraHelper Phage Vectors A. Construction of GM-UltraHelper Phage Vector:

The pABMC6 vector was constructed by replacing the sequence between the XbaI and BglII sites of vector pABMD1 (FIG. 22A) with a synthetic DNA fragment encoding a partial gene III leader sequence with a KpnI site, and coding sequences for GR2 domain (the coiled-coil domain of the human $GABA_B$ receptor 2) and Myc-tag (FIG. 4). The sequence for GR2-Myc domain was directly fused with the pIII coding sequence in pABMD1 vector, and was confirmed by DNA sequencing.

The GM-UltraHelper phage vector was constructed by replacing the KpnI/BamHI fragment encoding a partial pIII leader (amino acid residues 11-19) and partial pIII protein (amino acid residues 1-197) in the KO7Kpn helper vector with the corresponding fragment encoding a partial pIII leader and the adaptor2-pIII fusion protein from the pABMC6 vector. The resulting GM-UltraHelper phage vector (FIG. 5) comprises an engineered gene III fusion in which a GR2 domain and a Myc-tag sequence (for detection of engineered pIII protein) are fused in-frame with gene III (FIG. 5B).

The B9 KO7kpn helper phage clone (see Example 1) was used for constructing the GM-UltraHelper phage vector. After subcloning of the engineered gene III fragment into KO7kpn phage vector, 20 kanamycin-resistant colonies were grown in 96-well microtiter plates in 2×YT medium with 70 ug/ml Kanamycin. The supernatant was used for phage screening by phage ELISA assay as described in Example 1. 19 clones were able to generate phage particles.

Figure 6:
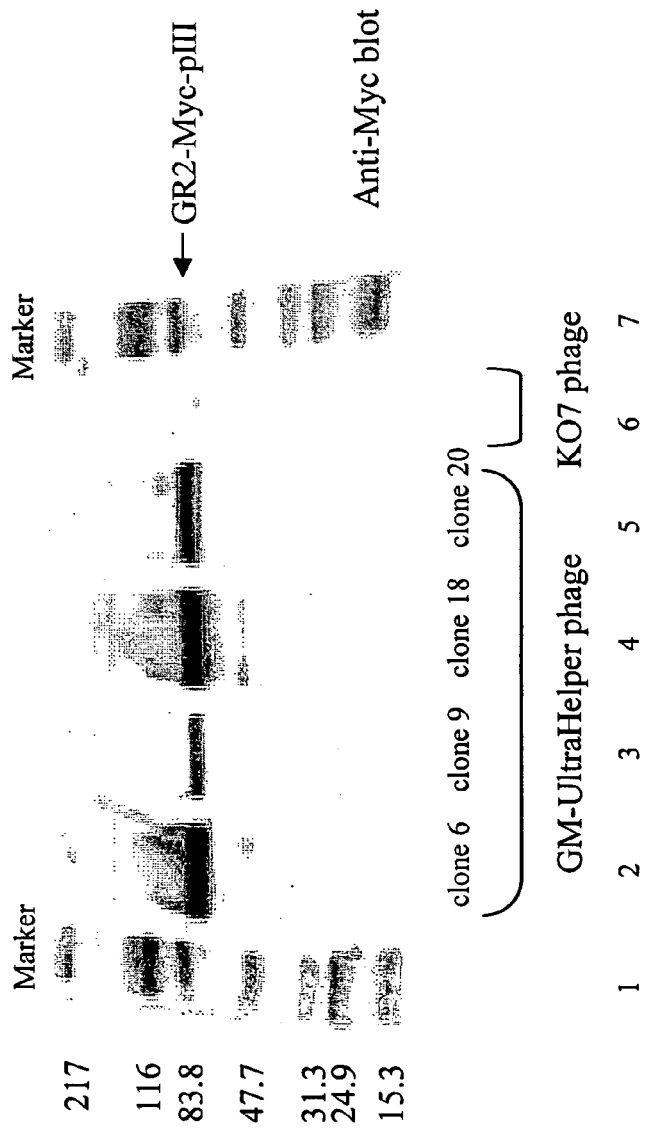
FIG. 6 is a reproduction of an anti-Myc immunoblot of phage coat proteins. The results indicate the assembly of GM-UltraHelper phage particles. Lanes 1 and 7 represent molecular weight markers in kDa. Lanes 2-5 show four clones of GM-UltraHelper phages that express the GR2-Myc-pIII fusion. Lane 6 shows a negative control of M13KO7 helper phage that does not carry the GR2-Myc-pIII fusion sequence.
Figure 7:
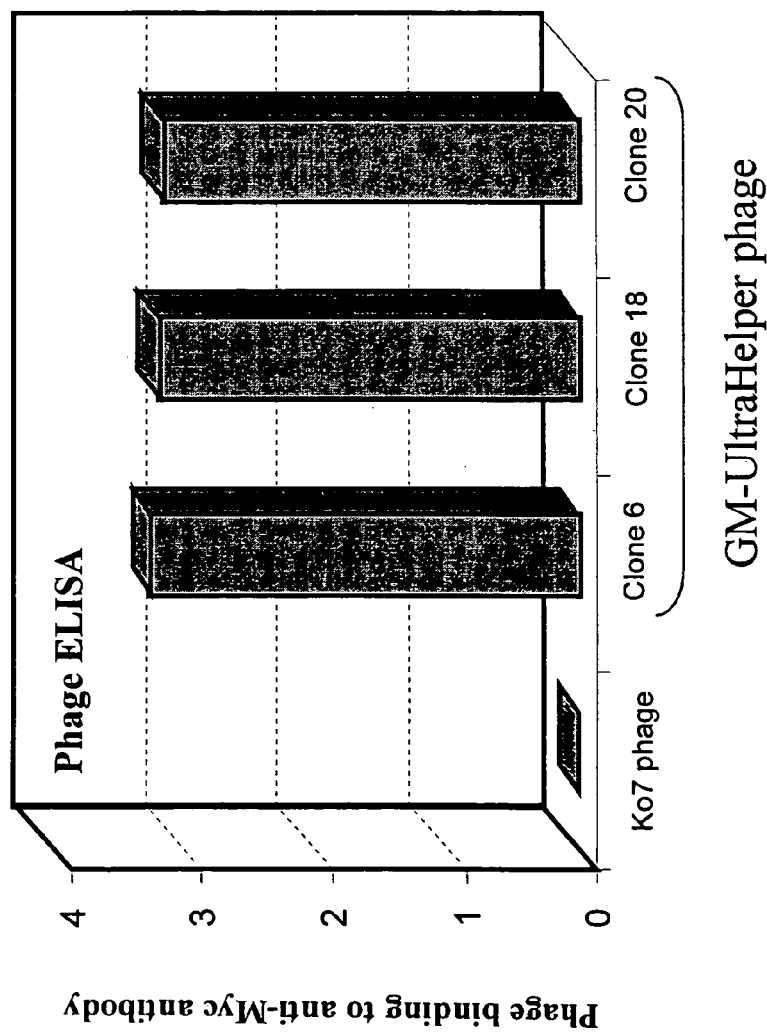
FIG. 7 depicts the results of an ELISA assay using anti-Myc antibody to detect GR2-Myc-pIII fusion proteins that are assembled into the GM-UltraHelper phage particles. Phage clones 6, 18, and 20 shown in FIG. 6 were tested. KO7 helper phage was included as a negative control.

To confirm that GM-UltraHelper phages were packaged with GR2-Myc-pIII fusion proteins, western blot using anti-Myc antibody (9E10 from BD Pharmingen) was carried out to detect the engineered pIII fusion. Briefly, $1-4 \times 10^{11}$ Phage particles from four clones (clones 6, 9, 18, and 20) were heated for 10 min in SDS sample buffer (2% SDS, 5% β-mercaptoethnol, 10% glycerol, 0.67 M Trice-HCl, pH 6.8). The denature sample was subjected to SDS-PAGE. The proteins in the SDS gel was then transferred to PVDF membrane which was subsequently probed with 2 ug/ml 9E10 antibody in 5% milk/PBS. Myc-tagged proteins were detected by anti-mouse antibody-AP conjugate and BCIP/NBT AP substrate (Sigma). As shown in FIG. 6, a single protein band was detected in all four clones by the anti-Myc antibody. No Myc-containing band was detected in the negative control M13KO7 helper phage. This experiment demonstrates that GR2-Myc-pIII fusion proteins were assembled into Ultra-Helper phage particles. The assembly of GR2-Myc-pIII fusions was further confirmed by ELISA assays (see FIG. 7).

Figure 8:
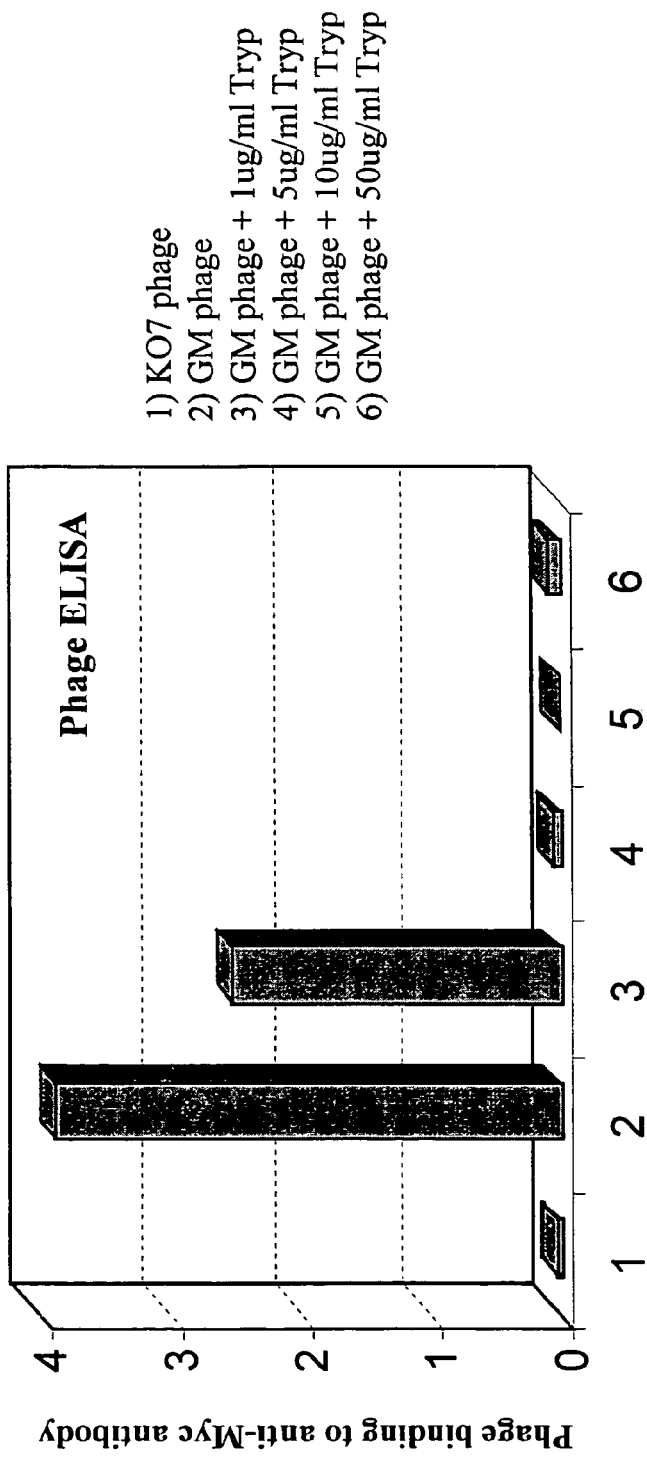
FIG. 8 depicts the results of an ELISA assay using anti-Myc antibody to demonstrate successful cleavage of GR2-Myc domain from UltraHelper phages using increasing amount of trypsin. M13KO7 helper phage served as a negative control.

It has been well known that M13 phage is resistant to trypsin. The screening for protease cleavage sites revealed that there are seven trypsin cleavage sites in the GR2-Myc domain of the GM-UltraHelper phage (FIG. 5C). To test whether the GR2-Myc domain can be cleaved from the phage surface by trypsin, GM-Ultrahelper phages from clone 18 were exposed to different concentrations of trypsin for 30 minutes at 37° C., and then trypsin inhibitor was added to stop the reaction. FIG. 8 shows that the Myc-tag could be completely removed by 5 μg/ml trypsin. The M13KO7 helper phage served as a negative control.

B. Generation of GM-UltraHelper Phages:

Phage plaque assay was carried out using the supernatant containing GM-UltraHelper phage particles described above. A single phage plaque was picked and used to inoculate 10 ml 2×YT culture with 70 μg/ml kanamycin. After 2 hours incubation at 37° C. with constant shaking at 250 rpm, the culture transferred to a 2 liter flask containing 500 ml 2×YT with 70 μg/ml kanamycin for large scale production of phage particles. The phages in the supernatants were then precipitated using polyethylene glycol (PEG)/NaCl, and re-suspended in phosphate-buffed saline (PBS). The phage concentration was determined by measuring $OD_{268}$. The OD $OD_{268}$ measurement indicates that the culture contains approximately $2 \times 10^{11}$/ml GM-UltraHelper helper phage particles. Removing of GR2-Myc domains from the surface of phage by trypsin could increase the phage infectivity by 1 to 3 folds.

C. Use of GM-UltraHelper Phage for Displaying Antigen-Binding Units:

In the subject adapter-directed display system, the exogenous polypeptide of interest is expressed as a fusion with an adapter (designated adapter 1) which interacts with a paring adapter (designated "adaptor2") that is fused in-frame with an outer-surface protein. The pairwise interaction between the two adapters facilitates display of the exogenous polypeptide. The phagemid vector pABMX14 is one of the expression vectors expressing an exogenous polypeptide fused in-frame with adapter 1. The vector pABMX14 (FIGS. 9A and 9B) was derived from pBluescript SK(+). A unique AgeI restriction site was introduced immediately after the lac promoter by PCR-based site-directed mutagenesis with a set of primers (pBS-Ska: 5'-GGAATTGTGAGCGGATAACAATTTAC-CGGTCACACAGGAAACAGCTATGA-CCATG-3' (SEQ ID NO: 28) and pBS-SKb: 5'-CATGGTCATAGCTGTTTC-CTGTGTGACCGGTAAATT-GTTATCCGCTCACAATT-CC-3' (SEQ ID NO: 29)), and the XhoI and KpnI sites were deleted by cutting and blunt-end ligation. The synthetic DNA fragment flanked by AgeI at 5' and SalI sites at 3', containing ribosome-binding sequence RBS, pelB leader, and coding sequences for the adapter derived from $GABA_B$ receptor 1 (GR1, as adaptor 1) and HA-(His)$_6$-tag (6xHis disclosed as SEQ ID NO: 30) (referred to as DH-tag), was cloned into the engineered pBluescript SK(+). The lac Z promoter drives the expression of GR1 fusion and thus permits production of soluble exogenous polypeptide expressed with a bacterial cell.

Figure 10:
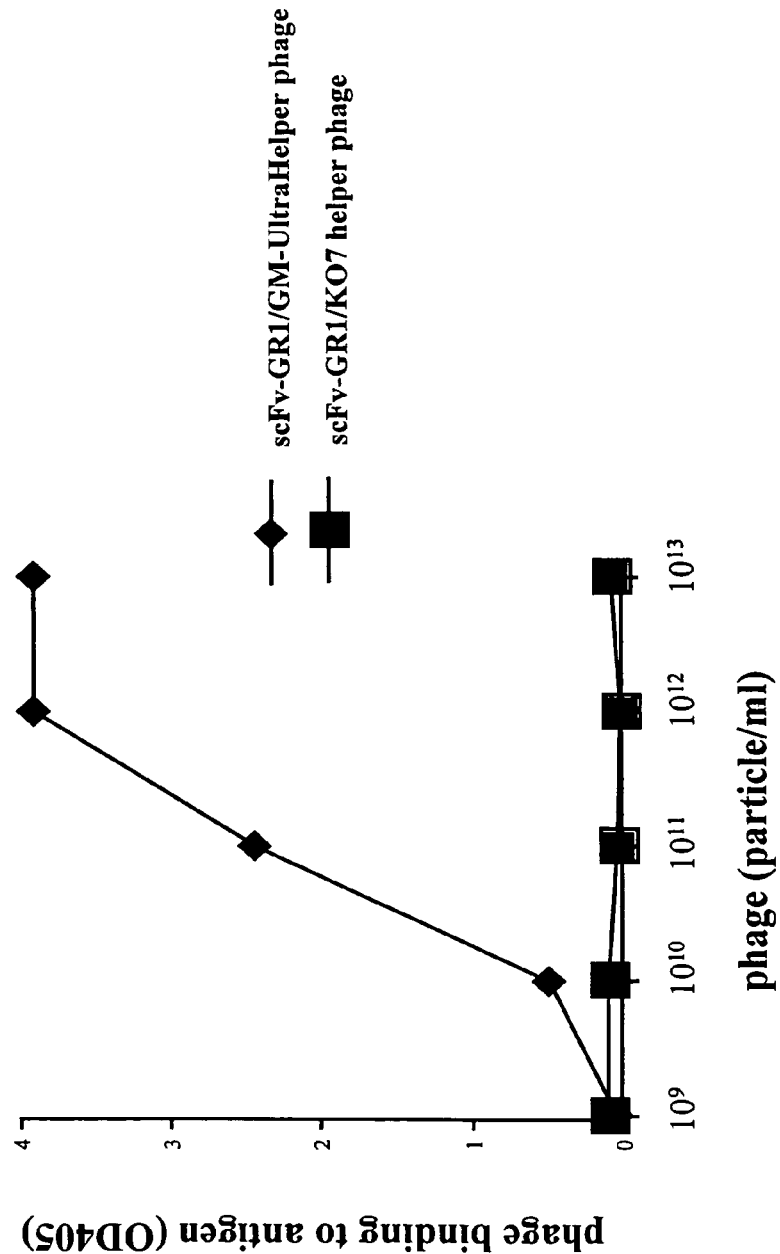
FIG. 10 depicts the results of a phage binding assay, in which the phage particles were generated upon superinfection bacterial TG1 cells with either GM-UltraHelper phage or M13KO7 helper phage. The bacterial TG1 cells harbor the pABMX14-AM1 phagemid vector for expression of scFv-adapter 1 fusion. A dose-dependent phage binding to the respective antigen was observed only upon the infection of GM-UltraHelper phage and not by the negative control M13KO7 phage. The results demonstrate the display of functional scFv on phage particles using pABMX14 phagemid and the GM-UltraHelper phage vector.
Figure 11:
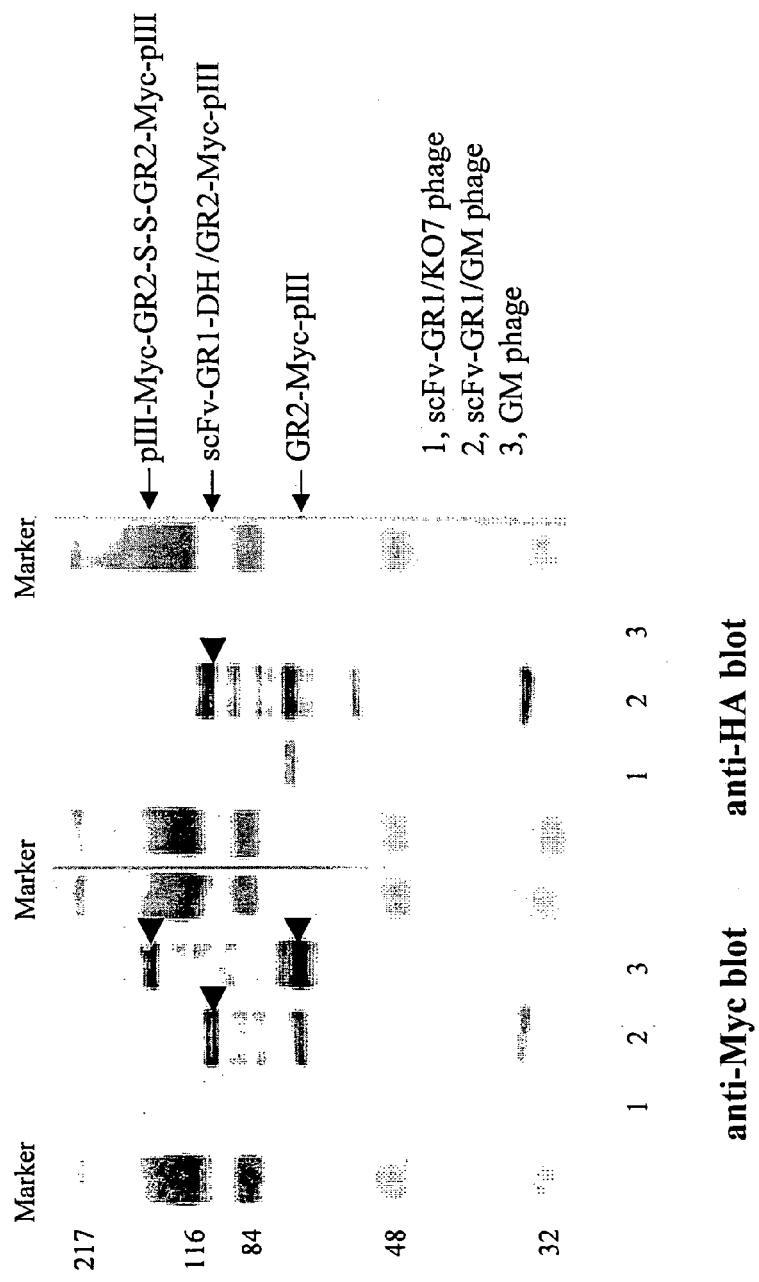
FIG. 11, left panel, is a reproduction of an anti-Myc immunoblot of phage coat proteins. Lane 1 represents a negative control in which the phage particles were generated in TG1 cells harboring phagemid vector pABMX14-AM1 superinfected by M13KO7 helper phage. Lane 2 represents phage particles generated by phagemid pABMX14-AM1 vector and GM-UltraHelper phage vector. The exogenous sequence scFv was detected. Lane 3 represents a negative control in which GM-UltraHelper phage was employed alone. Anti-Myc antibody detects, only in lane 2, a band corresponding to the scFv-GR1-DH/GR2-Myc-pIII complex formed via the pairwise interaction of GR1 and GR2. Approximately twice as much scFv-GR1-DH/GR2-Myc-pIII complex was displayed when compared to the free GR2-Myc-pIII in line 2. This indicates that each phage particle on average carries more than one copy of the scFv-GR1 fusion. A band corresponding to a dimeric pIII-Myc-GR2 was detected in lane 3. The formation of pIII-Myc-GR2 dimer was due to the pair of cysteine residues introduced downstream of the $GABA_B$ receptor 2 adapter sequence. The adapter sequence of $GABA_B$ receptor 2 per se lacks the propensity to form homodimers under physiological body temperature and/or physiological buffer conditions (Kammerer et al. (1999) *Biochemistry* 38: 13263-13269).

To demonstrate that a functional protein can be displayed using the present invention, the single-chain antibody AM1 was subcloned into the pABMX14 vector. The resulting pABMX14-AM1 vector was transformed into TG1 cells, and the cells were superinfected with GM-UltraHelper phages with a multiplicity of infection (MOI) of 4 or 40 or 100. The phage particles were generated and purified as described in Example 1. The single chain antibody displayed on the phage surface was detected by phage ELISA using plates coated with AM 1-antigen. The secondary antibody was HRP-conjugated anti-M13 antibody. The ELISA results showed that the phage particles generated from all three MOI infections exhibit binding specificity to the corresponding AM1-antigen, indicating that the single-chain antibody was functionally displayed on the phage surface (FIG. 10). A dose-dependent binding was observed. Binding was saturated when the phage concentration reached $10^{12}$/ml. The control phagemids generated from TG1 carrying pABMX14-AM1/M13KO7 vectors did not bind to AM-1 antigen even at high concentrations such as $10^{13}$/ml. The phage particles were also analyzed by Western blotting using anti-Myc and anti-HA antibodies. Phage particles were denatured by heating in SDS sample buffer under non-reducing condition (e.g. without β-mercaptoethanol). FIG. 11 shows that the scFv antibody was only displayed upon infection with GM-UltrHelper phages and not with the control M13KO7 helper phages. The anti-Myc blot also revealed that approximately twice as much scFv-GR1-DH/GR2-Myc-pIII complex over the free GR2-Myc-pIII was assembled in phage particles in line 2. Since each phage particle contains 5 copies of pIII coat proteins. This indicates that each phage particles on average carry more than one copy of the scFv-GR1 fusion.

Example 3

Preparation of an Adapter-Directed Display System Comprising CM-UltraHelper Phage Vector A. Construction of CM-UltraHelper Phage Vector:

The pABMC 13 vector was constructed by replacing the sequence between the XbaI and BglII sites of vector pABMD 1 (FIG. 22) with a synthetic DNA fragment comprising 5' to 3' a gene III leader sequence, a KpnI site, a coding sequence for Ala-Cys-Gly-Gly (SEQ ID NO: 24) and a Myc-tag (FIG. 12). This synthetic sequence was linked in-frame with gene III in pABMD1 vector.

The CM-UltraHelper phage vector was constructed by replacing the KpnI/BamHI fragment encoding (amino acid residues 11-19) and partial p III protein (amino acid residues 1-197) in the KO7Kpn helper vector with the corresponding fragment encoding a partial p III leader and the adaptor2-pIII fusion protein from the pABMC13 vector. The resulting CM-UltraHelper phage vector (FIG. 13A) encodes an engineered pIII capsid fused with Cys-myc domain placed at the N-terminal of pIII. (FIG. 13B). In addition, an amber stop codon TAG is placed between Cys-Myc coding sequence and gene III: Such a stop codon permits propagation of the entire phage particle in suppressor bacterial strains but not in non-suppressor strains.

The B9 KO7kpn helper phage clone was used for the construction of CM-UltraHelper phage vector. After subcloning of the engineered gene III fragment into KO7kpn phage vector, 24 kanamycin-resistant colonies were grown in 96-well microtiter plates in 2×YT medium with 70 ug/ml Kanamycin, and supernatants were used for phage screening by phage ELISA assay as described in Example 1. 23 clones were found to generate phage particles.

To confirm that CM-UltraHelper phages are able to package the expressed Cys-Myc-pIII fusions into the phage particles, ELISA assay using anti-Myc antibody was performed. The CM-UltraHelper phages from the selected five clones all displayed the Myc-tag on their surfaces. Such Myc-tag was not detectable in the KO7 helper phage negative control (FIG. 14).

B. Generation of CM-UltraHelper Phages:

Phage plaques formation assay was carried out using the supernatant containing CM-UltraHelper phage particle according to the procedures described above. Briefly, a single phage plaque was picked and used to inoculate 10 ml 2×YT culture with 70 μg/ml kanamycin. After 2 hours incubation at 37° C. with constant shaking at 250 rpm, the culture was added to a 2 liter flask containing 500 ml 2×YT with 70 μg/ml kanamycin for incubation overnight. The phages in the TG1 supernatants were precipitated using polyethylene glycol (PEG)/NaCl, and re-suspended in phosphate-buffed saline (PBS). The phage concentration was determined by measuring $OD_{268}$. The phage yield for CM-UltraHelper helper phage is approximately $1-2\times10^{12}$/ml culture, which is very similar with that of M13KO7 and KO7kpn helper phage. The Myc-tag can be removed from the surface of phage by trypsin. Because of the amber stop codon placed in engineered gene III, no significant amount of CM-UltraHelper phage particles can be generated in a non-suppressor bacterial strain TOP10F'.

C. Use of CM-UltraHelper Phage for Displaying Antigen-Binding Units:

The phagemid vector pABMX15 is another illustrative expression vector that expresses an exogenous polypeptide (a single-chain antibody AM1) fused in-frame with an adapter. The vector pABMX15 (FIGS. 15A and 15B) was constructed from pABMD2 (FIG. 22) by replacing the fd gene III fragment of pABMD2 (using NotI and SalI sites) with a synthetic DNA fragment encoding the HA-Tag and Gly-Gly-Cys.

To demonstrate that a functional protein can be displayed using CM-UltraHelper phage vector, the single-chain antibody AM1 was subcloned into the pABMX15 vector. The resulting PABMX15-AM1 was transformed into TG1 cells, and the cells were superinfected with CM-UltraHelper phage with a multiplicity of infection (MOI) of 1 or 10 or 50 or 100. Phage particles were generated and purified as described in Example 1. The single-chain antibody displayed on the phage surface was detected by phage ELISA using plates coated with AM1-antigen. $2\times10^{12}$ phages were added for each well. The secondary antibody was HRP-conjugated anti-M13 antibody. The ELISA results showed that the phagemid particles generated from all four MOI infections were capable of specifically binding to AM1-antigen, indicating that functional single-chain antibody was displayed on the phage surface (FIG. 16). The control phagemids generated from TG1 carrying pABMX15-AM1/M13KO7 vectors did not bind to AM1-antigen. The phage particles were also used for western blot analysis. Phage particles were denatured by heating in SDS sample buffer under non-reducing condition (e.g. without β-mercaptoethanol). As shown in FIG. 17, the scFv antibody was only displayed by CM-UltrHelper phage, but not M13KO7 helper phage.

FIG. 17 also indicates that more free pIII is displayed on the phage particles than the AM1 scFv (see lane 4 of the left panel). This is indicative of monovalent display. By contrast, the GM-UltraHelper phage display system described in Example 2 yields more AM1 scFv than the free pIII (see lane 2 of FIG. 11, left panel). The inclusion of the adapter sequence of $GABA_B$ receptor 1 in the scFv sequence, and the incorporation of the adapter sequence $GABA_B$ receptor 2 in GM-UltraHelper vector enhance the pairwise interaction.

Example 4

Preparation of an Adapter-Directed Display System Comprising GMCT-UltraHelper Phage Vector A. Construction of GMCT-UltraHelper Phage Vector:

The pABMC12 vector was constructed from vector pABMC6, in which the NotI-BglII fragment was replaced with a synthetic DNA fragment containing coding sequence for Myc-tage, CT domain (amino acids 217-405) of gene III, a ribosome binding site (RBS) and an OmpA leader sequence (FIGS. 22A and B).

The GMCT-UltraHelper phage vector was constructed by replacing the KpnI/BamHI fragment in the KO7kpn helper vector with the corresponding fragment from pABMC12 vector. The resulting GMCT-UltraHelper phage vector (FIG. 19A) encodes an additional copy of engineered pIII capsid, which comprises a GR2 domain, a myc-tag sequence (for detection of engineered pIII protein) and CT domain of pIII. Downstream to the engineered gene III, a ribosome binding sequence (RBS) and a leader sequence from the bacterial protein OmpA were fused to gene III sequences derived from pAMBD1. Those two copies of gene III-containing sequences are placed under the control of original gene III promoter (shown in FIG. 19B). Phage ELISA assay was carried out to screen phage-positive clones as described in Example 1. 3 out off 10 clones were found to generate phage particles. Clone 3 was used for large-scale phage preparation.

B. Generation of GMCT-UltraHelper Phage:

Phage plaques formation assay was carried out according to procedures described above. The phage yield for GM- UltraHelper helper phage was approximately 8×10$^{11}$/ml culture, which was similar with that of M13KO7 and KO7kpn helper phages. The GR2-Myc domains can be removed from the surface of phage by trypsin.

C. Uses of the GMCT-UltraHelper Phage for Expressing Antigen-Binding Units:

The phagemid vector pABMX14 was used for phage display in combination with the GMCT UltrHelperelper phages. The single-chain antibody AM1 was subcloned into the pABMX14 vector (refer to as pABMX14-AM1). PABMX14-AM1 was transformed into TG1 cells, and the cells were superinfected with GMCT-UltraHelper phage with a multiplicity of infection (MOI) of 1 or 10 or 50 or 100. Phage particles were generated and purified as described in Example 1. The single chain antibody displayed on the phage surface was detected by phage ELISA using plates coated with AM1-antigen. The secondary antibody was HRP-conjugated anti-M13 antibody. The ELISA results demonstrated that the phagemid particles generated from all four MOI infections had similar activity binding to AM1-antigen, indicating that functional single-chain antibodies were displayed on the phage surface (FIG. 20). The control phagemids generated from TG1 carrying pABMX14-AM1/M13KO7 vectors exhibit no detectable binding affinity to AM1-antigen. The phage particles were also used for western blot analysis. As shown in FIG. 21, the scFv antibody was displayed upon infection with GMCT-UltrHelper phages and not control M13KO7 helper phages.

Example 5

Enrichment of Phages Displaying Desired Polypeptides by Panning

A diverse DNA sequences can be cloned into either pABMX14 or pABMX15 vector for production of soluble polypeptides. This expression library can be used for displaying encoded polypeptide upon infection with the subject UltrHelper phages (GM and GMCT for pABMX14, CM for pABMX15). The specific protein or peptide displayed on phage can be enriched by several round of panning from a diverse library. The panning process is described as follows. Briefly, a 96-well plate is coated with specific antigens at a concentration of 1-10 ug/ml for overnight at 4° C. After wash with PBS and blocking with 5% milk/PBS. 10$^{11-12}$ phages are added and incubated for 2 hours at room temperature. After several washing with PBST and PBS, the bound phages are eluted with 10 ug/ml trypsin for 30 min, since all of subject UltrHelper phages have a cleavable Myc-tag fused to pIII protein. Trypsin elution is more efficient than 100 mM triethylamine (usually used in conventional phage panning) in our experiments. Upon repeating the process for several times, phages displaying the desired polypeptide can be enriched.

Example 6

Preparation and Uses of Bacterial Helper Vector

A. Construction of Expression Vector and Bacterial Helper Vector:

The expression vector pABMX22 is constructed by replacing the sequence between the HindIII and SalI sites of vector pABMD1 (FIG. 22A) with a synthetic DNA fragment encoding the GR1 adapter and HA-tag. As shown in FIG. 25A, the vector contains an ampicillin-resistance gene for antibiotic selection (AMP), a plasmid replication origin (ColE1 ori), the fl phage replication origin (fl ori), and the lac promoter/lac O1 driving the expression of downstream sequence plac-RBS-p8L-GR1-HA-tag. The MluI/XbaI or MluI/NotI or XbaI/NotI restriction sites can be used to insert exogenous sequence for display or production of soluble protein in a bacterial cell. The complete vector sequence is shown in FIG. 25B.

The bacterial helper vector pABMbd-1 (FIG. 26A for vector map and 26B for the complete vector sequence) is derived from pBC-KS(+) vector from Stratagene. The sequences for multiple cloning sites between two BssHII sites in pBC-KS (+) are replaced by synthetic DNA fragment flanked-by MluI sites (with a compatible cohesive end to BssHII) at 5' and BssHII sites at 3', containing ribosome-binding sequence RBS, pelB leader sequence, the coding sequences for a chimeric outer membrane sequence consisting of the first 9 amino acids of E. coli major outer membrane lipoprotein (Lpp) and amino acids 46-159 of the outer membrane protein OpmA, and an adapter GR2 sequence. The lac Z promoter drives the expression of Lpp-OmpA-GR2 fusion, which will be secreted into the periplasmid of bacterial cells. The pAB-Mbd-1 vector contains a chloramphenicol-resistance gene (Cam) for antibiotic selection, a ColE1 ori origin for plasmid replication, and the fl phage replication origin (fl ori) for phagemid package.

B. Generation of Phagemid Particle Carrying Bacterial Helper Vector:

The pABMbd-1 helper vector is transformed into bacteria TG1 cells. A single pABbd-1 colony is picked and used to inoculate 15 ml 2× YT culture with 50 μg/ml chloramphenicol. After OD$_{600}$ reach to 0.8, the bacterial cells are infected by KO7Kpn helper phage at MOI 10 for 1 hour at 37° C. The infected TG1 cells are cultured in a 2-liter flask containing 500 ml 2×YT with chloramphenicol and kanamycin for overnight. The phagemid particles in the supernatants were then precipitated using polyethylene glycol (PEG)/NaCl, and re-suspended in phosphate-buffed saline (PBS). The phagemid concentration is determined by measuring OD$_{268}$. The phagemid particles packaging pABMbd-1 helper vector are then used for adapter-directed bacterial display.

C. Use of Bacterial Expression and Helper Vectors for Displaying Antigen-Binding Units:

The scFv antibody gene AM2 is cloned into pABMX22 vector. The TG1 bacterial cells containing this expression vector is grown to OD$_{600}$=0.8, and infected with the phagemid particle packaging bacterial helper vector pAB-Mbd-1. The TG1 cells harbored expression vector and helper vector are grown in 2× YT with ampicillin/cam overnight at 30° C., then harvested and washed with PBS. Since the displayed proteins are tagged with HA-tag, the anti-HA tag antibody can be used for detection the protein displayed on bacterial surface. For FACS analysis experiments, the cells resuspended in PBS are incubated with anti-HA tag antibody first, then incubated with fluorescein FITC-labeled anti-mouse antibody. After washing with PBS, the cells resuspended in PBS at 3-5×10$^7$/ml are counted on the basis of fluorescin intensity using a FACS sorter. The ELISA assay is also used for detect protein displayed on bacterial surface. First, AM2-antigen is coated onto ELISA plate for overnight at 4° C. After incubation with antigen for 2 hours, the cells bound to ELISA plate are detected with anti-HA antibody and HRP-conjugated anti-mouse antibody as described above.

A diverse antibody sequences can be cloned into pABMX22 vector for production of soluble antibody fragments. This expression library can be used to generate a selectable bacterial display library upon infection with the phagemid particle packaging the bacterial helper vector pAB- Mbd-1. The bacterial cells displaying antibodies are incubated with the FITC-labeled antigen, and sorted on the basis of fluorescin intensity using a FACS sorter. After sorting, the selected cells are grown in 2XYT broth with AMP overnight. Subsequently, the cells are subcultured into fresh medium, and infected with bacterial helper vector for display. The displayed cells are then used to run through another round of FACS sorting selection.

What is claimed is:

1. A phage helper vector comprising a nucleic acid sequence which encodes all of the outer-surface sequences required to package a phage genome wherein at least one of the outer-surface sequences is a recombinant protein comprising a coat protein fused in-frame to an adapter sequence.

2. The helper vector of claim 1, wherein the the phage is filamentous phage and the recombinant protein is a coat protein encoded by a gene selected from the group consisting of gene III, gene VI, gene VII, gene VIII, and gene IX.

3. The helper vector of claim 2, wherein the recombinant protein is pIII.

4. The helper vector of claim 2, wherein the adapter sequence is capable of pairwise interaction with a corresponding adapter to form a stable complex.

5. The helper vector of claim 4, wherein the adapter is derived from a heterodimeric receptor and adopts a coiled coil structure.

6. The helper vector of claim 4, wherein the adapter is derived from a $GABA_B$ receptor.

7. The helper vector of claim 4, wherein upon infection of a host cell carrying a phagemid vector which comprises a library of exogenous polypeptide sequences fused in frame to an adapter that is capable of pairwise interaction with the adapter fused in frame to the recombinant coat protein, the helper vector functions to cause the exogenous sequences to be displayed on the surface of packaged phage particles.

8. The helper vector of claim 6, wherein the adapter sequence is derived from $GABA_B$ receptor 2.

9. The helper vector of claim 7, wherein the adapter sequences further comprises the spacer sequence ValGlyGlyCys.

10. A phage helper vector selected from GM-UltraHelper phage vector, CM-UltraHelper phage vector, and GMCT-UltraHelper phage vector.

11. The helper vector of claim 1, wherein the vector optionally comprises one or more copies of the outer-surface coat protein selected for use as the recombinant fusion protein.

* * * * *